United States Patent
Chen

(10) Patent No.: US 7,501,092 B2
(45) Date of Patent: Mar. 10, 2009

(54) MANGANESE DOPED UPCONVERSION LUMINESCENCE NANOPARTICLES

(75) Inventor: Wei Chen, Stillwater, OK (US)

(73) Assignee: Nomadics, Inc., Stillwater, OK (US)

(*) Notice: Subject to any disclaimer, the term of this patent is extended or adjusted under 35 U.S.C. 154(b) by 602 days.

(21) Appl. No.: 11/202,005

(22) Filed: Aug. 11, 2005

(65) Prior Publication Data

US 2006/0140240 A1    Jun. 29, 2006

Related U.S. Application Data

(63) Continuation of application No. 10/166,313, filed on Jun. 6, 2002, now Pat. No. 7,008,559.

(60) Provisional application No. 60/296,333, filed on Jun. 6, 2001.

(51) Int. Cl.
    *G01N 33/00* (2006.01)
(52) U.S. Cl. .................. 422/53; 422/68.1; 422/82.05; 422/82.06; 422/82.07
(58) Field of Classification Search ............... 422/53, 422/68.1, 82.05, 82.06, 82.07
    See application file for complete search history.

(56) References Cited

U.S. PATENT DOCUMENTS

| | | |
|---|---|---|
| 3,706,673 A | 12/1972 | Wainer |
| 4,236,078 A | 11/1980 | Kotera et al. |
| 4,239,968 A | 12/1980 | Kotera et al. |
| 4,571,496 A | 2/1986 | Arakawa et al. |
| 5,348,687 A | 9/1994 | Beck et al. |
| 5,446,286 A | 8/1995 | Bhargava |
| 5,507,976 A | 4/1996 | Bringley et al. |
| 5,534,709 A | 7/1996 | Yoshimoto et al. |
| 5,585,640 A | 12/1996 | Huston et al. |
| 5,606,163 A * | 2/1997 | Huston et al. ............... 250/337 |
| 5,637,258 A | 6/1997 | Goldburt |
| 5,639,400 A | 6/1997 | Roberts et al. |
| 5,655,815 A | 8/1997 | Lohmeyer |
| 5,656,815 A | 8/1997 | Justus et al. |
| 5,811,822 A | 9/1998 | Huston et al. |
| 5,891,656 A | 4/1999 | Zarling et al. |
| 5,952,665 A | 9/1999 | Bhargava |
| 5,952,666 A | 9/1999 | Nakano et al. |
| 5,985,173 A | 11/1999 | Gray |
| 5,990,479 A | 11/1999 | Weiss et al. |
| 6,039,894 A | 3/2000 | Sanjurjo et al. |
| 6,048,616 A | 4/2000 | Gallagher et al. |
| 6,057,565 A | 5/2000 | Yoshida |
| 6,087,666 A | 7/2000 | Huston et al. |
| 6,090,200 A | 7/2000 | Gray et al. |

(Continued)

OTHER PUBLICATIONS

U.S. Appl. No. 60/271,308, filed Feb. 23, 2001, Hieronymus.

(Continued)

*Primary Examiner*—Sam P Siefke
(74) *Attorney, Agent, or Firm*—Dunlap Codding, P.C.

(57) ABSTRACT

The present relates in general to upconversion luminescence ("UCL") materials and methods of making and using same and more particularly, but not meant to be limiting, to $Mn^{2+}$ doped semiconductor nanoparticles for use as UCL materials. The present invention also relates in general to upconversion luminescence including two-photon absorption upconversion, and potential applications using UCL materials, including light emitting diodes, upconversion lasers, infrared detectors, chemical sensors, temperature sensors and biological labels, all of which incorporate a UCL material.

19 Claims, 16 Drawing Sheets

U.S. PATENT DOCUMENTS

| | | | |
|---|---|---|---|
| 6,107,243 | A | 8/2000 | Inagaki et al. |
| 6,140,651 | A | 10/2000 | Justus et al. |
| 6,153,339 | A | 11/2000 | Huston et al. |
| 6,207,392 | B1 | 3/2001 | Weiss et al. |
| 6,211,526 | B1 | 4/2001 | Huston et al. |
| 6,241,819 | B1 | 6/2001 | Bhargava et al. |
| 6,307,212 | B1 | 10/2001 | Huston et al. |
| 6,361,956 | B1 | 3/2002 | Hanninen et al. |
| 6,379,583 | B1 | 4/2002 | Gray et al. |
| 6,558,575 | B2 | 5/2003 | Andriessen et al. |
| 6,576,355 | B2 | 6/2003 | Yadav et al. |
| 6,605,565 | B1 | 8/2003 | Zhang et al. |
| 6,607,779 | B2 | 8/2003 | Yadav et al. |
| 6,607,821 | B2 | 8/2003 | Yadav et al. |

OTHER PUBLICATIONS

Felix, C., C. Sieber, W. Harbich, J. Butlet, I. Rabin, W. Schulze, and G. Ertl, "Fluorescence and Exitation Spectra of Ag4 in an Argon Matrix," *Chem. Phys. Lett.*, vol. 313, iss. 1-2, pp. 105-109 (Nov. 5, 1999).

Felix, C., C. Sieber, W. Harbich, J. Buttet, I. Rabin, W. Schylze, and G. Ertl, "Ag8 Fluorescence in Argon," *Phys. Rev. Lett.*, vol. 86, iss. 14, pp. 2992-2995 (Apr. 2, 2001).

Finley, J.J. et al., "Electrical Detection of Optically Induced Charge Storage in Self-Assembled InAs Quantum Dots," Appl. Phys. Lett., vol. 73, iss. 18, pp. 2618-2620 (Nov. 2, 1998).

Freedhoff, M.I., A.P. Marchetti, and G.L. McLendon, "Optical Properties of Nanocrystalline Silver Halides," Journal of Luminescence, vol. 70, iss. 1-6, pp. 400-413 (Oct. 1996).

Gaponik, N., D.V. Talapin, A.L. Rogach, K. Hoppe, E.V. Shevchencko, A. Kornowski, A. Eychmuller, H. Weller, "Thiol-capping of CdTe nanocrystals: an alternative to organometallic synthetic routes," Journal of Physical Chemistry B, 2002, vol. 106, iss. 39, p. 7177-7185.

Gasiot, J., P. Braunlich, and J.P. Fillard, "Nanosecond Infrared Laser Stimulation of Luminescence in Rare-Earth Doped Sulfides," *Appl. Phys. Lett.*, vol. 40, iss. 5, pp. 376-378 (Mar. 1982).

Golovan L.A. et al., "Observation of Two-Step Excitation of Photoluminescence in Silicon Nanostructures," Pisma Zh. Eksp. Teor. Fiz, vol. 68, pp. 732 (1998)[JETP letters, vol. 68, iss. 10, pp. 770-774 (Nov. 25, 1998).

Gudel, H.U. et al., "Design of Luminescent Inorganic Materials: New Photophysical Processes Studied By Optical Spectroscopy," Acc. Chem. Res., vol. 33, iss. 4, pp. 235-242 (2000).

Gudel, H.U. et al., "New Photon Upconversion Processes in Yb3+doped CsMnCl3 and RbMnCl3," Chemical Physics Letters, vol. 320, iss. 5-6, pp. 639-644, (Apr. 14, 200).

Gurvich, A.M., R.S. Mil'Shtejn, M.G. Myakhkova, S.I. Golovkova, J. Ruediger, and V.P. Kavtorova, "Photostimulable Luminescence Screens and Their Application in Clinical Dosimetry," *Rad. Prot. Dosimetry*, vol. 34, iss. 1/4, pp. 265-267 (1990).

Haase, M., K. Riwotzki, H. Meyssamy, A. Kornowski, "Synthesis and properties of colloidal lanthanide-doped nanocrystals," Journal of Alloys and Compounds, 2000, vol. 303-304, pp. 191-197.

Hamelin, N., P.G. Kik, J.F. Suyver, K. Kikoin, A. Polman, A. Schsonecker, and F.W. Saris, "Energy Backtransfer and Infrared Photoresponse in Erbium-doped Silicon p-n Diodes," J. Appl. Phys., vol. 88, iss. 9, pp. 5381-5387 (Nov. 1, 2000).

Hamilton, J.F., "The Silver Halid Photographic Process," Adv. Phys., vol. 37, iss.4, pp. 359-441 (1988).

*Handbook of Nanostructured Materials and Nanotechnology*, edited by Dr. Hari Singh Nalwa, vols. 1-5, San Diego, Academic Press, pp. 1-5, 1999.

*Handbook of Nanostructured Materials and Nanotechnology: Optical Properties*, vol. 4, edited by Hari Singh Halwa, Academic Press, pp. 451-457, 2000.

Hangleiter, T., F. K. Koschnick, J-M. Spaeth, R. H. D. Nuttal and R. S. Eachus, "Temperature Dependence of the Photostimulated Luminescence of X-irradiate BaFBr:Eu2+," J. Phys. an Institute of Physics Journal, vol. 2, iss. 32, pp. 6837-6846, (Aug. 13, 1990).

Harbich, W., S. Fedrigo, F. Meyer, D.M. Lindsay, J. Lignieres, J.C. Rivoal, and D. Kreisle, "Deposition of Mass Selected Silver Clusters in Rare Gas Matrices," *J. Chem. Phys.*, vol. 93, iss. 12, pp. 8535-8543 (Dec. 15, 1990).

Hasan, Z., L. Biyikli, and P. I. MacFarlane, "Power-gated Spectral Holeburning in MgS:Eu2+, Eu3+:A Case For High Density Persistent Spectral Holeburning," Appl. Phys. Lett., vol. 72, iss. 26, pp. 3399-3401 (Jun. 29, 1998).

Henry, C.H. and K. Nassau, "Lifetimes of Bound Excitons in CdS," J. Lumin. vol. 1&2, pp. 299-306 (1970).

Herron, N., "Zeolites as Hosts for Novel Optical and Electronic Materials," J. Inclusion Phenomena and Molecular Recognition in Chemistry, vol. 21, pp. 283-298 (1995).

Hess, B.C., I. G. Okhrimenko, R. C. Davis, B. C. Stevens, Q. A. Schulzke, K. C. Wright, C. D. Bass, C. D. Evans, and S. L. Summers, Surface Transformation and Photoinduced Recovery in CdSe Nanocrystals,: Phys. Rev. Lett., vol. 86, iss. 14, pp. 3132-3134 (Apr. 2, 2001).

Hoheisel, W., V.L. Colvin, C.S. Johnson, and A.P. Alivisatos, "Threshold For Quasicontinuum Absorption and Reduced Luminescence Efficiency in CDSE Nanocrystals," J. Chem. Phys., vol. 101, iss. 10, pp. 8455-8460 (Nov. 15, 1994).

Holliday, K., C. Wei, M. Cricu, and U. P. Wild, "Spectral Holeburning Measurements of Optical Dephasing Between 2-300 K in Sm2+ Doped Substitutionally Disordered Microcrystals," J. Lumin., vol. 53, iss. 1-6, pp. 227-230 (Jul. 1992).

Hong, K., R. S. Meltzer, B. Bihari, D. K. Willians and B. M. Tissue, "Spectral Hole Burning in Crystalline Eu2O3 and Y2O3:Eu3+ Nanoparticles," J. Lumin. vol. 76-77, pp. 234-237 (Feb. 1998).

http://home.fujifilm.com/products/science/ip/principle.html.

http://www.ml.wpafb.af.mil.

Ignatiev, I.V., et al., "Anti-Stokes Photoluminescence of InP Self-Assembled Quantum Dots in Presence of Electric Current," Phys. Rev. B, vol. 60, iss. 20, pp. R14 001-14 004 (Nov. 15, 1999).

Iwabuchi, Y., N. Mori, K. Takahashi, T. Matsuda and S. Shionaya, "Mechanism of Photostimulated Luminescence Process in BaFBr:Eu2+ Phosphors," Jpn. J. Appl. Phys., vol. 33, iss. 1a, pp. 178-185 (Jan. 15, 1994).

Jacobs, P.A., J. B. Uytterhoeven, and H. Beyer, "Some Unusual Properties of Activated and Reduced AgNaA Zeolites," J. Chem. Soc. Faraday Trans. I, vol. 75, pp. 56-64 (1979).

Jia, W , H. Yuan, L. Lu, H. Liu, and W.M. Yen, "Phosphorescent dynamics in SrAl2O4:Eu2+,Dy3+ Single Crystal Fibers," *J. Lumin.*, vol. 76-77, pp. 424-428 (Feb. 1998).

Jia, W., H. Yuan, S. Holmstrom, H. Liu, and W. M. Yen, "Photostimulated Luminescence in SrAl2O4:Eu2+,Dy3+ Single Crystal Fibers," J. Lumin., vol. 83-84, , pp. 465-469 (Nov. 1999).

Joly, Alan G., Wei Chen, and Jin. Z. Zhang, "Temperature dependence of Up-Conversion Luminescence of $Mn^{2+}$ in ZnS:Mn Nanoparticles," Phys. Rev. B (submitted).

Jorgensen, C.K., in Halogen Chemistry, vol. 1, P65, Academy Press, N. Y. (1967).

Kapitonov, M. et al., "Luminescence Properties of Tiol-Stabilized CdTe Nanocrystals," J. Phys. Chem. B, vol. 103, iss. 46, pp. 10109-10113 (Nov. 18, 1999).

Kaszuba, M., "The Measurement of Nanoparticles Using Photo Correlation Spectroscopy and Avalanche Photo Diodes," J. Nanoparticle Research, vol. 1, iss. 3, pp. 405-409 (1999).

Kellerman, R. and J. Texter, "Optical Absorption of Silver Atoms and Silver Clusters in Zeolite-Y," J. Chem. Phys., vol. 70, iss. 3, pp. 1562-1563 (Feb. 1, 1979).

Klimov, V.I., et al., "Quantization of Multiparticle Auger Rates in Semiconductor Quantum Dots." Science, vol. 287, iss 5455, pp. 1011-1013, (Feb. 11, 2000).

Knox, R.S., "Theory of Excitons," Solid State Physics Supplement 5, Academic Press, New York, 1963, pp. 112-128.

Koschnik, F.H., J. M. Spaeth, R. S. Eachus, W. G. McDugle, and R. H. D. Nuttal, "Experimental Evidence For The Aggregation of Photostimulable Centers in BaFBr:Eu2+ Single Crystals By Cross Relaxation Spectroscopy," Phys. Rev. lett. vol. 67, iss. 25, pp. 3571-3574 (Dec. 16, 1991).

Koto, K., "Photostimualable phosphor radiography design consideration," American Association of Physicists in Medicine Monograph #20, Woodbury, NY: AIP, 1994, pp. 731-769.

Kotov, N.A.; Dekany, I.; Fendler, J. H., "Layer-by-Layer Self-Assembly of Polyelectrolyte-Semiconductor Nanoparticle Composite Films," J.Phys.Chem. vol. 99, iss. 35, pp. 13065-13069 (Aug. 31, 1995).

Lakshmanan, A.R., "Radiation Induced Defects and Photostimulated Luminescence Process in BaFBr:Eu2+," Phys. Stat. Sol. (A) vol. 153, pp. 3-27 (1996).

Lenth, W. and R.M. MacFarlane, "Upconversion Lasers, Optics and Photonics News" (Mar. 1992) pp. 8-14.

Lesser, C., M. Gao, S. Kirstein, "Highly Luminescent Thin Films From Alternating Deposition of CdTeNanoparticles and Polycations," Materials Science & Engineering, C8-9, 159-162 (Dec. 1, 1999).

Lindmayer, J., "A New Erasable Optical Memory," Sol. Stat. Technol., vol. 31, 135-138 (Aug. 1988).

Lundstrom, T., W. Schoenfeld, H. Lee, P. M. Petroff, "Exciton Storage in Semiconductor Self-Assembled Quantum Dots," Science, vol. 286, iss. 5448, pp. 2312-2314 (Dec. 17, 1999).

Marchetti, A.P., A.A. Muenter, R.C. Baetzold, and R.T. McCleary, "Formation and Spectroscopic Manifestation of Silver Clusters on Silver Bromide Surfaces," J. Phys. Chem. B, vol. 102, iss. 27, pp. 5287-5297 (1998).

Masumoto, Y., "Persistent Hole Burning in Semiconductor Nanocrystals," J. Lumin., vol. 70, iss. 1-6, pp. 386-399 (Oct. 1996).

Masumoto, Y. and S. Ogasawara, "Photostimulated Luminescnece of CuCl Quantum Dots in NaCl Crystals," Jpn. J. Appl. Phys., part 2, vol. 38, Iss. 6A/B, pp. L623-L625 (Jun. 15, 1999).

MacMabon, H., S. Sanada, K. Doi, M. Giger, X. W. Xu, F. F. Yin, S. M. Montner, M. Carlin, "Direct Comparison of Conventional and Computer Radiography With a Dual-Image Recording Technique," Radiographics, vol. 11, iss. 2, pp. 259-268 (Mar. 1991).

Meijerink, A. and G. Biasse, "Photostimulated Luminescence and Thermally Stimulated Luminescence of Some New X-Ray Storage Phosphors," J. Phys. D: Appl. Phys., vol. 24, iss. 14, pp. 626-632 (Apr. 14, 1991).

Micic, O.I., M. Meglic, D. Lawless, D.K. Sharma, and N. Serpone, "Semiconductor Photophysics, 5. Charge Carrier Trapping In Ultrasmall Silver Iodide Particles And Kinetics of Formation of Silver Atom Clusters," Langmuir, vol. 6, iss. 2, pp. 487-492 (1990).

Miyahara, Y.A., "Imaging Plate Illuminates Many Fields," Nature, vol. 336, pp. 89-90 (Nov. 3, 1988).

Moerner, W.E., "Persistent Spectral Hole-Burning: Science and Applications," Springer-Verlag, 1988.

Mungan, C.E., T.R. Gosnell, "Laser Cooling of Solids," Advances in Atomic, Molecular, and Optical Physics, (1999), vol. 40, 161-165.

Murase, N. et al., "Fluorescence and EPR Characteristics of Mn2+-doped ZnS Nanocrystals Prepared By Aqueous Colloidal Method," J. Phys. Chem. B, vol. 103, iss. 5, pp. 754-760 (1999).

Nalwa, N.S., Editor, Handbook of Nanostructured Materials and Nanotechnology, Academic Press, San Diego (2000), vol. 4.

Nirmal, M., C. B. Murray, D. J. Norris and M. G. Bawendi, "Surface Electronic Properties of CdSe Nanocrystals," Z. Phys. D, vol. 26, pp. 361-363 (1993).

Nirmal, M. and L. E. Brus, "Luminescence Photophysics in Semiconductor Nanocrystals," ACC. Chem. Res., vol. 32, iss. 5, pp. 407-414 (1999).

Norris, D.J., M. Nirmal, C.B. Murray and M. G. Bawendi, "Size Dependent Optical Spectroscopy of II-VI Semiconductor nanocrystallites (Quantum Dots)," Z. Phys. D, vol. 26, iss. 355-357 (1993).

Nugent, L.J., In: K. W. Bagnall, Ed. "Lanthanides and Actinides". "Chemical Oxidations States of the Lanthanides and Actinides," MPT Int. Rev. Sci. Inorg. Chem., Ser. Two, Butterworths: London, vol. 7, pp. 195-219 (1975).

Ozin, G.A., F. Hugues, and S.M. Mattar, "Atomic Silver Fluorescent Probe of Metal-Support Interactions in Zeolites," J. Phys. Chem., vol. 89, iss. 2, pp. 300-304 (1985).

Ozin, G.A., "Nanochemistry: Synthesis in Diminishing Dimensions," Adv. Materials, vol. 4, iss. 10, pp. 612-649 (1992).

Paskov, P.P. et al., "Photoluminescence Upconversion in inAs/GaAs Self-Assembled Quantum Dots," Appl. Phys. Lett 77, iss. 6, pp. 812-814 (Aug. 7, 2000).

Peng, X.G., L. Manna, W. D. Yang, J. Wickham, E. Scher, A. Kadavanich, A. P. Alivisatos, "Shape Control of CdSe Nanocrystals," Nature, vol. 404, pp. 59-61 (Mar. 2, 2000).

Peng, Z.A. and X. G. Peng, Formation of High-Quality CdTe, CdSe, and CdS Nanocrystals Using CdO as precursors, J. Am. Chem. Soc., vol. 123, iss. 1, pp. 183-184 (Jan. 10, 2001).

Peyser, L.A., A. E. Vinson, A. P. Bartko, and R. M. Dickson, "Photoactivated Fluorescence from Individual Silver Nanoclusters," Science, vol. 291, iss. 5501, pp. 103 (Jan. 5, 2001).

Ping Yang[a], M. Lü, Dong Xü, D Yuan[a], G. Zhou, "Photoluminescence properties of ZnS nanoparticles co-doped with $Pb^{2}+$ and $Cu^{2}+$," Chemical Physics Letters, Mar. 9, 2001, vol. 336, iss. 1-2, p. 76-80.

Ping Yang[a], M. Lü, Dong Xü, D Yuan[a], G. Zhou, "ZnS nanocrystals co-activated by transition metals and rare-earth metals—a new class of luminescent materials," Journal of Luminescence 2001, vol. 93, p. 101-105.

Pollnau, M. et al., "Power Dependence of Upconversion Luminescence in Lanthanide and Transition-metal-ion System," Phys. Rev. B, vol. 61, iss. 5, pp. 3337-3346 (Feb. 1, 2000).

Rabin, I., W. Shultze, and G. Ertl, "Light Emission During the Agglomeration of Silver Clusters in Noble Gas Matrices," J. Chem. Phys, vol. 108, iss. 12, pp. 5137-5142 (Mar. 22, 1998).

Rabin, I., W. Shultze, G. Ertl, C. Felix, C. Sieber, W. Harbich, and J. Buttet, "Absorption and Fluorescence Spectra of Ar-matrix-isolated Ag3 Clusters," Chem. Phys. Lett., vol. 320, iss. 1-2, pp. 59-64 (Mar. 31, 2000).

Rao, R.P., M. De Murcia and J. Gasiot, "Optically Stimulated Luminescence Dosimetry," Radiat. Prot. Dosim., vol. 6, iss. 1-4, pp. 64-66 (1983).

Rashba, E.I. and G. E. Gurgenishvili, "Edge Absorption Theory in Semiconductors," Soviet Phys.-Solid State, vol. 4, iss. 4, pp. 759-760 (Oct. 1962).

Riseberg, L.A. and H.W. Mocs, "Multiphonon Orbit-Lattice Relaxation of Excited States of Rare-Earth Ions In Crystals," Phys. Rev., 1968, vol. 174, pp. 429.

Rocke, C., S. Zimmermann, A. Wixforth, and J. P. Kotthaus, "Acoustically Driven Storage of Light in a Quantum Well," Phys. Rev. Lett., vol. 78, iss. 21, pp. 4099-4102 (May 26, 1997).

Rodrigues, P.A.M., G. Tamulaitis, P. Y. Yu, and S.H. Risbud, "Size-Selective Photoluminescence Excitation Spectroscopy in CDSE Nanocrystals," Solid State Communications, vol. 94, iss. 8, pp. 583-587 (May 1995).

Ruter, H.H., H. V. Seggern, R. Reininger and V. Saile, Creation of Photostimulable Centers in BaFBr:Eu2+ Single Crystals By Vacuum Ultraviolet Radiation, Phys. Rev. Lett., vol. 65, iss. 19, pp. 2438-2441 (Nov. 5, 1990).

Ruter, H.H., H. Von Seggern, R. Reininger, and V. Saile, "Creation Efficiency of Photostimulable Centers in BaFBr:Eu2+ in the VUV and XUV Spectral Range," Phys. Stat. Sol. A, vol. 130, pp. K253-K256 (1992).

Sakabe, N., "Image Plate Protein Data: An Example of Experiment with a Weissenberg Camera Using SR in the Photon Factory," Acta Crystallography A, vol. 43 (supplement), pp. C-8 (1987).

Scheps, R., "Upconversion Laser Processes," Progress in Quantum Electronics (1996) vol. 20, iss. 4, pp. 271-358.

Secu, M., L. Matei, T. Serban, E. Apostol, GH. Aldica, and C. Silion, "Preparation and Optical Properties of BaFCl:Eu2+ X-ray Storage Phosphor," Optical Materials, vol. 15, iss. 2, pp. 115-122 (Nov. 2000).

Shaopeng Wang, Natalia Mamedova, Nicholas A. Kotov, Wei Chen, and Joel Studer, "Antigen/Antiody Immunocomplex from CdTe Nanoparticle Bioconjugates," Nanoletters, 2002, vol. 2, iss. 8, pp. 817-822.

Sharma, P., W. H. Jilavi, R. Nass, and H. Schmidt, "Tailoring the Particle Size from m-nm Scale By Using a Surface Modifier and Their Size Effect on the Fluorescence Properties of Europium Doped Yttria," Journal of Luminescence, vol. 82, iss. 3, pp. 187-193 (Sep. 1999).

Shulman, J.R., and W. D. Compton, "Color Centers in Solids," Pergamen Press: New York (1962).

Silver, J., M.I. Martinez-Rubio, T.G. Ireland, G.R. Fern, R. Withnall, "The Effect of Particle Morphology and Crystallite Size on a Upconversion Luminescence Properties of Erbium and Ytterbium Co-doped Yttrium Oxide Phosphors," Journal of Physical Chemistry B 2001, vol. 105, p. 948-953.

Smith, B.A., J.Z. Zhang, A. Joly, and J. Liu, "Luminescence Decay Kinetics of Mn2+doped Zns Nanoclusters Grown in Reverse Micelles," Phys. Rev. B, vol. 62, iss. 3, pp. 2021-2028 (Jul. 15, 2000).

Soltani, P., D. Brower, and G. Storti, "The Film Phosphor Screens on Fiber Optic Faceplates," Proc. SPIE: Electron Image Tubes and Image Intensifiers, vol. 1243, pp. 114-122 (Jul. 1990).

Sonda, M., M. Takano, J. Miyahara, and H. Kato, "Computed Radiography Utilizing Scanning Laser Stimulated Luminescence," Radiology, vol. 148, pp. 833-838 (Sep. 1983).

Sooklal, K., B.S. Cullum, S.M. Angel, and C.J. Murphy, "Photophysical Properties of ZnS Nanoclusters With Spatially Localized Mn2+," J. Phys. Chem., vol. 100, iss. 11, pp. 4551-4555 (1996).

Staros, J.V., "N-Hydroxysulfosuccinimide Active Esters:Bis (N-hydroxysulfosuccinimide) Esters of Two Dicarboxylic Acids Are Hydrophilic, Membrane-impermeant, Protein Cross-linkers," Biochemistry 1982, vol. 21, iss. 17, pp. 3950-3955.

Sun, T. and K. Seff, "Silver Clusters and Chemistry in Zeolites," Chem. Rev., vol. 94, iss. 4, pp. 857-870 (1994).

Sun, L.D., C. H. Liu, C, S. Liao amd C. H. Yuan, "ZnS Nanoparticles Doped With Cu(I) by Controlling coordination and Precipitation in Acqueous Solution," Journal of Materials Chemistry, vol. 9, iss. 8, pp. 1655-1657 (1999).

Swiatek, K., M. Godlewski, D. Hommel, "Deep Europium-Bound Exciton in a ZnS Lattice," Phys. Rev. B, vol. 42, iss. 6, pp. 3628-3633 (Aug. 15, 1990).

Takahashi, K., K. Kohda, J. Miyahara, Y. Kanemitsu, K. Amitani and S. Shionoya, "Mechanism of Photostimulated Luminescence in BaFX:Eu2+," J. Lumin., vol. 31/32, part 1, pp. 266-268 (1984).

Tamura, Y. and A. Shibukawa, "Optical Studies of CaS:Eu, Sm Infrared Stimulable Phosphors," Japanese Journal of Appl. Phys., Part 1, vol. 32, iss. 7, pp. 3187-3196 (Jul. 15, 1993).

Tan, T., and M. Murofushi, "Silver Microcluster on Silver Halide Grains as Latent Image and Reduction Sensitization Centers," *The Journal of Imaging Science and Technology*, vol. 38, iss 1, pp. 1-9 (Jan./Feb. 1994).

Tanaka, M. and Y. Masumoto, "Very Weak Temperature Quenching in Orange Luminescence of ZnS:Mn2+ Nanocrystals in Polymer," Chem. Phys. Lett., vol. 324, iss. 4, pp. 249-254 (Jul. 7, 2000).

Thoms, M., H. V. Seggerm and A.Winnacker, "Spatial Correlation and Photostimulability of Defect Centers in the X-ray-Storage Phosphor BaFBr:Eu2+," Phys. Rev. B, vol. 44, iss. 17, pp. 9240-9247 (Nov. 1, 1991).

Thoms, M., "Image Properties of Polycrystalline Storage Films," Applied Optics, vol. 35, iss. 19, pp. 3702 (Jul. 1996).

Thong, D.D. and O. Goede, "Optical Study of Highly Mn-Doped ZNS Crystals," Physica Status Solidi B, vol. 120,pp. K145-K150 (1983).

Tissue, B.M., "Synthesis and Luminescence of Lanthanide Ions in Nanoscale Insulating Hosts," Chemistry of Materials, vol. 10, iss. 10, pp. 2837-2845 (1998).

Tiwari, S., F. Rana, H. Hanafi, A. Hartstein, E. F. Crabbe, K. Chan, "A Silicon Nanocrystals Based Memory," Applied Physics Letters, vol. 68, iss. 10, pp. 1377-1379 (Mar. 4, 1996).

Tracht,S, L. Cruz, C. M. Stobba-Wiley, and J. V. Sweedler, "Detection of Radionuclides in Cappillary Electrophoresis Using a Phosphor-Imaging Detector," Analytical Chemjstry, vol. 68, iss. 2, pp. 3922-3927 (1996).

Van Bekkum, E. M. Flanigen, J. C. Jansen, "Introduction to Zeolite Science and Practice," Elsevier, Amsterdam, Feb. 1991.

Van Dijk, J.M.F. and M.F.H. Schuurmans, "On the Nonradiative and Radiative Decay Rates and a Modified Exponential Energy Gap Law for 4f-4f Transitions in Rare-Earth Ions," The Journal of Chemical Physics, vol. 78, iss. 9, pp. 5317-5323 (May 1, 1983).

Von Seggern, H., T. Voigt, W. Knupfer, and G. Lange, "Physical Model of Photostimulated Luminescence of X-ray Irradiated BaFBr:Eu2+," Journal of Applied Physics, vol. 64, iss. 3, pp. 1405-1412 (Aug. 1, 1988).

Von Seggern, H., A. Meijerink, T. Voigt, and A. Winnacker, "Photostimulation Mechanisms of X-ray-irradiated RbBr:Tl," Journal of Applied Physics, vol. 66, iss. 9, pp. 4418-4424 (Nov. 1, 1989).

Wang, Y., "Photophysical and Photochemical Processes of Semiconductor Nanoclusters," Advances in Photochemistry, vol. 19, pp. 181-192 (1994).

Watanabe, Y., G. Namikawa, T. Onuki, K. Nishio, and T. Tsuchiya, "Photosensitivity in Phosphate Glass Doped With Ag+ Upon Exposure to Near-ultraviolet Femtosecond Laser Pulses," Appl. Phys. Lett., vol. 78, iss. 15, pp. 2125-2127 (Apr. 9, 2001).

Winnacker, A., R. M. Shelby, R. M. MacFarlane, "Photon-Gated Hole Burning: A New Mechanism Using Two-Step Photoionization," Optics Letters, vol. 10, iss. 7, pp. 350-352 (Jul. 1985).

Wright, J.C., "Upconversion and Excited State Energy Transfer in Rare-Earth Doped Materials," Topics in Applied Physics: Radiation Processes in Molecules and Condensed Phase; F.K. Fong., Ed.; Springer: Berlin, (1976), pp. 239-295.

Wu, Y. and C. S. Shi, "Observation of Eu2+ and Tb4+ in SrMgF4:Eu8+," Solid State Communications, vol. 95, iss. 5, pp. 319-322 (1995).

Y. Gao, C. S. Shi, and Y. Wu, "Luminescence Properties of SrB4O7:Eu, Tb Phosphors," Materials Research Bulletin, vol. 31, iss. 5, pp. 439-444 (May 1996).

Wu, F., J.Z. Zhang, R. Kho, and R.K. Mehra, "Radiative and Nonradiative Lifetimes of Band Edge States and Deep Trap States of CdS Nanoparticles Determined By Time-Correlated Single Photon counting," Chemical Physics Letters, vol. 330, iss. 3-4, pp. 237-242 (Nov. 10, 2000).

Xie, P. and S.C. Rand, "Astigmatically Compensated, High Gain Cooperative Upconversion Laser," Applied Physics Letters, vol. 60, iss. 25, pp. 3084-3086 (Jun. 22, 1992).

Yang, P.D. et al., "Room-Temperature Ultraviolet Nanowire Nanolasers," Science, (Jun. 8, 2001) vol. 292, iss. 5523, pp. 1879-1881.

Yang, P., M. Lu, Dong Xu, D. Yuan, G. Zhou, "Photoluminescence Properties of ZnS Nanoparticles Co-Doped With Pb2+ and Cu2+", Chemical Physics Letters, Mar. 9, 2001, vol. 336, iss. 1-2, p. 76-80.

Yang, P., M. Lu, D. Xu, D. Yuan, G. Zhou, "ZnS Nanocrystals Co-Activated By Transition Metals and Rare-Earth Metals-A New Class of Luminescent Materials" Journal of Luminescence 2001, vol. 93, p. 101-105.

Yang, P.D., "Miniaturished Ultraviolet Lasers, Global Photonics Applications & Technology," World Markets Series, Business Briefing, 2002, pp. 42-47.

Yu, J.Q., H.M. Liu, Y.Y. Wang, F.B. Fernandez, and W. Y. Jia, "Optical Properties of ZnS:Mn2+ Nanoparticles in Polymer Films," Journal of Luminescence, vol. 76 & 77, pp. 252-255 (Feb. 1998).

Yusa, G. and H. Sakaki, "Trapping of Photogenerated Carriers by InAs Quantum Dots and Persistent Photoconductivity in Novel GaAs/n-AlGaAs Field-effect Transistor Structures," Applied Physics Letters, vol. 70, iss. 3, pp. 345-347 (Jan. 20, 1997).

Zaitoun, M.A., T. Kim, and C. T. Lin, "Observation of Electron-Hole Carrier Emission in the Eu3+-Doped Silica Xerogel," The Journal of Physical Chemistry B, vol. 102, iss. 7, pp. 1122-1125 (1998).

Zaitoun, M.A., D. M. Goken, L. S. Bailey, T. Kim, and C. T. Lin, "Thermoanalysis and Emission Properties of Eu3+/Eu2+ in Eu3+-Doped Xerogels," The Journal of Physical Chemistry B, vol. 104, iss. 2, pp. 189-196 (2000).

Zegrya, G.G; V.A. Kharchenko VA, "New Mechanism For Auger Recombination of Nonequilibrium Current Carriers In Semiconducting Heterostructures," Zh. Eksp. Teor. Fiz, 1992, vol. 101 pp. 327; Sov. Phys. JETP., Jan. 1992, vol. 74, pp. 173-181.

Zhang, J.Z., "Ultrafast Studies of Electron dynamics in Semiconductor and Metal Colloidal Nanoparticles: Effects of Size and Surface," Accounts of Chemical Research, vol. 30, iss. 10, pp. 423-429 (1997).

Zhang, H.X., C.H. Kam, Y. Zhou, X.Q. Han, S. Buddhudu, and Y.L. Lam, "Visible Upconversion Luminescence in ER3+:BaTiO3, nanocrystals," Optical Materials, (Sep. 2000), vol. 15, iss. 1, pp. 47-50.

Zhang, Jin Z., Wei Chen and Alan G. Joly, "Up-Conversion Luminescence of Mn2+ in ZnS:Mn2+ Nanoparticles," Physical Review B., vol. 64, iss. 4, pp. 0412021-0412024 (2001).

Zhou, J., L. T. Li, Z. L. Gui, S. Buddhudu, Y. Zhou, "Photoluminescence of CdSe Nanocrystallites Embedded in BaTiO3 Matrix," Applied Physics Letters, vol. 76, iss. 12, pp. 1540-1542 (Mar. 20, 2000).

Zijlmans, H., J. Bonnet, J. Burton, K. Kardos, T. Vail, R.S. Niedbala, and H.J. Tanke, Detection of Cell and Tissue Surface Antigens Using Up-Converting Phosphors: A New Receptor Technology, Analytical Biochemistry, (Feb. 1, 1999) vol. 267, iss. 1, pp. 30-36.

Zimmermann, S., A. Wixforth, J. P. Kotthaus, W. Wegscheider, M. Bichler, "A Semiconductor-Based Photonic Memory Cell," Science, 283, iss. 5406, pp. 1292-1295 (Feb. 26, 1999).

Capobianco et al., Enhancement of Red Emission ($^4F_{9/2} \rightarrow {^4I_{15/2}}$) via Upconversion and Nanocrystalline Cubic $Y_2O_3$: $Er^{3+}$, J. Phys. Chem. B, 2002, 106: 1181-1187.

Chen et al., Photostimulated Luminescence of silver clusters in zeolite-Y, Physics Letters A, 1997, 232:391-394.

Chen et al., Photostimulated Luminescence of AgI Clusters in zeolite-Y, J. Appl. Phys., 1998, 83(7): 3811-3815.

Cho et al., Dyanamics of anit-Stokes phtotluminescence in type-II $Al_xGA_{1-x}As$-$GaInP_2$ heterostructures: The important role of long-lived carriers near the interface, Physical Review B, 1997, 56(8): 375-378.

Diener et al., Strong low-temperature anti-Stokes photoluminescence from coupled silicon nanocrystals, Optical Materials, 2001, 17: 135-139.

Driessen et al., Interface-induced conversion of infrared to visible light at semiconductor interfaces, Physical Review B, 1996, 54(8): 263-266.

Gong et al., Photoluminescence and upconversion optical properties of the $CaS:Sm^{3+}$ nanocrystallites, Applied Physics Letters, 1998, 73(20): 2875-2877.

Heimbrodt et al., Luminescence, energy transfer and anti-Stokes PL in wide band-gap semimagnetic nanostructures, Journal of Luminescence, 2000, 87-89: 344-346.

Hellman et al., Low-temperature anti-Stokes luminescence mediated by disorder in semiconductor quantum-well structures, Physical Review B, 1995, 51(24): 18 053-056.

Huston et al., 2-D Radiation Imaging Using Optically Stimulated Luminescence Glass, 2001 NRL Review/ Optical Science, 169-170.

Huston et al., Remote optical fiber dosimetry, Nucl. Instr. Methods Phys. Res. B 184, 2001, 55-67.

Justus et al., Optically Stimulated Luminescence Dosimetry Using Doped Fused Quartz, Radiation Protection Dosimetry, 1999, 84(1-4): 189-192.

Justus et al., Optically and Thermally Stimulated Luminescence Characteristics of $Cu^+$-Doped Fused Quartz, Radiation Protection Dosimetry, 1999, 81(1): 5-10.

Kammerer et al., Photoluminescence Up-Conversion in Single Self-Assembled InAs/GaAs Quantum Dots, Physical Review Letters, 2001, 87(20): 207401-1-4.

Masumoto et al., Photosimulated luminescence of quantum dots, Journal of Luminescence, 2000, 87-89: 360-362.

Naval Research Laboratory, Fiber-Optic-Coupled Dosimeter For Ionizing Radiation.

Poles et al., Anti-Stokes photoluminescence in colloidal semiconductor quantum dots, Applied Physics Letters, 1999, 75(7): 971-973.

Silver et al., Yttrium Oxide Upconverting Phosphors. 3. Upconversion Luminescent Emission from Europium-Doped Yttrium Oxide under 632.8 nm Light Excitation, J. Phys. Chem. B, 2001, 105: 9107-9112.

van Oijen et al., Continuous-wave two-photon excitation of individual CdS nanocrystallites, Applied Physics Letters, 2001, 79(6): 830-832.

Vetrone et al., NIR to Visible Upconversion in Nanocrystalline and Bulk $Lu_2O_3$:$Er^{3+}$, J. Phys. Chem. B., 2002, 106: 5622-5628.

Zhang et al., Green upconversion luminescence in $Er^{3+}$: $BaTiO_3$ films, Applied Physics Letters, 2000, 77(5): 609-611.

\* cited by examiner

Photoluminescence (1) and upconversion emission of free CdTe nanoparticles (2) and Bru38-CdTe nanoparticle bioconjugates (3); Excitation wavelengths are 350 nm for (1) and 750 nm for (2) and (3); all the data were taken at pH 6.7.

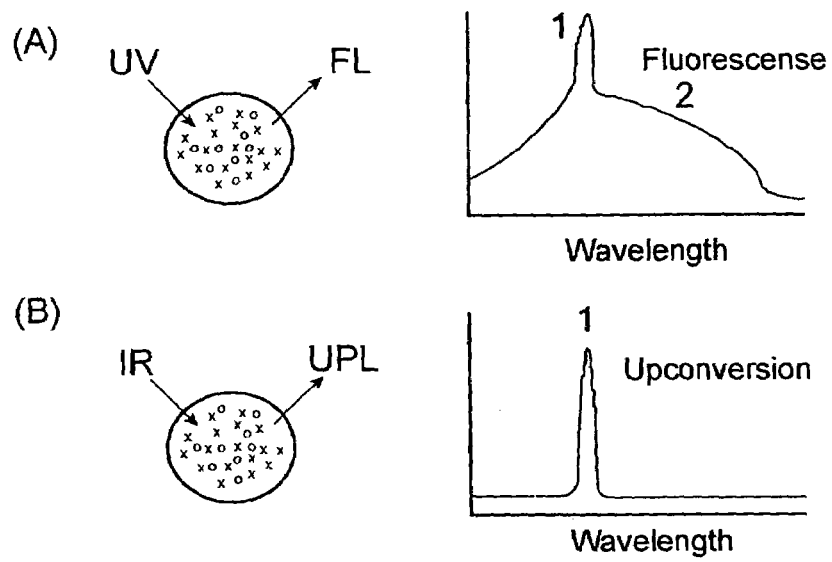
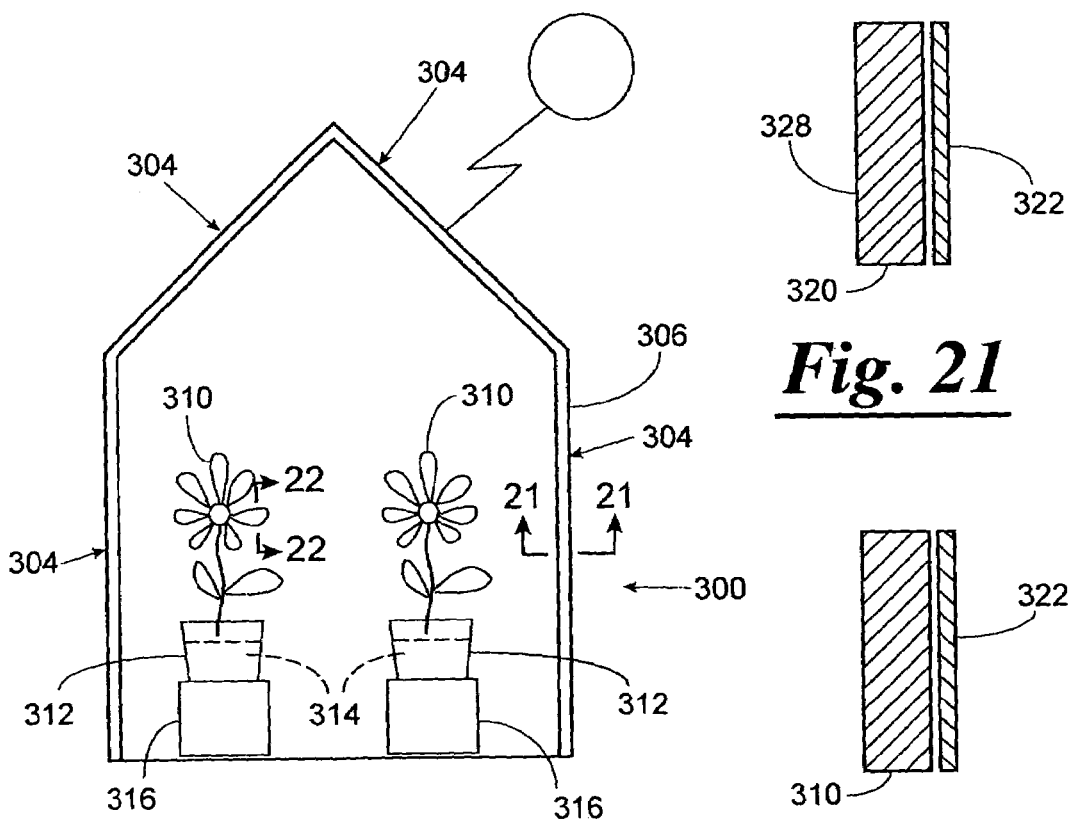

MANGANESE DOPED UPCONVERSION LUMINESCENCE NANOPARTICLES

CROSS REFERENCE TO RELATED APPLICATIONS

This application is a continuation of U.S. Ser. No. 10/166,313, filed Jun. 6, 2002 now U.S. Pat. No. 7,008,559, which claims priority under 35 U.S.C. § 119(e) of U.S. Provisional Application Ser. No. 60/296,333 filed Jun. 6, 2001 and entitled "UPCONVERSION OF Mn-DOPED SEMICONDUCTOR NANOPARTICLES", the contents of which are expressly incorporated herein by reference in their entirety.

STATEMENT REGARDING FEDERALLY SPONSORED RESEARCH OR DEVELOPMENT

The government may own certain rights in and to this application pursuant to: (i) a grant from the National Science Foundation Grant No. DMI-0060254, and (ii) an Air Force Office of Scientific Research Contract No. F49620-00-C-0058.

BACKGROUND OF THE INVENTION

1. Field of the Invention

The present relates in general to upconversion luminescence ("UCL") materials and methods of making and using same and more particularly, but not meant to be limiting, to $Mn^{2+}$ doped semiconductor nanoparticles for use as UCL materials. The present invention also relates in general to upconversion luminescence including two-photon absorption upconversion, and potential applications using UCL materials, including light emitting diodes, upconversion lasers, infrared detectors, chemical sensors, temperature sensors, pressure sensors, ultraviolet and radiation detectors and biological labels, all of which incorporate a UCL material.

2. Brief Description of the Related Art

The ever increasing demands of electronics and the interface between electronic and biological systems pushes frontier of electrical sciences and, in particular, the size and energy consumption of electronic elements. As the particle size of a material gets smaller and smaller, novel specific phenomena can be observed such as the shift of emission to shorter wavelength with decreasing size. Upconversion luminescence (UCL) is a type of fluorescence wherein the excitation wavelength entering a material capable of exhibiting UCL is longer than the emission wavelength of such a UCL material. Due to potential applications in lasers, laser cooling, optical communications, storage, displays, imaging techniques, optical sensing and biological probing, upconversion luminescence has been extensively investigated. See for example the references cited hereinafter, the contents of which are expressly incorporated herein by reference in their entirety.

UCL is extensively documented, in particular, in rare earth compounds in which the presence of more than one metastable excited f-f state results from the efficient shielding of the 4f electrons, including the upconversion luminescence of $Er^{3+}$ in $BaTiO_3$ nanoparticles. Recently, upconversion has been reported in some transition metal compounds as well—see e.g. H. U. Gudel et al., *New photon upconversion processes in $Yb^{3+}$ doped $CsMnCl_3$ and $RbMnCl_3$*, Chemical Physics Letters, (2000), 320, 639, hereinafter, the contents of which are expressly incorporated herein by reference in their entirety. The upconversion luminescence of $Mn^{2+}$ has been reported in $Yb^{3+}$ doped $CsMnCl_3$ and $RbMnCl_3$ compounds at temperatures below 100 K.

Searching for an upconversion material, we need to consider both the stability and the upconversion efficiency. According to the energy gap law (J. M. F. van Dijk and M. F. H. Schuurmans, *On the nonradiative and radiative decay rates and a modified exponential energy gap law for 4f-4f transitions in rare-earth ions*, J. Chem. Phys. 1983, 78: 5317-5323 and L. A. Riseberg and H. W. Moos, *Multiphonon orbit-lattice relaxation of excited states of rare-earth ions in crystals*, Phys. Rev. 1968, 174: 429), lower highest lattice phonon energies of an upconversion host can reduce the rate, at which a given energy gap is crossed non-radiatively by multiphonon relaxation. That is, the lower the highest lattice phonon energy, the higher the upconversion efficiency. Most investigations of upconversion focus on oxides and halides. Oxides are air-stable but upconversion luminescence in oxides is not efficient because the phonon energies in oxides are high (most are higher than 500 $cm^{-1}$) (P. Egger and J. Hulliger, *Optical materials for short wavelength generation*, Coordination Chemistry Review, 1999, 183: 101-115) and, thus, non-radiation rate is large, resulting in weak upconversion luminescence. In halides, the phonon energies is low (less than 350 $cm^{-1}$) (P. Egger and J. Hulliger, *Optical materials for short wavelength generation*, Coordination Chemistry Review, 1999, 183: 101-115), non-radiation rate is low, and, of course, upconversion luminescence efficiency is high. However, halides are not stable in air because they are more or less sensitive to moisture. Group II-VI semiconductors like ZnS are very stable and their phonon energies are somewhat higher than that of halides but much lower than that of oxides (For $ZnS:Mn^{2+}$, the phonon energy is 350 $cm^{-1}$) (A. Anastassiadou et al., *The luminescence spectrum of $Zn1-xMnxS$ under hydrostatic pressure*, Solid State Communications, 1988, 67:633-636). So, Group II-VI doped semiconductors are promising materials for upconversion due to their possibility of high upconversion efficiency and good stability. For example, the $ZnS:Mn^{2+}$ nanoparticle samples used in the testing and experiments of the presently claimed and disclosed invention were made in approximately 2000, but as of the filing date of the present application still retain high luminescence and a stable structure.

$Mn^{2+}$ doped semiconductors represent a class of phosphors that have already been utilized for many applications; however, no one has yet been able to report and/or demonstrate upconversion luminescence of $Mn^{2+}$-doped semiconductors.

The presently claimed and disclosed invention(s) is predicated upon the observance of upconversion luminescence of $Mn^{2+}$ in $ZnS:Mn^{2+}$ semiconductor nanoparticles at room temperature. This upconversion luminescence is also shown to be principally due to two-photon excitation. These $Mn^{2+}$-doped nanoparticles exhibiting UCL have unique and novel application as light emitting diodes, laser, optical communications, optical storage, infrared detection and imaging, chemical sensors, temperature and pressure sensing, radiation detection and biological probing. Additionally the presently disclosed and claimed invention provides for a novel methodology of distinguishing $Mn^{2+}$ ions at the lattice sites and the near-surface sites in nanoparticles.

A common use of upconversion is to convert longer wavelength (infrared) to shorter wavelength (visible) and/or from a low energy to a higher energy state. Upconversion luminescence of $Mn^{2+}$ is more efficient than that of rare earth ions because the d-d transition of $Mn^{2+}$ can be modified via crystal field and in nanoparticles can become allowed or partly allowed, while the manipulation of the f-f transition of rare earth ions is more difficult and can only be slightly improved by crystal field or the host environments.

For infrared imaging, the use of nanoparticle upconversion is beneficial due to the low or absence of light scattering, because the light scattering intensity is proportional to the 6$^{th}$ power of the particle size (I$\mu$R$^6$) (M. Kaszuba, *The measurement of nanoparticles using photon correlation spectroscopy and avalanche photo diodes*, Journal of Nanoparticle Research, (1999), 1, 405-409). Thus, compared to traditional micrometer-sized phosphors, light scattering in nanoparticles is nonexistent, which is ideal for imaging technology.

The surface-to-volume ratio of nanoparticles is very high. The attaching of chemicals or molecules to the nanoparticle surfaces changes the luminescence properties (intensity, emission energy and lifetime) of the nanoparticles greatly and rapidly. This provides for a new type of chemical sensors based on upconversion luminescence with high sensitivity.

The sizes of nanoparticles are comparable to the sizes of bio-molecules, and nanoparticles are soluble in water due to their small size and surface modification. Thus, highly luminescent nanoparticles are good labels for biological probing because they can combine with bio-molecules like antigens, anti-bodies, proteins or DNA or they can be inserted into biological systems such as a human or cell tissue. Some work has been done using undoped semiconductor nanoparticles. Until the present disclosure, however, no group has reported, discussed, or disclosed the use of doped nanoparticles and upconversion nanoparticles for biological systems. The application of undoped nanoparticles is based on photoluminescence in which the luminescence background and noise are very high due to the auto-fluorescence of the bio-molecules under ultraviolet excitation. Upconversion luminescence with an infrared excitation and a visible emission can avoid this shortcoming and thus improve the resolution and sensitivity of the upconversion luminescence assembly or molecule used, for example, as a biological sensor, probe or label.

At least one group (D. A. Zarling, M. J. Rossi, N. A. Peppers, J. Kane, G. W. Faris, M. J. Dyer, S. Y. Ng, and L. V. Schneider, Up-converting reporters for biological and other assays using laser excitation techniques, U.S. Pat. No. 5,891, 656, Apr. 6, 1999) has reported using upconversion of the traditional micrometer sized phosphors for biological probing, but these molecules are not soluble in water and do not easily combine with biomolecules. The size, solubility and the strong upconversion luminescence of the doped nanoparticles of the presently claimed and disclosed invention, however, allow for the production and use of high quality biological probing materials and methodologies. Upconversion luminescence of doped nanoparticles has advantages over both the photoluminescence of undoped nanoparticles and the upconversion of traditional phosphors. In addition, nanoparticles can reduce light scattering intensity as discussed above, improving resolution greatly.

Temperature and pressure sensors can also be manufactured using the UCL materials of the presently claimed and disclosed invention. The UCL materials are especially well suited for temperature sensors due to the sensitivity of the upconversion luminescence intensity to temperature as shown in detail hereinafter. For example, there exists a linear or a near linear relationship between the upconversion intensity and temperature for high quality nanoparticles like the ZnS:Mn$^{2+}$ nanoclusters encapsulated in zeolite. In addition, upconversion spectra, lifetime and temperature dependence measurements demonstrate that upconversion is a good method to reveal the luminescence characteristics of the Mn$^{2+}$ ions at the near-surface sites of semiconductor nanoparticles.

SUMMARY OF THE INVENTION

The present relates in general to upconversion luminescence ("UCL") materials and methods of making and using same and more particularly, but not meant to be limiting, to Mn$^{2+}$ doped semiconductor nanoparticles for use as UCL materials. The present invention also relates in general to upconversion luminescence including two-photon absorption upconversion, and potential applications using UCL materials, including light emitting diodes, upconversion lasers, infrared detectors, chemical sensors, temperature and pressure sensors, ultraviolet and radiation detectors and biological labels, all of which incorporate a UCL material.

BRIEF DESCRIPTION OF THE SEVERAL VIEWS OF THE DRAWINGS

FIG. 19 is a schematic diagram of the use of UV vs. IR excitation wavelengths for UCL materials in a biological system.

FIG. 20 is a schematic representation of a greenhouse constructed in accordance with the present invention.

FIG. 21 is a partial cross-sectional view of a light conveying panel constructed in accordance with the present invention, taken along the lines 21-21 in FIG. 20.

FIG. 22 is a cross-sectional view of a botanical item coated with a light converting material constructed in accordance with the present invention, taken along the lines 22-22 in FIG. 20.

DETAILED DESCRIPTION OF THE INVENTION

Figure 1:
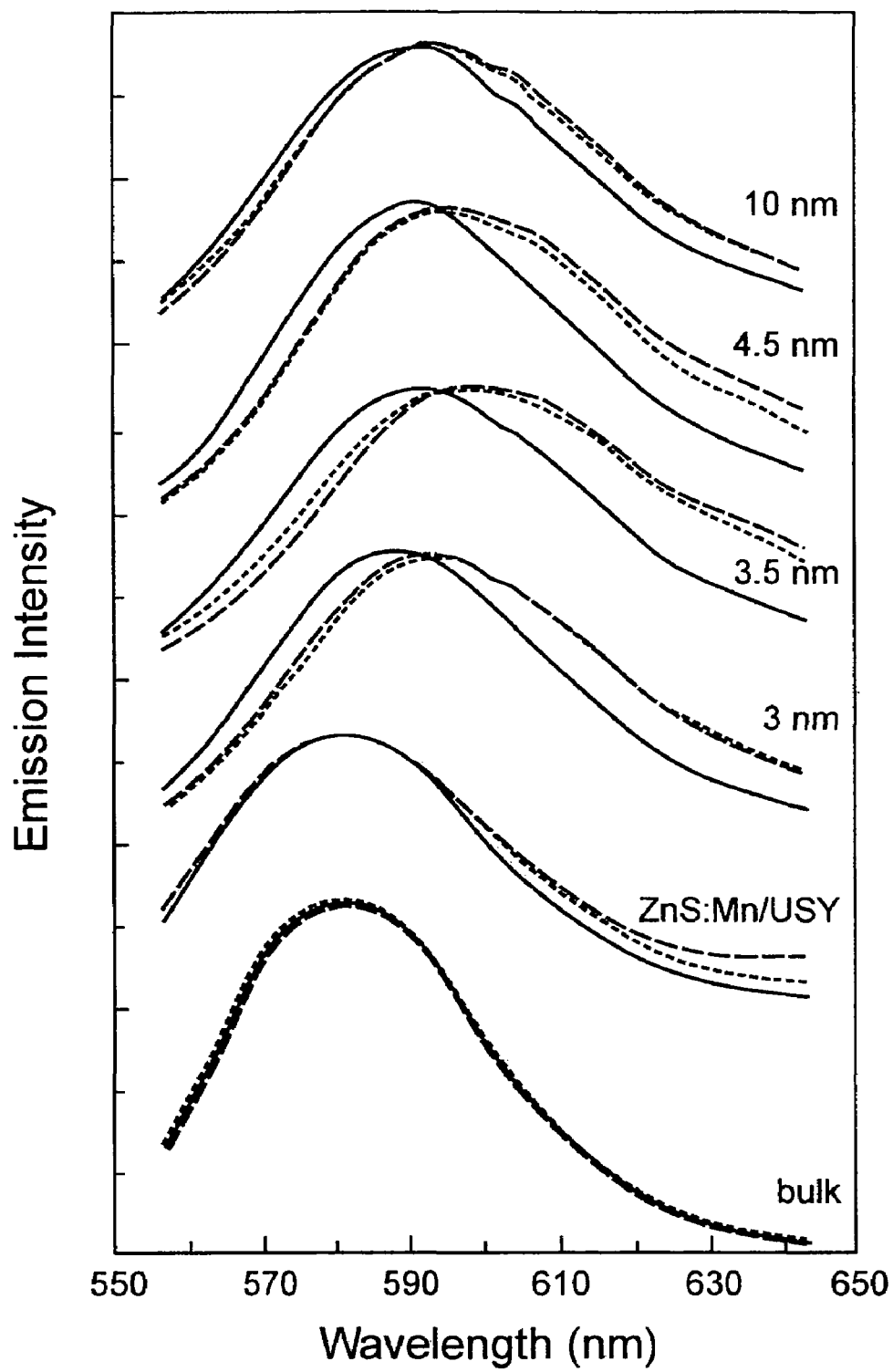
FIG. 1 is a graphical representation of the photoluminescence spectra after excitation at 300 nm (solid), at 383.5 nm (dash), and the upconversion luminescence spectra resulting from 767 nm excitation (dot) of ZnS:Mn$^{2+}$ bulk and nanoparticles.

Before explaining at least one embodiment of the invention in detail, it is to be understood that the invention is not limited in its application to the details of construction, experiments, exemplary data, and/or the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

The term "nanoparticles" as used herein, can also refer to nanoclusters, clusters, particles, dots, quantum dots, small particles, nanostructured materials.

The presently disclosed and claimed invention relates, in general, to UCL materials and methods of making and using same. The UCL material is broadly defined as any material capable of UCL—i.e. any material capable of luminescence wherein the excitation wavelength is longer than the emission wavelength. More particularly, but not by way of limitation, the UCL material may be any host having a dopant or dopants operably associated therewith. In this embodiment of the UCL material, the dopant increases the fluorescence intensity or quantum efficiency of the host. In one specific embodiment, the host may be a nanoparticle, although one of ordinary skill in the art will appreciate that bulk materials may also be used. Nanoparticles do, however, have certain advantages over bulk materials—namely (i) high luminescence efficiency due to quantum confinement; (ii) emission and excitation energies tunable by size; (iii) low excitation power due to the increase of absorbance with decreasing size; (iv) low light scattering; (v) ease of production; (vi) thin film applications/ability; and (vii) wide industry application (e.g. infrared detection, safety control and surveillance, biological probing and labeling, and weather reporting and pollution control, etc.). Thus, without detracting or limiting the breadth of the presently claimed and disclosed UCL material, one of ordinary skill in the art (given this disclosure) would appreciate that UCL materials fabricated from doped nanoparticles would have certain advantages over a UCL material fabricated from bulk materials or conventional phosphors.

When the term "nanoparticle" is used, one of ordinary skill in the art will appreciate that this term encompasses all materials with small size and quantum size confinement, generally the size is less than 100 nm. As a new type of materials, nanoparticles are luminescent with high quantum efficiency and are good candidates for upconversion luminescence. It is known that oscillator strength is a very important optical parameter that determines the absorption cross-section, recombination rate, luminescence efficiency, and the radiative lifetime in materials. The oscillator strength of the free exciton is given by (W. Chen, A. G. Joly, and Z. Z. Zhang,

*Upconversion luminescence of $Mn^{2+}$ in $ZnS:Mn^{2+}$ nanoparticles, Phys. Rev. B 64, 41, 202 (2001)*):

$$f_{ex} = \frac{2m}{\hbar}\Delta E|\mu|^2|U(0)|^2$$

where m is the electron mass, $\Delta E$ is the transition energy, $\mu$ is the transition dipole moment, and $|U(0)|^2$ represents the probability of finding the electron and hole at the same site (the overlap factor). In nanostructured materials, the electron-hole overlap factor increases largely due to the quantum size confinement, thus yielding an increase in the oscillator strength. The oscillator strength is also related to the electron-hole exchange interaction that plays a key role in determining the exciton recombination rate. In bulk semiconductors, due to the extreme dislocation of the electron or hole, the electron-hole exchange interaction term is very small; while in molecular-size nanoparticles, due to the confinement, the exchange term should be very large. Therefore, we may expect a large enhancement of the oscillator strength from bulk to nanostructured materials.

In doped semiconductors, excitons are bound to impurity centers. The oscillator strength is given by (W. Chen, R. Sammynaiken, and Y. Huang, *Luminescence enhancement of ZnS:Mn nanoclusters in zeolite, J. Appl. Phys.* 88, 5188 (2000) and W. Chen, X. H. Zhang, and Y. Huang, *Luminescence enhancement of EuS nanoclusters in zeolite*, Appl. Phys. Lett., 2000, 24, 2328-2330):

$$f=f_{ex}|\int dx F(x)|^2/\Omega_{mol},$$

where $f_{ex}$ is the oscillator strength of the free exciton and $\Omega_{mol}$ is the volume of one molecule. The oscillator strength of a bound exciton is actually given by $f_{ex}$ multiplied by the number of molecules covered by the overlap of the electron and hole wavefunctions. Clearly, quantum size confinement will also enhance the bound exciton oscillator strength in doped nanoparticles. The luminescence efficiency is also proportional to the excitation oscillator strength; therefore, it can be enhanced via quantum size confinement. Strong evidences for the above theory are from our observations on $ZnS:Mn^{2+}$ (W. Chen, R. Sammynaiken, and Y. Huang, *Luminescence enhancement of ZnS:Mn nanoclusters in zeolite, J. Appl. Phys.* 88, 5188 (2000)) and EuS (W. Chen, X. H. Zhang, and Y. Huang, *Luminescence enhancement of EuS nanoclusters in zeolite*, Appl. Phys. Lett., 2000, 24, 2328-2330) nanoparticles. The luminescence intensity of the 1 nm sized $ZnS:Mn^{2+}$ nanoparticles in zeolite-Y is much stronger than other nanoparticles. More interesting is that bulk EuS at room temperature is not luminescent but strong luminescence is observed when EuS nanoparticles were formed in zeolite.

The radiative decay lifetime (t) is closely related to the oscillator strength of a transition (W. Chen, R. Sammynaiken, and Y. Huang, *Luminescence enhancement of ZnS:Mn nanoclusters in zeolite, J. Appl. Phys.* 88, 5188 (2000)):

$$\tau=4.5(\lambda_A^2/nf),$$

where n is the refractive index and $\lambda_A$ is the wavelength. Thus, the lifetime is shortened with decreasing size due to the increase of the oscillator strength, f. High efficiency with short decay enables nanoparticles very good candidates for luminescence sensors. In addition, small size and ultrathin films enable nanothermometry have high sensitivity and accuracy. These are expected to be the advantages of nanoparticles for upconversion. Therefore, the nanoparticle materials in this disclosure are not limiting to semiconductors but including non-semiconductors such as oxides and halides.

$ZnS:Mn^{2+}$, for example, exhibits strong UCL in both bulk and nanoparticles. Indeed, the UCL is visible to the naked eye up to very low power densities. The UCL spectra in the presently claimed and disclosed invention were recorded with a laser power density of 100 mJ/cm$^2$. The UCL is visibly detectable at power densities of at least 1 mJ/cm$^2$. Furthermore, UCL is detectable by a photo multiplier tube (PMT) or charged coupled device (CCD) at a power density <1 mJ/cm$^2$, such as 0.2 or 0.5 mJ/cm$^2$. Thus, depending upon the application, the power density necessary for UCL or for use with UCL materials is unlimited. With respect to biological systems, however, one of ordinary skill in the art will realize that lasers with high power densities, such as those with power densities of >100 mJ/cm$^2$, would create an increased risk of damage to host tissue or biomolecules. Whereas, this is not a problem by using the low power upconversion nanoparticles of the presently claimed and disclosed invention.

As mentioned previously, UCL materials that include a nanoparticle and a dopant may be particularly advantageous over UCL materials that include a bulk material and a dopant. One such doped-nanoparticle UCL material, $ZnS:Mn^{2+}$, has been mentioned hereinbefore with respect to power densities and will be discussed hereinafter in detail with respect to luminescence and temperature dependence experiments. One of ordinary skill in the art would appreciate, however, that doped-nanoparticle UCL materials as contemplate for use with the presently disclosed and claimed invention are not limited to $ZnS:Mn^{2+}$. Indeed, any compound of the general formula (X):(Y), wherein X is a host (e.g. a nanoparticle such as ZnS) and Y is a dopant (e.g. $Mn^{2+}$), is contemplated for use as a UCL material. One of ordinary skill in the art would, however, also appreciate that a doped nanoparticle of the general formula (X):(Y) would be the most advantageous for the reasons set forth hereinabove.

Any dopant capable of increasing the fluorescence intensity or quantum efficiency of the bulk material or nanoparticle is contemplated for use in the presently claimed and disclosed invention. With respect to semiconductor nanoparticles, such as ZnS, a dopant capable of increasing fluorescence intensity or quantum efficiency due to the increase of the oscillator strength and the efficient energy transfer from the host to the dopant upon photoexcitation is contemplated for use with the presently claimed and disclosed invention. The dopant also increases the fluorescence intensity or quantum efficiency of bulk materials in the same manner.

Typically such a dopant would have a high d-d transition rate—e.g. $Mn^{2+}$ has a d-d transition of $^4T_1 \to ^6A_1$. Thus, any dopant having a high d-d transition rate and that is also capable of increasing the luminescence intensity or quantum efficiency of the UCL material is contemplated for use in the presently claimed and disclosed invention. For example, but not by way of limitation, the dopants could be broadly classified as rare earth ions—e.g. $Tb^{3+}$, $Ce^{3+}$ or $Eu^{3+}$. The dopants may also be broadly classified, however, as transition ions—e.g. $Mn^{2+}$, $Cu^{2+}$, $Cu^+$, $Ag^+$, $Cr^{3+}$, $Ti^{2+}$, $Ni^{2+}$, or $Re^{4+}$. Thus, one of ordinary skill in the art would appreciate that the dopant must be functionally defined, rather than being strictly classified according to a position in the periodic table of elements. The dopant is herein defined and it is intended to include any material or ion that, when doped into a host material such as a nanoparticle, will increase the luminescence intensity or quantum efficiency of the porous material—thereby creating an efficient UCL material.

The dopant is placed substantially within a host—i.e. a bulk material or a nanoparticle. The host may be any type of material (i.e. semiconductor, non-conducting, insulating, or a conducting material). Functionally, the host must be capable of accepting the dopant and having a wide band gap. With respect to nanoparticles, exemplary nanoparticles for use as the host include: CdTe, CdSe, ZnO, CdS, ZnS, $Y_2O_3$, MgS, CaS, SrS and BaS. The host may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_{x-}Se_y$, $Pb_{1-x}Mn_xTe_y$, $Mg_{1-x}MnS_y$, $Ca_{1-x}Mn_xS_y$, $Ba_{1-x}Mn_xS_y$, and $Sr_{1-x}Mn_xS_y$, etc. (wherein, $0<x\leq1$, and $0<y\leq1$). Complex compounds of the above-described semiconductors are also contemplated for use in the presently claimed and disclosed invention—e.g. $(M_{1-z}N_z)_{1-x}Mn_xA_{1-y}B_y$(M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}SO_{0.8}Se_{0.2}$. Additional hosts include insulating and nonconducting materials such as $BaF_2$, BaFBr, and $BaTiO_3$, to name but a few exemplary compounds.

As described hereinabove, the UCL material of the present invention can be described generically by the formula (X):(Y) wherein (X) is a host and (Y) is a dopant capable of increasing the luminescence intensity or quantum efficiency of the host. The variables (X) and (Y) have been described individually heretofore, but when taken together and applied to a specific type of host—e.g. a semiconductor—preferred UCL materials would be transition and rare earth ion co-doped semiconductors. Such transition and rare earth ion co-doped semiconductors would include sulfide, telluride, selenide and oxide semiconductors and their nanoparticles, such as ZnS:Mn,Er; ZnSe:Mn,Er; MgS:Mn,ER; CaS:Mn,Er; ZnS:Mn,Yb; ZnSe: Mn,Yb; MgS:Mn,Yb; CaS:Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; R=at least one rare earth ion, $0<x\leq1$, $0<y\leq1$, $0<z\leq1$, $0<q\leq1$).

Thus, a UCL material capable of upconversion luminescence at low power (e.g. <10 mJ/cm$^2$) has been described such that one of ordinary skill in the art would be capable of making and using same. Further specific examples and resulting data are given hereinafter.

As mentioned previously, due to potential applications in lasers, laser cooling, optical communications, storage, displays, and imaging techniques, UCL has been extensively investigated. UCL is well documented in rare earth compounds in which the presence of more than one metastable excited f-f state results from the efficient shielding of the 4f electrons. Upconversion has been reported in some transition-metal compounds as well. $Mn^{2+}$ doped materials represent a class of phosphors that have already been utilized for many applications; however, no one has yet disclosed nor described the use of $Mn^{2+}$ (a dopant—(Y)) with a nanoparticle (host—(X)) for use as a UCL material.

Upconversion and anti-Stokes luminescence have been reported in semiconductor quantum dots, porous silicon, CdS nanoparticles, CdSe, and InP colloidal nanoparticles (P. P. Paskov et al., *Photoluminescence upconversion in InAs/GaAs self-assembled quantum dots*, Appl. Phys. Lett. 77, 812 (2000); L. A. Golovan et al., Observation of two-step excitation of photoluminescence in silicon nanostructures, Pisma Zh. Eksp. Teor. Fiz. 68, 732 (1998) @JETPLett. 68, 770 (1998)#; S. A. Blanton, M. A. Hines, M. E. Schmidt, and P. Guyot-Sionnest, *Two-photon spectroscopy and microscopy of II-VI semiconductor nanocrystals*, J. Lumin. 70, 253 (1996); E. Poles, D. C. Selmarten, O. I. Micc, and A. J. Nozik, *Anti-Stokes photoluminescence in colloidal semiconductor quantum dots*, Appl. Phys. Lett. 75, 971 (1999)). These previous results indicate that semiconductor nanoparticles may work as a new type of upconversion material; however, no one has demonstrated or disclosed the UCL of doped semiconductor nanoparticles.

EXPERIMENT

Details for Sample Preparation

Recipe for Nanoparticles in Methacrylic Acid/Citric Acid Matrix

In a four-neck flask, methacrylic acid (MA) (10 ml) and 2 g citric acid (CA) were mixed with ethanol (1000 mL, 99.95%) in a solution, then the solution was stirred while purging with $N_2$ for 2.5 hrs. Then a $Na_2S$ solution was added (8.009 g $Na_2S$ dissolved in 200 mL of 99.95% ethanol) and a mixed solution of $Zn^{2+}$ and $Mn^{2+}$ (30.337 g $Zn(NO_3)_2.6(H_2O)$ and 0.114 g $Mn(NO_3)_2$ dissolved in 200 mL 99.95% ethanol with the molar ratio of $Mn^{2+}:Zn^{2+}$ is 5:95) were added simultaneously with the same flowrate through two necks, respectively. The reaction was carried out under $N_2$ atmosphere at 80° C. for 24 hrs. A transparent colloid of ZnS:$Mn^{2+}$ was then obtained. The pH value of the final solution was 2.4. The nanoparticles were separated by centrifugation and dried in vacuum at room temperature.

Recipe for Un-Capped Nanoparticles.

The uncapped ZnS:Mn nanoparticles of 10 nm were prepared as follows: A four-neck flask was charged with 400 mL deionized water and was stirred under $N_2$ for 2.5 hrs. An aqueous solution of 1.6 g $Na_2S$ and an aqueous solution of 5.8 g $Zn(NO_3)_2.6(H_2O)$ and 0.26 g $Mn(NO_3)_2$ ($Mn^{2+}:Zn^{2+}$ molar ratio 5:95) were prepared and added to the first solution simultaneously via two different necks at the same rate. After the addition, the resulting solution was stirred constantly under $N_2$ at 80° C. for 24 hrs and a transparent colloid of ZnS:Mn was formed. The pH value of the final solution was 2.4. This relatively low pH value is required to prevent the precipitation of unwanted manganese species. The nanoparticles were separated from solution by centrifugation and dried in vacuum at room temperature.

Recipe for Nanoclusters in Zeolites

ZnS:$Mn^{2+}$ nanoparticles in the cavities of an ultra-stable zeolite-Y (USY) were prepared by solid state diffusion at high temperature. Typically, 100 mg of the uncapped ZnS:Mn nanoparticles (~10 nm in size) were mechanically mixed thoroughly with 2 g of USY powder (Si/Al ratio is 230), then the mixture was pressed into pellets. The pellets were then heated in a furnace at 900° C. in vacuum ($10^{-5}$ torr) for 4 hrs.

The preparation, structure, and the luminescence properties of the $Mn^{2+}$-doped ZnS (ZnS:$Mn^{2+}$) nanoparticles have been described previously. (See e.g. W. Chen et al., *Crystal field, Phonon coupling and emission shift of $Mn^{2+}$ in ZnS:Mn nanoparticles*, J. Appl. Phys. 89, 1120 (2001). W. Chen, A. G. Joly, and Z. Z. Zhang, *Upconversion luminescence of $Mn^{2+}$ in ZnS:$Mn^{2+}$ nanoparticles*, Phys. Rev. B 64, 41, 202 (2001). W. Chen, R. Sammynaiken, and Y. Huang, *Luminescence enhancement of ZnS:Mn nanoclusters in zeolite*, J. Appl. Phys. 88, 5188 (2000), each of which is incorporated herein in their entirety by reference).

Recipe for Making CdTe and CdTe:$Mn^{2+}$ Nanoparticles

The CdTe nanoparticles were prepared by a wet chemical technique which has been reported in literature (M. Kapitonov et al., *Luminescence properties of tiol-stabilized CdTe*

*nanocrystals*, J. Phys. Chem. B, 1999, 103:10109-10113 and W. Chen, D. Gronquist, and J. Roark, *Voltage tunable electroluminecsnce of CdTe nanoparticle light-emitting diodes*, J. Nanosci. Nanotechnol., 2002, 2: 47-53). Cadmium perchlorate hydrate (Aldrich), aluminum telluride (99.5% pure, Gerac), and thioglycolic (mercaptoacetic) acid (Aldrich) were used as received. CdTe nanoparticles were prepared by the rapid mixing of precursors containing cadmium perchlorate hydrate and sodium hydrotelluride (NaHTe), cooled to 5° C., under vigorous stirring. The $Cd^{2+}$ containing solution was prepared as follows: 0.73 g. of $Cd(ClO_4)_2.H_2O$ was dissolved in 125 mL of water. 0.3 mL of thioglycolic acid (TGA) was added to the solution and its pH was adjusted to ~11.2 by the addition of 0.1M NaOH. The solution was then purged with nitrogen for at least 30 minutes. The solution of NaHTe was prepared in a vessel cooled with water ice to 5° C., by bubbling an excess of $H_2Te$ through 22 mL of 0.05 M NaOH for 40 minutes under nitrogen. The hydrogen telluride gas was obtained from the reaction of excessive amounts of $Al_2Te_3$ and 0.5 M $H_2SO_4$ in an inert atmosphere (nitrogen). Great care was taken to keep the NaHTe solution temperature at an average of 5° C., as well as to avoid any contact of the solutions involved with oxygen (air) at all times.

After the completion of the reaction, a yellow solution of CdTe nanocrystal nuclei was obtained. This solution was then refluxed at 100° C. to promote crystal growth. The size of the particles was controlled by the reaction time. The size of the nanoparticles created was around 4 nm as observed by high resolution transmission electron microscope (HRTEM). Most nanoparticle are spherical in shape, while some of them are nonspherical. The [1, 1, 1] lattice strings can be seen from the HRTEM images, and the spacing found is about 0.36 nm, which is in agreement with the [1, 1, 1] spacing of cubic CdTe of 0.374 nm.

The recipe for making $CdTe:Mn^{2+}$ nanoparticles is the same as that for CdTe nanoparticles, while, a calculated amount of $Mn(ClO_4)_2.H_2O$ was dissolved in water along with a calculated amount of $Cd(ClO_4)_2.H_2O$.

Recipe for Making CdS Nanoparticles in $BaTiO_3$

Formation of $CdS/BaTiO_3$ nanostructured materials: Ba—Ti complex alkoxide solution and CdS colloidal solution were prepared separately, and mixed together to form the composite precursor solution. To make Ba—Ti complex alkoxide solution, barium ethanoxide solution, prepared by dissolving metal barium into ethanol, and titanium isopropanide solution in 2-methoxyethanol were mixed and stirred for a few hrs. CdS colloidal solution was prepared by a selinazation process of $Cd(NO_3)_2$ and $H_2S$ flux in 2-methoxyethanol with existence of N,N-dimethlyformamide. The particle size can be controlled by the concentration of $Cd(NO_3)_2$ and N,N-dimethlyformamide. The colloid solution as prepared was added to the alkoxide solution with molar ratio of Cd/Ba=0.02, then a clear composite precursor solution was obtained. Thin films may be prepared by spin coating with the fresh precursor solution, and then dried at 100° C. in air, heat treated at 200-800° C. in $N_2$ atmosphere.

Recipe for Making $ZnS:Eu^{2+}$ and $ZnS:Eu^{3+}$ Nanoparticles

The $ZnS:Eu^{2+}$ nanoparticles were prepared in a water-ethanol solution as follows: In a four-neck flask, the water-ethanol solution (500 mL water and 500 mL 99.95% ethanol) was stirred while purging with $N_2$ for 2.5 hrs, then a $Na_2S$ solution was added (8.009 g $Na_2S$ dissolved in 100 mL 99.95% ethanol and 100 mL deionized water) and a mixed solution of $Zn^{2+}$ and $Eu^{2+}$ (30.337 g $Zn(NO_3)_2.6(H_2O)$ and 0.114 g $EuCl_2$ dissolved in a mixture of 150 mL 99.95% ethanol and 50 mL deionized water) were added at the same time with the same speed through two necks, respectively. The reaction was carried out in a $N_2$ atmosphere at 80° C. for 24 hrs. Then a transparent colloid of $ZnS:Eu^{2+}$ was then obtained. The nanoparticles were separated by centrifugation and dried in vacuum at room temperature. The pH value of the final solution is 2.4, which prevents precipitation of other Eu species outside the particles in the same manner as reported for $Mn^{2+}$ doped ZnS nanoparticles.

The recipe for making $ZnS:Eu^{3+}$ nanoparticles is similar to that for $ZnS:Eu^{2+}$ nanoparticles. Just two different points are: it is $Eu(NO)_3$ rather than $EuCl_2$ that provides $Eu^{3+}$; the reaction is conducted in air not in a $N_2$ atmosphere.

Recipe for Making $ZnS:Ag^+$ Nanoparticles

A four-neck flask is charged with a solution containing 10 mL methacrylic acid and 400 mL ethanol (99.95% Sigma). The solution is stirred under $N_2$ for 2.5 hrs. A second solution containing 1.6 g of $Na_2S$ and 100 mL of ethanol and a third solution containing 5.8 g of $Zn(NO_3)_2.6(H_2O)$, 0.22 g of $AgNO_3$, and 100 mL of ethanol ($Ag^+:Zn^{2+}$ molar ratio 5:95) are prepared and added to the first solution simultaneously via two different necks at the same rate. After this addition, the resulting solution is stirred constantly under $N_2$ at 80° C. for 24 hrs. so that a transparent colloid of $ZnS:Ag^+$ is formed. The pH value of the final solution is 3.0. This relatively low pH value is required to prevent the precipitation of unwanted Ag species from occurring.

Recipe for Making $ZnS:Cu^+$ Nanoparticles

A four-neck flask is charged with a solution containing 10 mL methacrylic acid and 400 mL ethanol (99.95%). The solution is stirred under $N_2$ for 2.5 hrs. A second solution containing 1.6 g of $Na_2S$ and 100 mL of ethanol and a third solution containing 5.8 g of $Zn(NO_3)_2.6(H_2O)$, 0.26 g of $CuNO_3$, and 100 mL of ethanol are prepared and added to the first solution simultaneously via two different necks at the same rate. After this addition, the resulting solution is stirred constantly under $N_2$ at 80° C. for 24 hrs. so that a transparent colloid of $ZnS:Cu^+$ is formed. The pH value of the final solution is 2.4 This relatively low pH value is required to prevent the precipitation of unwanted Cu species from occurring.

Recipe for Making $Y_2O_3:Tb^{3+}$, $Eu^{3+}$ Nanoparticles

Solution (A) was prepared by dissolving 15.78 g of $Y(NO_3)_3.5H_2O$, 0.250 g of $Eu(NO_3)_3$ and 0.350 g of $Tb(NO_3)_3$ in ethanol. The solution was stirred for 2 hrs at room temperature. Solution (B) was prepared by dissolving 0.25 mL of tween-80 poly-oxyethylene sorbitate and 0.25 mL of emulson-OG (oelsauerepolyglyscerinester) in 50 mL of aqueous ammonium hydroxode solution (pH>10) and stirred for 1hrs. at room temperature. Solution (A) was then added to solution (B) drop by drop through a burette at a controlled rate with vigorous stirring. The obtained gel was separated in a centrifuge. The aqueous solution was removed by refluxing in toluene using a water trap. The toluene was removed by evaporation, and the resulting powder was dried in the oven at 60° C. for 24 h. The final products may be isolated as white powders of different sizes after heat treatment in a tube furnace at different temperatures for 2 hrs. in ambient atmosphere.

Recipe for Making $BaFBr:Eu^{3+}$ and $BaFBr:Eu^{2+}$ Nanoparticles.

The preparation of $BaFBr:Eu^{2+}$ nanoparticles is based on the following reaction in acid solutions: $BaBr_2 + NH_4F \leftrightarrows BaFBr + NH_4Br$. In order to control the reaction rate, stabilizers (polyvinyl alcohol, Sigma) were added to the solution to control the reaction temperature. In our experience, we found the following recipe can successfully make BaFBr:Eu nanoparticles: (1) A four-neck flask was charged with 400 mL deionized water and 4 g polyvinyl alcohol and was stirred under $N_2$ for 1 hr. The pH value was adjusted to 2 by nitrate acid. (2) 4.83 g $BaBr_2 \cdot 2H_2O$ and 0.137 g $EuI_2$ were added to the solution and stirred under $N_2$ for 1 hr at room temperature. (3) 0.70 g NaF was added to the solution and stirred under $N_2$ for 0.5 hr at room temperature until precipitation occurred. (4) The temperature was raised to 80° C., the reaction was sustained for 2 hrs. and then, cooled rapidly to room temperature. (5) The nanoparticles were separated from solution by centrifugation, washed with dionized water, and dried in vacuum at room temperature. (6) The powder was heated at a temperature lower than 450° C. in a carbon monoxide or $N_2$ atmosphere for 0.5 hr.

Recipe for Making BaFBr:$Eu^{2+}$ nanoparticles in MCM-41 and Zeolites

For making BaFBr:$Eu^{2+}$ nanoparticles in MCM-41, bulk BaFBr:$Eu^{2+}$ powder was made by solid state diffusion at 800° C. for 2 hrs. Then, BaFBr:$Eu^{2+}$ powder and MCM-41 powder (ratio of BaFBr:$Eu^{2+}$/MCM-41 is 5:95) were mixed up and heated at 600° C. under $N_2$ for 2 hrs. The recipe for BaFBr:$Eu^{3+}$ is the same but reaction was conducted in air rather than in $N_2$ atmosphere.

Details for Measurements

The average sizes of the ZnS:$Mn^{2+}$ particles used in the following experiments, estimated from high-resolution transmission electron microscope (HRTEM) and x-ray diffraction, are approximately 1, 3, 3.5, 4.5, and 10 nm. The 1 nm-sized ZnS:$Mn^{2+}$ nanoparticles are encapsulated in an ultrastable zeolite-Y (USY), while the 10 nm-sized nanoparticles are naked particles without any capping. The 3-, 3.5-, and 4.5 nm-sized particles were capped with methacrylic acid:citric acid. The size was controlled by the ratio of methacrylic acid:citric acid and by the reaction temperatures.

The photoluminescence and upconversion emission spectra and lifetime data were collected using a nanosecond optical parametric oscillator/amplifier (Spectra-Physics MOPO-730) operating at a 10-Hz repetition rate and tunable between 440 and 1800 nm. The output of the MOPO system was either frequency doubled in a potassium dihydrogen phosphate crystal for observation of the photoluminescence emission or else used directly for the upconversion measurements.

The output was directed onto the particles and emission was collected at right angles to the excitation and focused into a ⅛ meter monochromator with either a gated intensified charge coupled device detector (for emission spectra) or else a standard photo multiplier tube (for lifetime measurement). Fluorescence spectra shown in this study were collected approximately 5 μs after excitation, with a gate width of 20 μs. For lifetime measurements the output of the photo multiplier tube was directed into a digital oscilloscope with the input impedance adjusted to give a system response time of about 2 μs full width at half maximum. While fluorescence was observed on faster timescales, it has been shown previously (B. A. Smith, J. Z. Zhang, A. Joly, and J. Liu, *Luminescence decay kinetics of $Mn^{2+}$-doped Zns nanoclusters grown in reverse micelles*, Phys. Rev. B 62, $20^{2+}$ (2000)) that much of this is emission from the ZnS itself and so was not of interest. All lifetime data reported herein were measured at or near the peak emission wavelength with a monochromator bandwidth of several nanometers. Power dependences were measured as a function of excitation energy by integrating the area of the $Mn^{2+}$ emission from about 530 to 630 nm as a function of excitation power. Power levels were adjusted with a variable attenuator, measured with a power meter, and then in some cases reduced by up to five orders of magnitude using neutral density filters in order to prevent saturation effects from distorting the measurement. Due to the fact that different detector gain levels were employed and different amounts of attenuation were used after the power measurement, no comparison of the absolute intensities between different samples can be made.

Results and Discussion

FIG. 1 shows the photoluminescence (excited at 300 nm) and upconversion (excited at 767 nm) emission spectra of the ZnS:$Mn^{2+}$ nanoparticles. For comparison, the upconversion emission spectrum of bulk ZnS:$Mn^{2+}$ is also shown. The broad emission is from the $^4T_1 \rightarrow ^6A_1$ transition of $Mn^{2+}$. It can be seen that the $Mn^{2+}$ $^4T_1 \rightarrow ^6A_1$ emission maximum is shifted with particle size, a result that has been discussed in W. Chen, R. Sammynaiken, and Y. Huang, *Luminescence enhancement of ZnS:Mn nanoclusters in zeolite*, J. Appl. Phys. 88, 5188 (2000); W. Chen, X. H. Zhang, and Y. Huang, *Luminescence enhancement of EuS nanoclusters in zeolite*, Appl. Phys. Lett., 2000, 24, 2328-2330. In order to see the difference between the photoluminescence and the upconversion emissions, in each sample the two spectra are normalized. FIG. 1 clearly shows that for the bulk and the 1 nm-sized ZnS:$Mn^{2+}$ particles encapsulated in USY, the upconversion emission spectra are almost identical with the photoluminescence emission spectra. However, for the 3-, 3.5-, 4.5-, and 10 nm sized nanoparticles, the upconversion emission maxima are approximately 7.5-, 9-, 6-, and 4 nm redshifted from their photoluminescence emission maxima, respectively.

Figure 2:
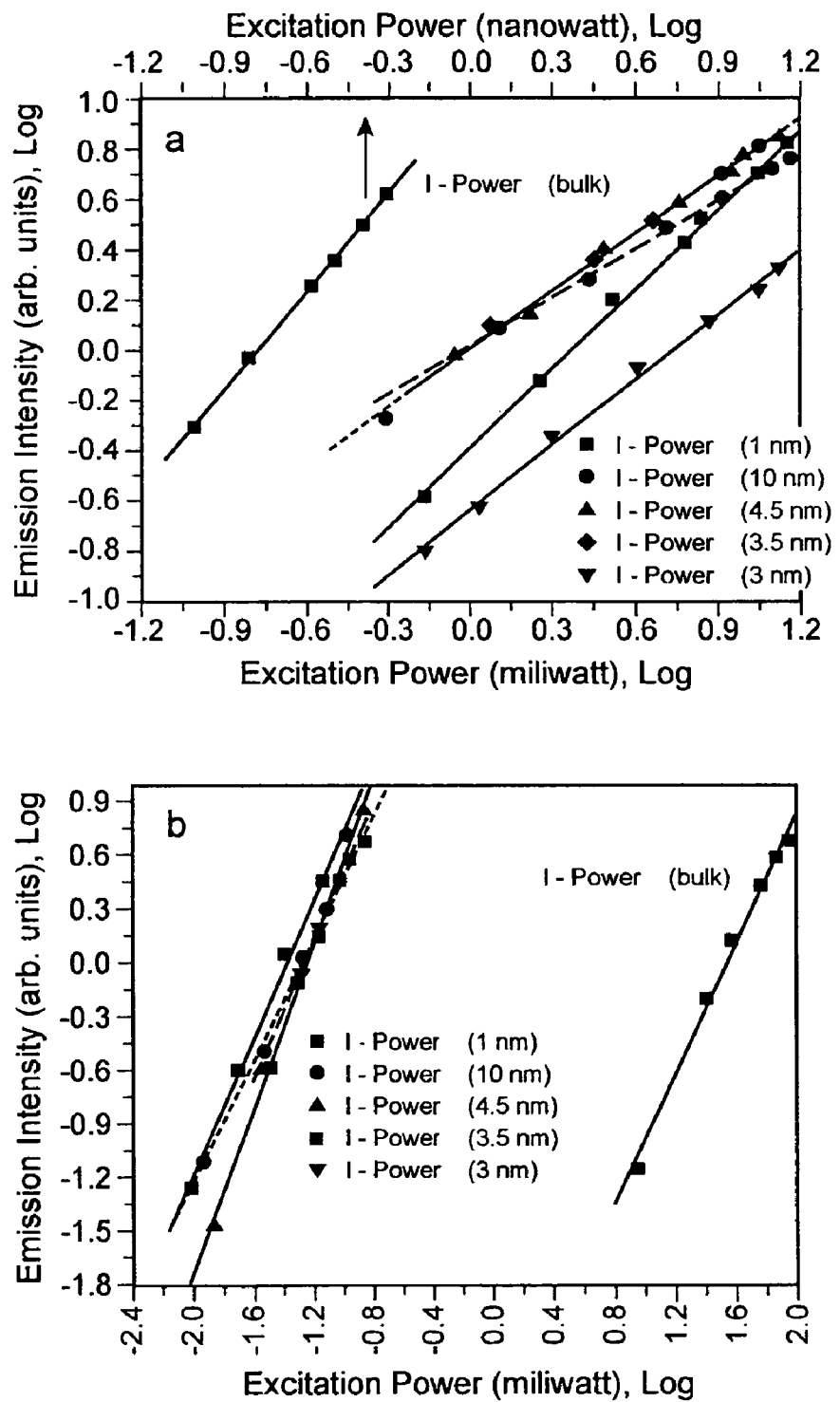
FIG. 2 is a graphical representation of the power dependence of photoluminescence (a) and upconversion luminescence (b) of Mn$^{2+}$ in bulk ZnS:Mn$^{2+}$ and nanoparticles. Results shown indicate that the photoluminescence intensity depends linearly on the excitation power whereas the upconversion luminescence intensity varies quadratically with excitation power. Bulk ZnS:Mn$^{2+}$ photoluminescence intensity is plotted versus the upper horizontal axis while the nanoparticle photoluminescence intensity is plotted versus the lower axis.

FIG. 2 shows the excitation power dependence of the photoluminescence and upconversion luminescence intensities of ZnS:$Mn^{2+}$ nanoparticles and bulk ZnS:$Mn^{2+}$. The photoluminescence intensity increases linearly with the excitation power with the linear constants between 0.8 and 1.1 for the nanoparticles, and 1.3 for the bulk. The power dependence of the upconversion luminescence intensity on the excitation density is quadratic, I~$Power^K$, where K is between 1.8 and 2.1. This indicates that a second-order process, such as two-photon absorption or an Auger recombination process, is responsible for the upconversion luminescence.

Figure 3:
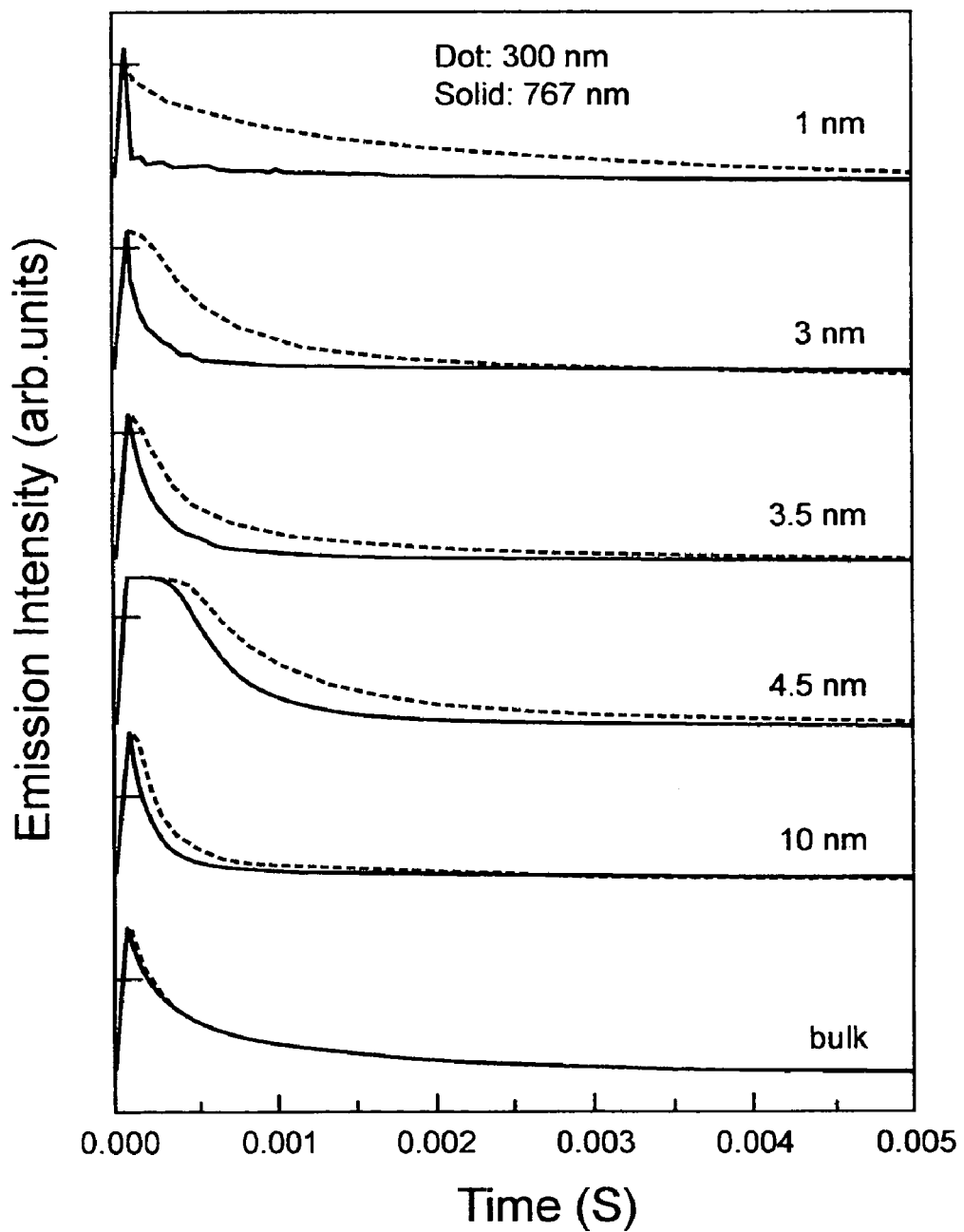
FIG. 3 is a graphical representation of the time decays of photoluminescence (dot, excitation at 300 nm) and upconversion (solid, excitation at 767 nm) luminescence of Mn$^{2+}$ in ZnS:Mn$^{2+}$ bulk and nanoparticles. The emission lifetime of the photoluminescence excited at 300 nm is longer than the upconversion lifetime excited at 767 nm.

FIG. 3 shows the lifetime decay curves of the photoluminescence excited at 300 nm and upconversion luminescence excited at 767 nm. It is interesting to note that the upconversion decay lifetimes are shorter than the corresponding photoluminescence decay lifetimes. Similar observations and findings have not been demonstrated and/or disclosed by anyone of skill in the art previously.

Both Auger recombination and two-photon absorption can result in a quadratic dependence of the luminescence intensity on the excitation power. Auger recombination is a process in which an electron recombines with a hole and transfers the excess energy immediately to another electron or hole. The recombination of the high-energy electron or hole with another hole or electron is responsible for the upconversion. The efficiency of Auger recombination is mediated by Coulomb electron-electron interaction. In nanoparticles, the Coulomb interactions are enhanced due to size confinement. This leads to increased Auger rates in comparison with those in bulk materials. In contrast, the discrete energy-level structure in nanoparticles necessarily limits the density of final states that satisfy energy conservation so that Auger processes should be less likely unless participation of phonons or energy states outside the nanoparticle occurs coincidentally. Experimentally, it has been observed that Auger recombination occurs only at very high excitation density. (F. Wu, J. Z.

Zhang, R. Kho, and R. K. Mehra, *Radiative and nonradiative lifetimes of band edge states and deep trap states of CdS nanoparticles determined by time-correlated single photon counting*, Chem. Phys. Lett. 330, 237 (2000)). In our measurements presented herein, the laser excitation density is lower than that normally required for Auger processes. Furthermore, it has been shown in both theoretical predictions and experimental observations that the change in upconversion luminescence intensity from Auger recombination with temperature is slower than that of the Stokes photoluminescence. In the present experiments and resulting data, the upconversion luminescence intensity is even more sensitive to temperature than that of the Stokes photoluminescence. This indicates that the upconversion luminescence is not likely to be caused by Auger processes. Therefore, it is reasonable to conclude that the upconversion luminescence of $Mn^{2+}$ in $ZnS:Mn^{2+}$ nanoparticles and bulk is due to a two-photon absorption process.

Figure 4:
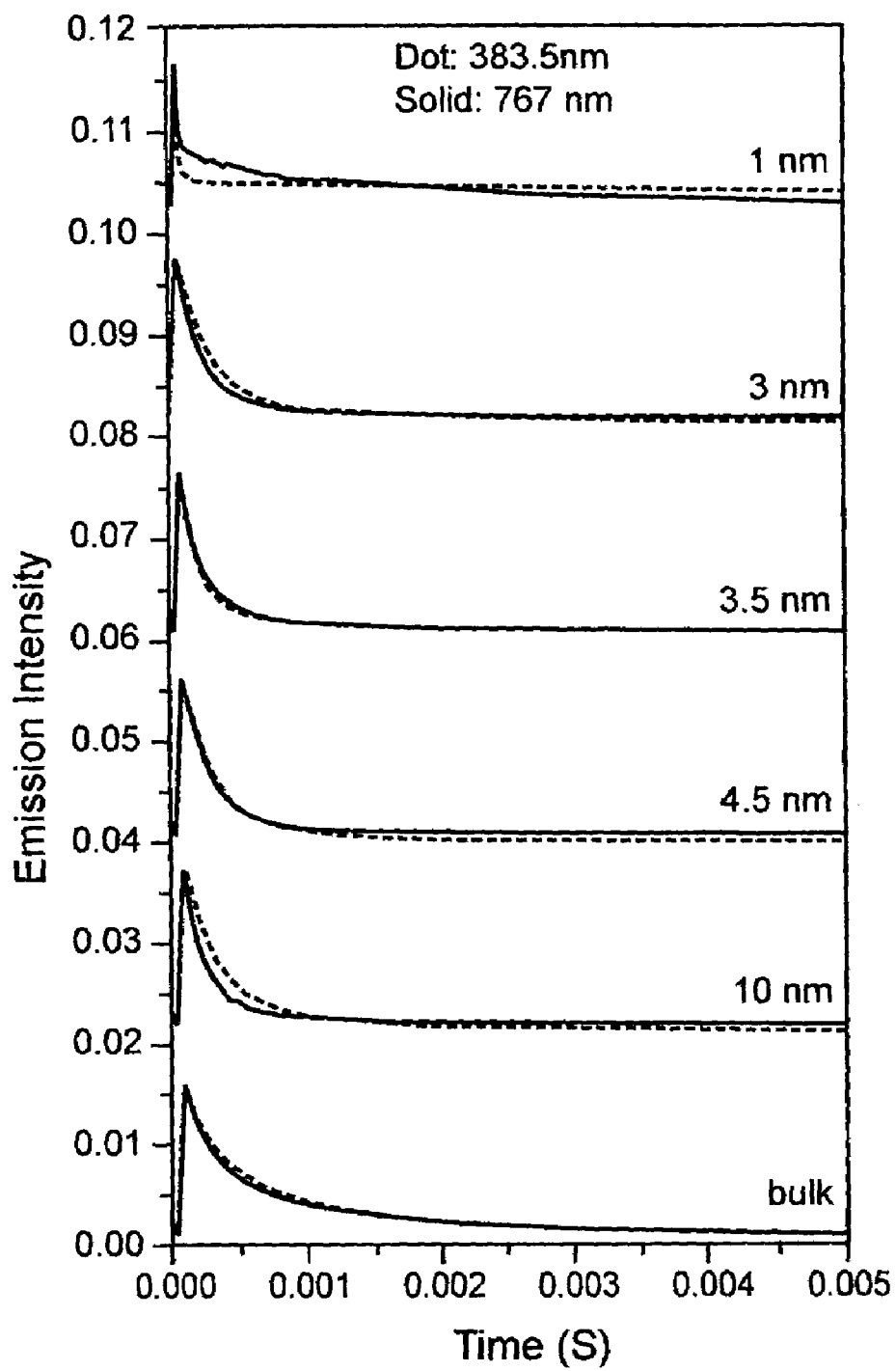
FIG. 4 is a graphical representation of photoluminescence (dot, excitation at 383.5 nm) and upconversion (solid, excitation at 767 nm) luminescence of Mn$^{2+}$ in ZnS:Mn$^{2+}$ bulk and nanoparticles. In contrast to photoluminescence resulting from excitation at 300 nm, here the photoluminescence lifetimes are almost identical with the upconversion lifetimes.

In order to confirm the two-photon process, we measured the emission spectra and decay lifetimes with single photon energy (383.5 nm) which is the sum energy of two photons at 767 nm. The emission spectra and lifetimes obtained at 383.5 nm excitation should be the same as that at 767 nm excitation if the upconversion luminescence is due to two-photon excitation, because the excitation energies are actually the same in this case. If the upconversion luminescence is due to Auger processes, the spectra and lifetimes excited at 383.5 nm are not expected to be the same as those at 767 nm excitation, because the two energies are not the same. The present experiments and results demonstrate that the emission spectra and lifetimes excited at 383.5 nm are almost identical as those obtained at 767 nm excitation (FIGS. 1 and 4). Thus, upconversion luminescence is derived from a two-photon absorption process.

As revealed by electron spin resonance (ESR), $Mn^{2+}$ can occupy two sites in $ZnS:Mn^{2+}$ nanoparticles: the lattice sites of $Zn^{2+}$ ions and the near-surface sites. (W. Chen et al., *Crystal field, Phonon coupling and emission shift of $Mn^{2+}$ in ZnS:Mn nanoparticles*, J. Appl. Phys. 89, 1120 (2001). And W. Chen, R. Sammynaiken, and Y. Huang, *Luminescence enhancement of ZnS:Mn nanoclusters in zeolite*, J. Appl. Phys. 88, 5188 (2000)) These different sites should display different emission spectra and decay lifetimes. In the nanoparticles, the upconversion and the 383.5 nm excited photoluminescence emission maxima shift to lower energies in comparison with the photoluminescence energy when excited at 300 nm, and their decay lifetimes are shorter than the lifetimes obtained with 300 nm excitation. This could be due to site-selected excitation of $Mn^{2+}$ ions or size-selected excitation of the nanoparticles. Based on the data obtained, we attribute the upconversion emission and the photoluminescence emission excited at 383.5 nm to the $Mn^{2+}$ at the near-surface sites. The $Mn^{2+}$ ions at the near surface sites have a faster decay lifetime and a lower emission energy than the $Mn^{2+}$ ions at the bulk-like lattice sites.

One reason is that the symmetry of the near-surface sites is lower than the lattice sites. The excited levels of $Mn^{2+}$ are split in the near-surface sites due to the change in the crystal field symmetry. The lowest emitting state will shift to a lower energy position, and thus the emission energy is shifted to longer wavelengths. Due to the change in the crystal field symmetry, the transition property of the emitting state is also changed, from forbidden to allowed or partly allowed. This is one reason why the upconversion and the 383.5 nm excitation decay lifetimes are shorter than the 300 nm excitation lifetimes. Another reason is that the coupling of the surface carriers to the near-surface site $Mn^{2+}$ ions is stronger than to the lattice site $Mn^{2+}$ ions. Thus more surface carriers are involved in the luminescence process of the near-surface site $Mn^{2+}$ ions. This also may shift the emission to lower energies and shorten the decay lifetime. This is the first demonstration of distinguished emission from the two different sites of $Mn^{2+}$ in $ZnS:Mn^{2+}$ nanoparticles.

In bulk $ZnS:Mn^{2+}$, all $Mn^{2+}$ ions occupy the lattice sites and, therefore, no difference in emission energy or in lifetime is observed at different excitation wavelengths. By contrast, in the 1 nm-sized $ZnS:Mn^{2+}$ particles encapsulated in zeolite-USY, almost all $Mn^{2+}$ ions are at the near-surface sites as revealed by ESR, with little difference in the emission energy observed for different excitation wavelengths. In addition, the particle surface is extremely well passivated by encapsulation into the zeolite cavities at 900° C. Thus, the luminescence kinetics (decay lifetime) and temperature dependence of the 1-nm sample are different from that of other nanoparticles, as will be discussed in more detail hereinbelow.

In summary, upconversion luminescence of $Mn^{2+}$ is observed in $ZnS:Mn^{2+}$ bulk and nanoparticles. Based on the power dependence, the lifetime measurements, and spectra at different excitation wavelengths, the upconversion luminescence of $Mn^{2+}$ in $ZnS:Mn^{2+}$ is attributed to a two-photon absorption process. In nanoparticles, the redshift in the emission energy and the shortening in the lifetimes of the upconversion luminescence and the photoluminescence excited at 383.5 nm in comparison with the photoluminescence excited at 300 nm are attributed to site-selected excitation of $Mn^{2+}$ ions in the nanoparticles. $Mn^{2+}$ ions at the nearsurface sites are responsible for the upconversion emission and the luminescence following 383.5 nm excitation, while $Mn^{2+}$ ions in the bulklike lattice sites are excited in the luminescence resulting from 300 nm excitation. Our results demonstrate that doped nanoparticles are a new type of material that display strong upconversion luminescence, and upconversion luminescence is an effective tool that can reveal the intrinsic properties of the dopants in doped nanoparticles.

Optical properties of semiconductor nanoparticles have been studied extensively in recent years. (N. S. Nalwa, Editor, *Handbook of Nanostructured Materials and Nanotechnology*, Academic Press, San Diego (2000), Vol. 4). Due to quantum confinement effects, large surface-to-volume ratios, and geometrical confinement of phonons, semiconductor nanoparticles behave differently from the bulk materials and therefore have novel properties. Size confinement effects lead to increased overlap between electron and hole wave functions, and decrease the density of both electronic and phonon states, resulting in different relaxation rates following electronic excitation relative to their bulk counterparts. Similarly, the increased surface-to-volume ratio necessarily allows an increase in the density of surface states, the influence of which on the energy transfer dynamics and luminescence intensity must be considered.

Doped nanoparticles represent a class of materials that have novel properties that may allow more flexibility when designing application devices, discussed in more detail hereinbelow. Indeed, $Mn^{2+}$ doped materials already have found uses as phosphors in many applications. In particular, $Mn^{2+}$ doped ZnS ($ZnS:Mn^{2+}$) is of much interest because it is widely used in electroluminescence and cathodoluminescence displays. Since the report of significant emission lifetime shortening in $ZnS:Mn^{2+}$ nanoparticles, (R. N. Bhargava, D. Gallagher, X. Hong and A. Nurmikko, *Optical properties of Manganese-doped nanocrystals of ZnS*, Phys. Rev. Lett. (1994), 72, 416) many articles on doped metal chalcogenide quantum dots have appeared, including topics such as new preparation methods, luminescence properties, and potential applications. In the field of doped nanoparticles, perhaps the most fundamentally interesting results are the luminescence enhancement and the lifetime shortening of $Mn^{2+}$ emission from milliseconds in bulk to nanoseconds in $ZnS:Mn^{2+}$ nanocrystals reported by R. N. Bhargava, D. Gallagher, X. Hong and A. Nurmikko, *Optical properties of Manganese-doped nanocrystals of ZnS*, Phys. Rev. Lett. (1994), 72, 416. However, A. A. Bol and A. Meijerink, *Long-lived $Mn^{2+}$ emission in nanocrystalline $ZnS:Mn^{2+}$*, Phys. Rev. B 56, R15997 (1998), N. Murase et al., *Fluorescence and EPR characteristics of $Mn^{2+}$-doped ZnS nanocrystals prepared by aqueous colloidal method*, J. Phys. Chem. B 103, 754 (1999), and B. A. Smith, J. Z. Zhang, A. Joly, and J. Liu, *Luminescence decay kinetics of $Mn^{2+}$-doped Zns nanoclusters grown in reverse micelles*, Phys. Rev. B 62, $20^{2+}$ (2000) later found that the $Mn^{2+}$ emission in ZnS nanoparticles does not show a spectacular shortening of the decay time, but rather has the same decay as in bulk. The nanosecond decay time of $Mn^{2+}$ emission reported by R. N. Bhargava, D. Gallagher, X. Hong and A. Nurmikko, *Optical properties of Manganese-doped nanocrystals of ZnS*, Phys. Rev. Lett. (1994), 72, 416 was interpreted as the tail of a broad, defect-related ZnS emission. Despite the controversy surrounding the lifetime shortening and its possible mechanisms, the luminescence enhancement reported in R. N. Bhargava, D. Gallagher, X. Hong and A. Nurmikko, *Optical properties of Manganese-doped nanocrystals of ZnS*, Phys. Rev. Lett. (1994), 72, 416, has been observed by other groups.

Hereinabove, experiments and results were given that show that $ZnS:Mn^{2+}$ nanoparticles display strong upconversion luminescence. Power dependences and lifetime measurements from multiwavelength excitation of both the photoluminescence and upconversion luminescence reveal that the mechanism for this strong upconversion is a two-photon absorption process. Upconversion luminescence is an effective method for distinguishing emissions from $Mn^{2+}$ at different sites in the nanoparticles. The following experiments expand upon those outlined hereinabove and include the temperature dependence of the emission wavelength, and the emission intensity of both the photoluminescence and upconversion luminescence.

Temperature Dependence of Photoluminescence and Upconversion Luminescence

Experimental

The preparation, structure, and fluorescence properties of $Mn^{2+}$ doped ZnS nanoparticles have been described previously, hereinabove. The photoluminescence and upconversion emission spectra at different temperatures were measured by mounting the samples on the cold finger of a liquid helium flow-through cryostat using indium metal for thermal contact. The cold finger was equipped with a heater element and the temperature was controlled via a Lakeshore Model 330 temperature controller that monitored the temperature via a calibrated silicon diode attached to the indium metal at the sample position. Emission spectra were measured using a constant laser power density at several different temperatures between 8 and 273 K, and the integrated area of the broad $Mn^{2+}$ emission was used to calculate the intensity at a specific temperature.

Temperature Dependence of the Emission Wavelength

The details of the upconversion luminescence of $ZnS:Mn^{2+}$ were outlined hereinabove, but in brief, the strong upconversion luminescence observed in $ZnS:Mn^{2+}$ nanoparticles is visible to the naked eye. The upconversion luminescence was recorded at a laser power density of 100 $mJ/cm^2$, but it was detectable at a power density of 1 $mJ/cm^2$. The upconversion emission band excited at 767 nm is red shifted from the photoluminescence emission excited at 300 nm for the nanoparticles prepared in the organic matrix. However, no shift is observed in the bulk or in the particles encapsulated in zeolite-USY. In the nanoparticles, the decay lifetimes of the upconversion emission excited at 767 nm are shorter than the 300 nm excited luminescence lifetimes, whereas in bulk the two decays are almost identical. When the photoluminescence is obtained by excitation at 383.5 nm, which is the sum energy of two photons at 767 nm, the emission spectra and the lifetimes of the two types of luminescence are almost identical.

The power dependence of the photoluminescence is linear, whereas that of the upconversion emission is quadratic. Based on these observations, two-photon excitation is responsible for the upconversion luminescence of $Mn^{2+}$ in $ZnS:Mn^{2+}$ nanoparticles. This conclusion is supported by the temperature dependences of the upconversion and the photoluminescence that are reported hereinafter.

Figure 5:
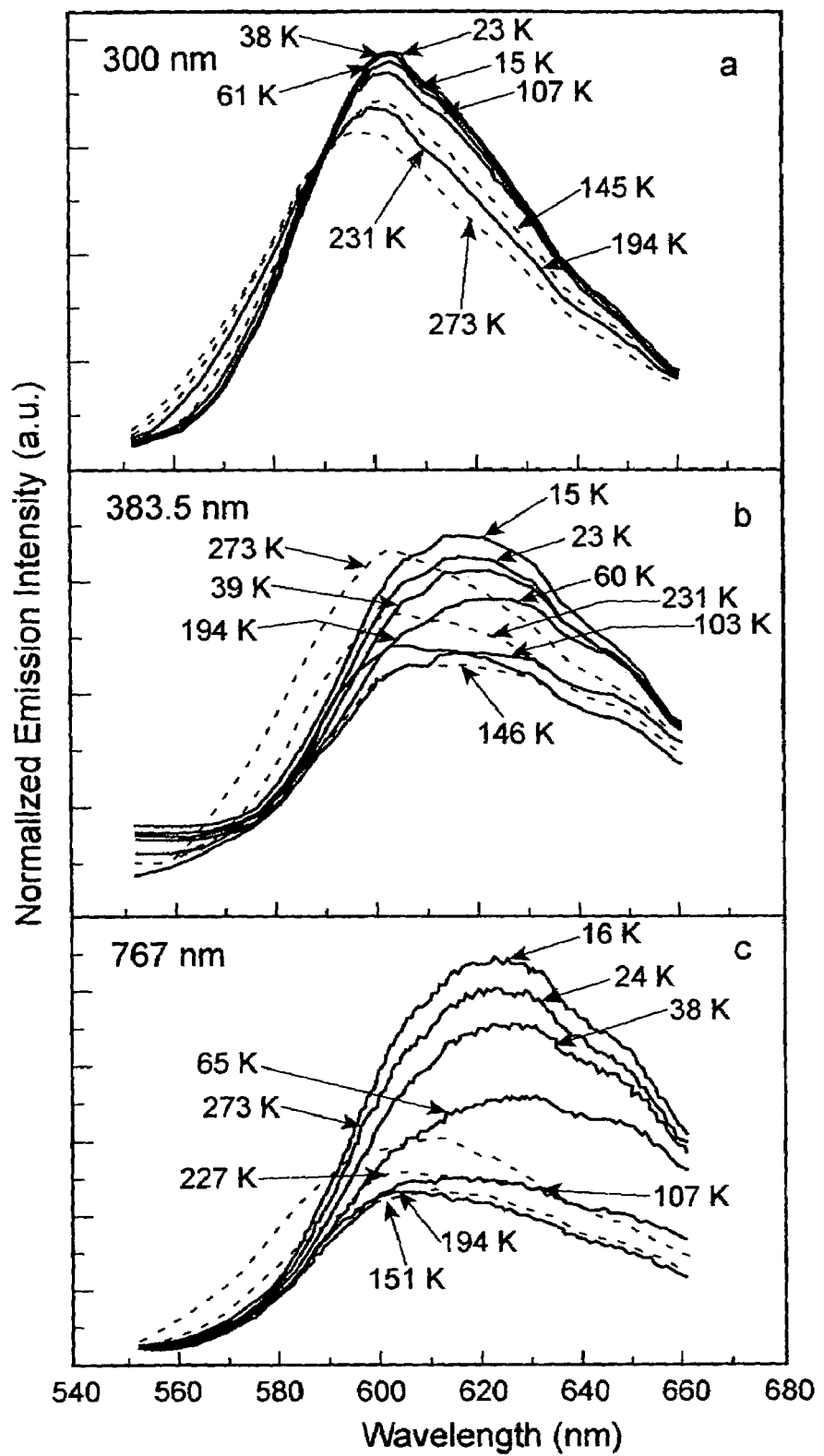
FIG. 5 is a graphical representation of the emission spectra of Mn$^{2+}$ in the 3.5 nm sized ZnS:Mn$^{2+}$ nanoparticles excited at (a) 300 nm and (b) 383.5 nm, and (c) upconversion luminescence following 767 nm excitation at differing temperatures.
Figure 6:
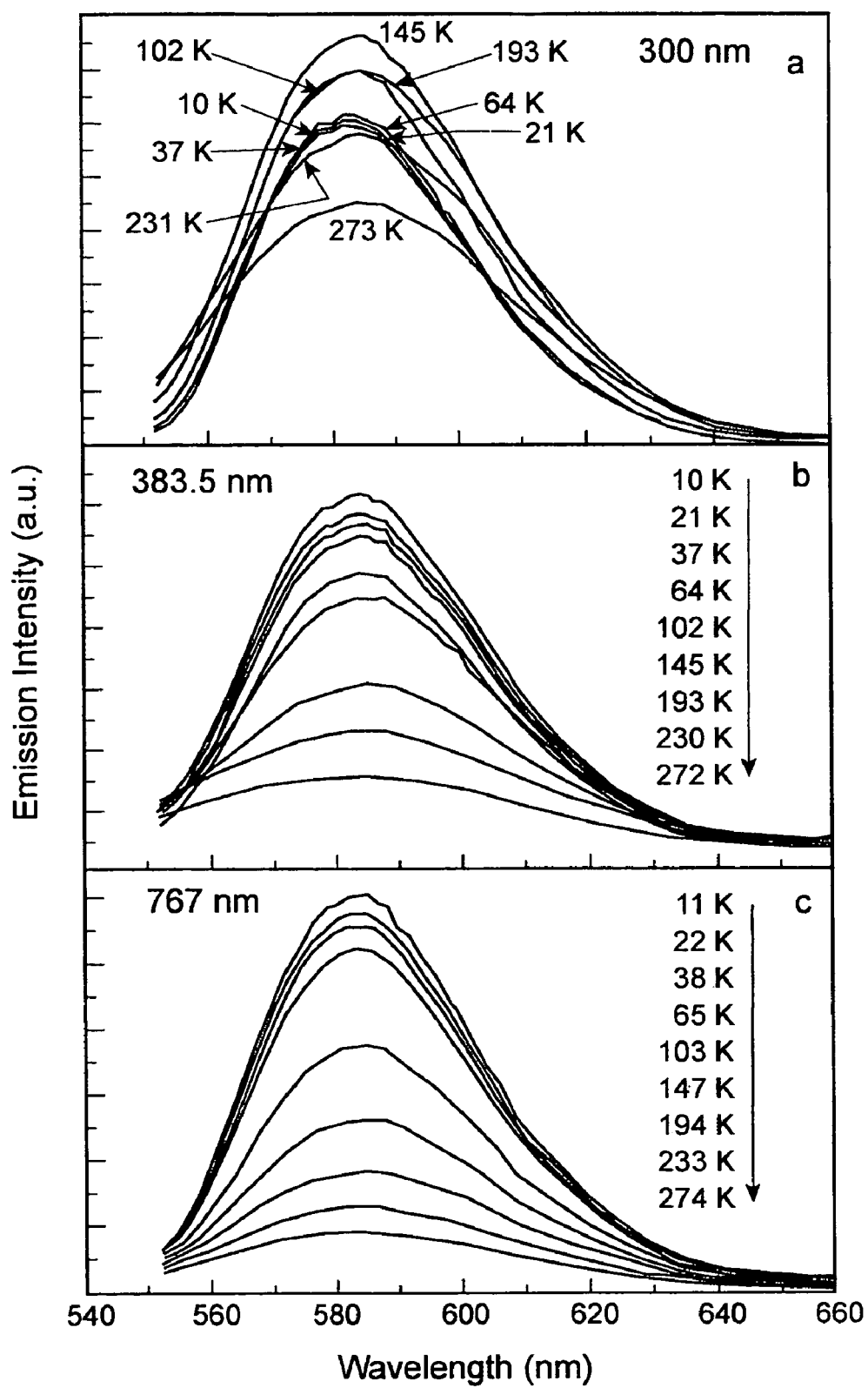
FIG. 6 is a graphical representation of the emission spectra of Mn$^{2+}$ in ZnS:Mn$^{2+}$/USY (i.e. the ZnS:Mn$^{2+}$ is placed within the cavities of the USY zeolite for the purpose of stabilizing the doped nanoparticle) excited at (a) 300 nm and (b) 383.5 nm, and (c) upconversion luminescence induced by 767 nm excitation at differing temperatures.

In the particles prepared in MA and CA, the particle sizes are 3-5 nm, and $Mn^{2+}$ ions occupy both the near-surface sites and the bulk lattice sites. A representative temperature dependence of the photoluminescence and upconversion luminescence of this type of nanoparticle is shown in FIG. 5 for the 3.5 nm sized particles. For the particles formed in zeolite-USY, the size is around 1 nm and all the $Mn^{2+}$ ions are at the near-surface sites. The temperature dependence of photo- and upconversion luminescence spectra is shown in FIG. 6.

Figure 7:
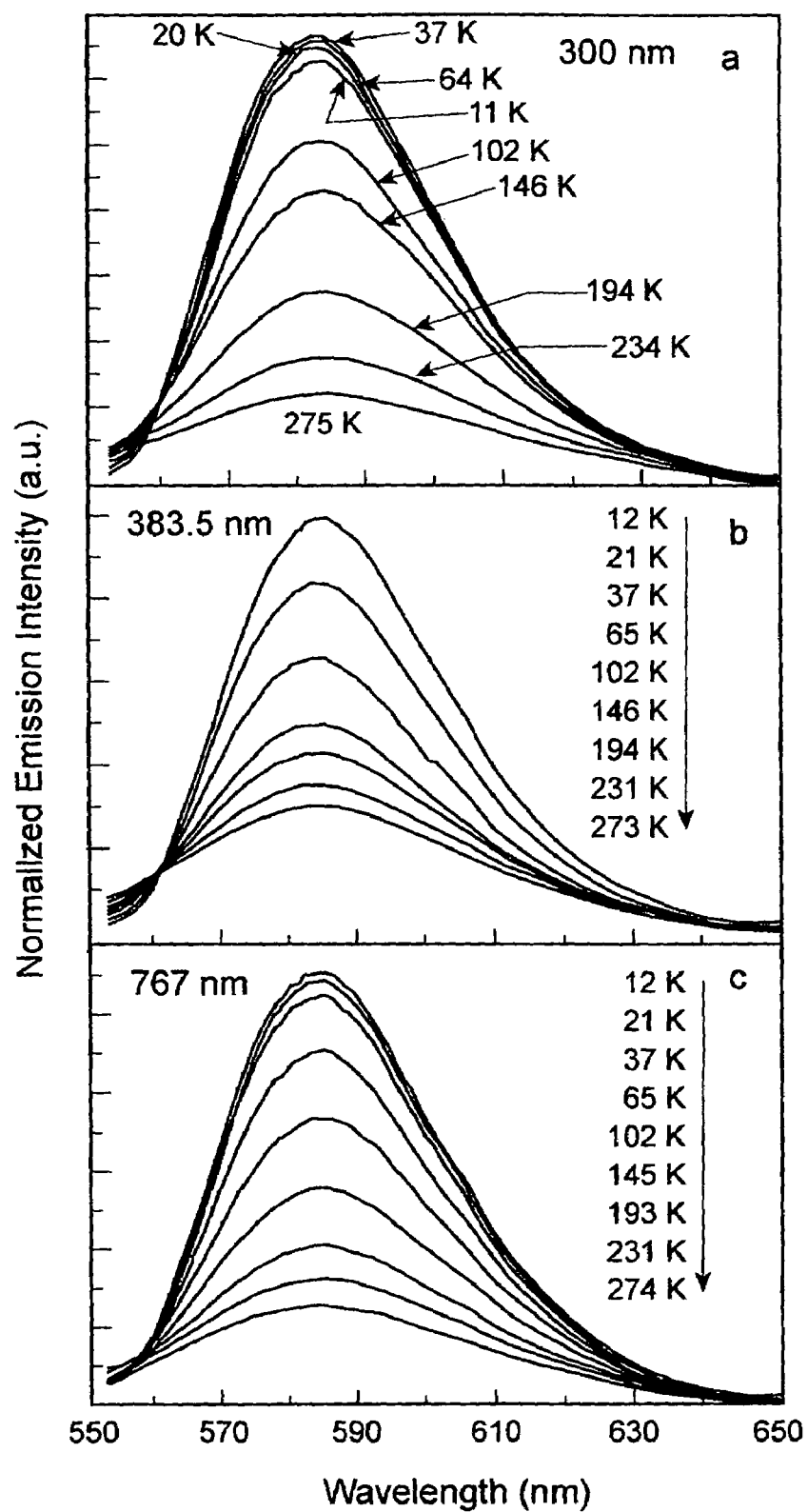
FIG. 7 is a graphical representation of the emission spectra of Mn$^{2+}$ in bulk ZnS:Mn$^{2+}$ excited at (a) 300 nm and (b) 383.5 nm, and (c) upconversion luminescence induced at 767 nm excitation at differing temperatures.

The temperature dependent luminescence spectra of bulk $ZnS:Mn^{2+}$ in which all $Mn^{2+}$ ions are in the lattice sites is shown in FIG. 7. FIGS. 5, 6, and 7 reveal that the temperature dependence of the luminescence is different for different sized $ZnS:Mn^{2+}$ particles.

With decreasing temperature, the emission spectra of both photo- and upconversion luminescence shift to longer wavelengths. This is due to the enhancement of the crystal field at lower temperatures that results from crystal lattice contraction. As a consequence, the emitting state, $^4T_1(G)$ of $Mn^{2+}$, shifts to lower energies with decreasing temperature, shifting the emission to longer wavelengths. It is also evident from FIGS. 5, 6, and 7 that the emission shift for decreasing temperature in the 3.5 nm size particles is larger than that of the bulk and particles in zeolite-USY for all three excitation wavelengths. In the 3.5 nm sized nanoparticles, the emission band is an overlap of emissions from the $Mn^{2+}$ ions at the lattice sites and the near-surface sites, with the latter at the longer wavelength side. It is reasonable to assume that the effects of temperature change at the near-surface sites are more pronounced than at the lattice sites, because the exciton-phonon coupling in the near-surface sites is most likely stronger. The exciton-phonon coupling strength in nanoparticles is determined by both the quantum confinement and the surface characteristics.

First, the density-of-states for both the electrons and phonons decreases with size, which is likely to result in a weaker electron-phonon coupling. Similarly, the increased overlap between the electron and hole wave functions decreases the exciton-phonon coupling. In nanoparticles, the overlap between the electron and hole wave functions may decrease due to the trapping of electrons or holes to the surface states, increasing the phonon coupling strength. Thus, in the same nanoparticles, the exciton-phonon coupling in the near-surface sites is stronger than in the lattice sites. Therefore, with decreasing temperature, the enhancement of the crystal field strength at the near-surface sites is greater than at the lattice sites, and the related changes in the emission intensity and energy of the near-surface sites are more dramatic with decreasing temperature. This effect is even more pronounced in the spectra obtained following 383.5 and 767 nm excitation, because these excitation wavelengths preferentially excite the near-surface $Mn^{2+}$ ions.

In contrast, even though most $Mn^{2+}$ ions are at the near-surface sites in the particles formed in zeolite-USY, the temperature dependence of its emission energy is similar to that of bulk ZnS:$Mn^{2+}$. These nanoparticles are encapsulated in the zeolite cavities and the particle surfaces are well passivated such that the exciton-phonon coupling contributions from surface states are less pronounced. The surface passivation of the nanoparticles encapsulated in zeolites is actually via the chemical bonding between the anions ($Zn^{2+}$) at the nanoparticle surfaces and the zeolite framework oxygen ions ($O_{2-}$—G. A. Ozin, *NANOCHEMISTRY—SYNTHESIS IN DIMINISHING DIMENSIONS*, Adv. Mater. 4, 612 (1992)). In this case, the surrounding of $Mn^{2+}$ in ZnS:$Mn^{2+}$/USY is similar to $Mn^{2+}$ in bulk ZnS:$Mn^{2+}$. This is the reason the two samples have similar luminescence temperature behaviors.

It is known from the preceding discussion that the temperature dependence of the luminescence intensity is closely related to the particle surface-interface characteristics. Better surface passivation likely results in a simplified temperature dependence. Previous work demonstrated that an inorganic coating is better than an organic coating for surface passivation. (N. S. Nalwa, Editor, *Handbook of Nanostructured Materials and Nanotechnology*, Academic Press, San Diego (2000), Vol. 4; G. A. Ozin, *NANOCHEMISTRY—SYNTHESIS IN DIMINISHING DIMENSIONS*, Adv. Mater. 4, 612 (1992)) Here, the ZnS:$Mn^{2+}$ nanoparticles encapsulated in zeolite-USY are better passivated than MA/CA capped particles. This can be further evidenced from the observations that in the 3.5 nm particles, a blue emission at 425 nm is observed (data not shown) that is attributed to surface defects or deep traps. However, in the particles encapsulated in zeolite-USY, the defect-related blue emission is not observed. Also, it was reported that ultraviolet (UV) curing can enhance the luminescence intensity of MA capped ZnS:$Mn^{2+}$ nanoparticles. This enhancement is attributed to better surface passivation of MA polymerization by UV curing. All these factors indicate that surface defects exist in the MA capped nanoparticles and thus surface effects must be considered for explaining the observed experimental results.

Temperature Dependence of the Emission Intensity

Figure 8:
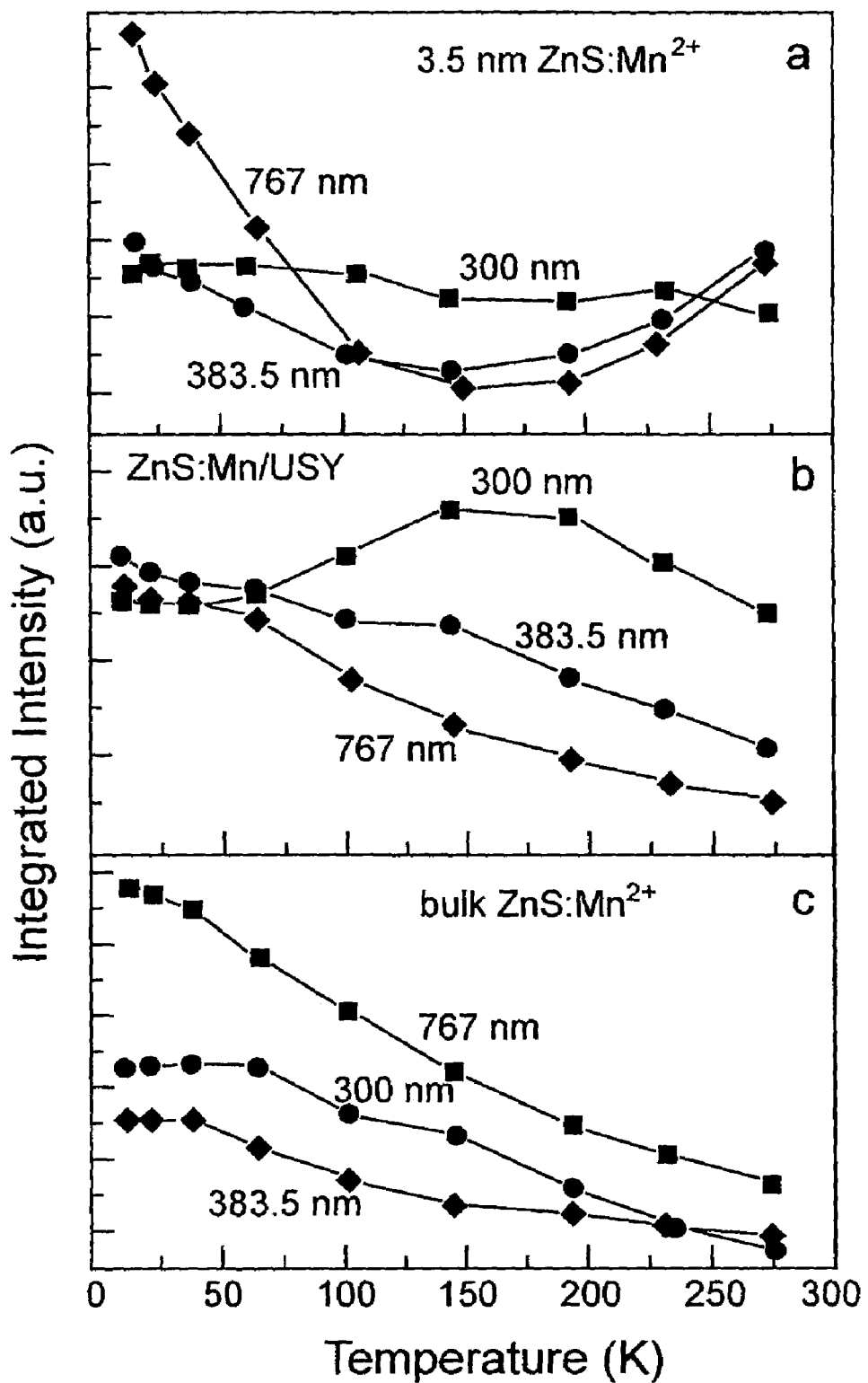
FIG. 8 is a graphical representation of the temperature dependences of the spectral intensity following 300 nm (circles), 383.5 nm (diamonds), and 767 nm (squares) excitation of (a) 3.5 nm sized ZnS:Mn$^{2+}$ nanoparticles, (b) ZnS:Mn$^{2+}$ nanoparticles in zeolite-USY, and (c) bulk.

The temperature dependence of the luminescence intensity is more complicated than that of the emission energy. FIG. 8 displays the relative intensity changes as a function of the temperature for all three samples. For bulk ZnS:$Mn^{2+}$ and ZnS:$Mn^{2+}$/USY, the upconversion luminescence and the 383.5 nm excited photoluminescence increase in intensity with decreasing temperature. The 300 nm excited photoluminescence of bulk ZnS:$Mn^{2+}$ increases in intensity with decreasing temperature from room temperature to 64 K, and then decreases slightly from 64 to 10 K. The 300 nm excited photoluminescence of ZnS:$Mn^{2+}$/USY increases in intensity with decreasing temperature from room temperature to 145 K, and then decreases with decreasing temperature from 145 to 10 K. For the 3.5 nm sized nanoparticles, the temperature dependences of the luminescence intensity are totally different from bulk ZnS:$Mn^{2+}$ and ZnS:$Mn^{2+}$/USY. The 300 nm excited photoluminescence does not vary much in intensity for different temperatures, whereas the upconversion and the 383.5 nm excited photoluminescence decrease in intensity with decreasing temperature from room temperature to 150 K, and then increase with decreasing temperature from 150 to 10 K. One common feature for all the three samples is that the temperature dependence of the 767 nm excited upconversion luminescence is the same as the 383.5 nm excited photoluminescence.

This data further supports the conclusion that the upconversion luminescence is due to two-photon absorption. The temperature dependence of the luminescence intensity for the bulk ZnS:$Mn^{2+}$ is similar to published results. (D. D. Thong and O. Goede, *OPTICAL STUDY OF HIGHLY Mn-DOPED ZNS CRYSTALS*, Phys. Status Solidi B 120, K145 (1983)). The gradual increase of the luminescence intensity with decreasing temperature may be explained by a weakening of phonon coupling at lower temperatures, the common theory for thermal quenching. The temperature dependence of $Mn^{2+}$ photoluminescence intensity in ZnS:$Mn^{2+}$ nanoparticles was reported by J. Q. Yu, H. M. Liu, Y. Y. Wang, F. E. Fernandez, and W. Y. Jia, *Optical properties of ZnS:$Mn^2$+ nanoparticles in polymer films*, J. Lumin. 76&77, 252 (1998). and M. Tanaka, and Y. Masumoto, *Very weak temperature quenching in orange luminescence of ZnS:Mn2+ nanocrystals in polymer*, Chem. Phys. Lett. 324, 249 (2000). J. Q. Yu, H. M. Liu, Y. Y. Wang, F. E. Fernandez, and W. Y. Jia, *Optical properties of ZnS:Mn2+ nanoparticles in polymer films*, J. Lumin. 76&77, 252 (1998) observed that the luminescence intensity of $Mn^{2+}$ in polymer capped ZnS:$Mn^{2+}$ nanoparticles increases significantly with temperature from 8 to 275 K, and then decreases with increasing temperature. However, Tanaka and Masumoto observed that the luminescence intensity of $Mn^{2+}$ in ZnS:$Mn^{2+}$ nanoparticles was very weakly dependent on temperature. In our observations, we find that the 300 nm excited photoluminescence of $Mn^{2+}$ in the 3.5 nm sized nanoparticles is weakly dependent on temperature. In addition, in these studies we also find that the temperature behavior of ZnS:$Mn^{2+}$ nanoparticles is dependent on both the particle size and the surface characteristics as evidenced from the data obtained from the 1 nm USY and 3.5 nm samples (FIG. 8). The upconversion and the 383.5 nm excited luminescence of the 3.5 nm sized nanoparticles, and the luminescence of the ZnS:$Mn^{2+}$/USY are strongly dependent on temperature, and the upconversion luminescence is more sensitive to temperature than the photoluminescence. These experiments and the results also support the conclusion that the upconversion is due to two-photon absorption rather than Auger recombination, because the Auger upconversion luminescence intensity is less sensitive to temperature change than that of photoluminescence.

Figure 9:
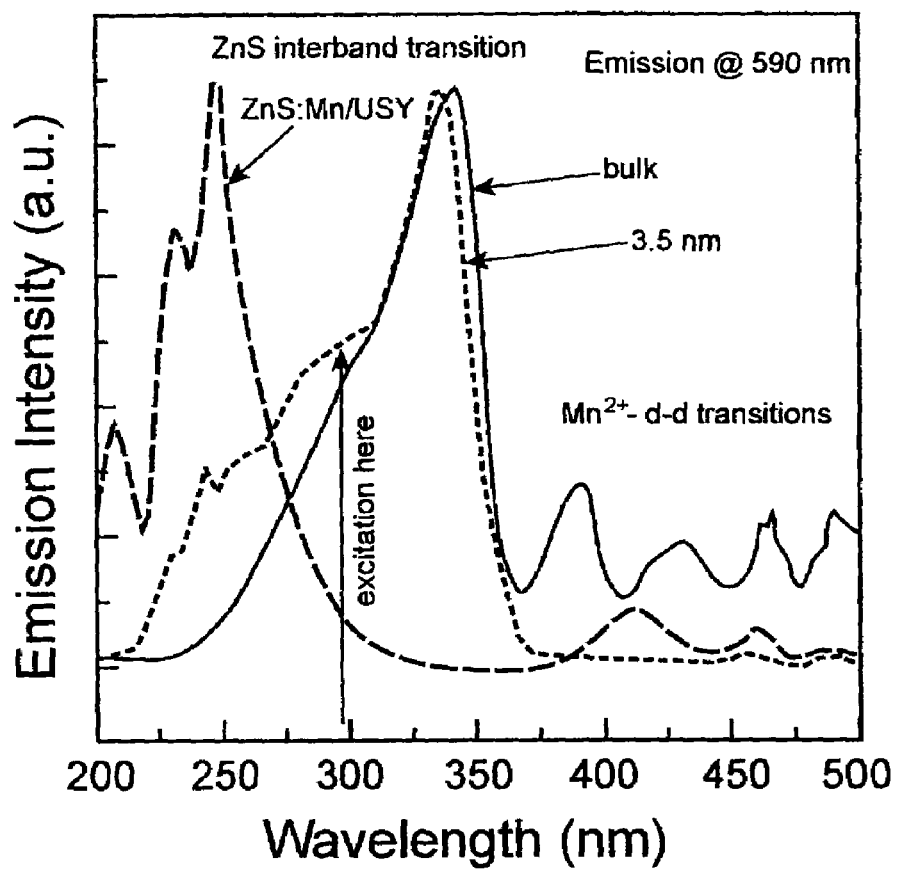
FIG. 9 is a graphical representation of the excitation spectra of ZnS:Mn$^{2+}$/USY, ZnS:Mn$^{2+}$ nanoparticles of 3.5 nm size, and bulk ZnS:Mn$^{2+}$.

There are two common mechanisms for luminescence excitation in doped semiconductors. One is excitation of the impurity ions to their excited states directly. The other type is indirect excitation, i.e., excitation into the excited levels of the host, followed by energy transfer from the host to the impurity ions, thereby inducing the luminescence. This type of excitation is termed interband excitation. FIG. 9 displays the excitation spectra for all three samples. It is clear from FIG. 9 that the 300 nm excitation of $Mn^{2+}$ is predominantly due to interband excitation, whereas the excitation at either 383.5 or 767 nm is most likely due to direct d-d excitation of the $Mn^{2+}$ ions themselves.

We first consider the case of interband excitation following 300 nm irradiation. In this case, the luminescence intensity of $Mn^{2+}$ in ZnS:$Mn^{2+}$ can be expressed as:

$$I(T) \mu [ZnS(T) \sigma Mn(T)]$$

where T is the absolute temperature, [ZnS(T) is the energy transfer rate from ZnS excitons to $Mn^{2+}$, and σMn(T) is the luminescence efficiency of the $Mn^{2+}$ $^4T_1 \rightarrow {}^6A_1$ transition in the absence of energy transfer to other species or defect states. If there is energy transfer from $Mn^{2+}$ to other states such as surface states in the nanoparticles, the luminescence intensity of $Mn^{2+}$ in $ZnS:Mn^{2+}$ should be expressed as:

$$I(T) \propto [[ZnS(T) \sigma Mn(T)]/\lceil_{ET}(T)$$

where $\lceil_{ET}(T)$ is the energy transfer rate from $Mn^{2+}$ ions to other states.

The content of surface states in the nanoparticles prepared in methacrylic and citric acids is much higher than in the nanoclusters encapsulated in zeolite-USY. Furthermore, it has been suggested that in weakly confined nanoparticles such as the 3.5 nm size studied, energy can transfer from the excited states [$^4E(^4D)$ and $^4T_2(^4D)$] of $Mn^{2+}$ to the surface states, whereas energy cannot transfer from the excited states of $Mn^{2+}$ to the surface states in the strongly confined nanoclusters like those encapsulated in zeolite-USY, because the surface states in the latter are higher in energy than the $Mn^{2+}$ excited states. Thus, in $ZnS:Mn^{2+}$/USY and bulk $ZnS:Mn^{2+}$, we will not consider the energy transfer from $Mn^{2+}$ to explain the temperature dependence of the luminescence; in the 3.5 nm sized nanoparticles, the energy transfer from $Mn^{2+}$ ions to surface states must be considered.

[ZnS(T) is determined by three processes: (1) dissociation of the ZnS excitons, (2) nonradiative processes, and (3) energy transfer from the exciton to defects or surface states. In nanoparticles, due to quantum size confinement, the exciton binding energy increases and the thermal dissociation temperature usually is higher than room temperature. Therefore, in the measured range, the temperature change has little effect on exciton dissociation. The exciton nonradiative relaxation proceeds via exciton-phonon coupling, which is determined by both the quantum confinement and the surface characteristics. As described previously, the density of states and the increased overlap between electron and hole wave functions serve to weaken the electron-phonon coupling. On the other hand, the overlap between the electron and hole wave functions may decrease due to trapping of electrons or holes to the surface states, increasing the phonon coupling strength. These factors may compete with each other and determine the overall size dependence of the phonon coupling strength. Therefore, if only the exciton binding energy and the exciton-phonon coupling are considered, the temperature dependence of the 300 nm excited luminescence (which predominantly excites lattice site $Mn^{2+}$ ions) is expected to be less pronounced in nanoparticles than in the bulk (Table I). Table I lists the experimentally determined ratios of highest intensity to lowest intensity within the measured temperature ranges.

TABLE I

| Excitation | 300 nm | 767 nm | 383.5 nm |
|---|---|---|---|
| Zns:Mn$^{2+}$/USY | 1.430 | 2.788 | 5.039 |
| 3.5 nm | 1.123 | 2.116 | 1.391 |
| Bulk | 4.226 | 3.378 | 2.527 |

For the 3.5 nm sized nanoparticles, a blue emission at 420 nm is observed. This luminescence has been assigned to the sulfur-vacancy defects, implying that a high degree of defects are present in these nanoparticles such that the foregoing process is expected to make a significant contribution to [ZnS (T). The luminescence quenching by this energy transfer is more efficient at lower temperatures, because thermal depopulation via phonons is decreased. This luminescence quenching may compete with the phonon quenching, which is stronger at high temperatures. Thus, the temperature dependence of the 300 nm excited luminescence in the 3.5 nm sized nanoparticles is even weaker than in $ZnS:Mn^{2+}$/USY (Table I). Note that the 300 nm excited luminescence of $ZnS:Mn^{2+}$/USY decreases in intensity with decreasing temperature from 145 to 10 K. Most likely, this decrease is related to the decrease in absorption intensity at 300 nm. As displayed in FIG. 9, the 300 nm excitation is near the band edge of the $ZnS:Mn^{2+}$/USY absorption, whereas it is significantly above the band edge for the other particles. As the temperature decreases, the ZnS absorption band shifts to shorter wavelengths due to a shift of the band edge toward higher energy. As a result, the absorption intensity at 300 nm decreases for $ZnS:Mn^{2+}$/USY, while the absorption at 300 nm remains the same or increases slightly in intensity for the 3.5 nm sized nanoparticles and the bulk.

The second case we consider is that due to direct excitation of the $Mn^{2+}$ d-d transitions expected following excitation at either 383.5 or 767 nm. In this case, the luminescence efficiency is determined by two processes: the nonradiation relaxation of the excited states via phonon coupling and the energy transfer from $Mn^{2+}$ excited states to the surface states. As previously discussed, only in the 3.5 nm sized nanoparticles should the energy transfer from $Mn^{2+}$ to the surface states be considered. In bulk and $ZnS:Mn^{2+}$/USY, the main temperature effect we need to consider is phonon coupling.

Thus, it is expected that the 383.5 nm luminescence and the 767 nm upconversion luminescence increase with decreasing temperature due to the decrease in phonon coupling, which is in agreement with the observations. For the 3.5 nm sized nanoparticles, however, the luminescence intensity first decreases and then increases with increasing temperature. This behavior may be understood by considering the competition between phonon quenching and surface quenching, which together may determine the overall temperature dependence of the luminescence intensity. The luminescence intensity decrease with increasing temperature can be understood based on phonon quenching, as discussed.

Figure 10:
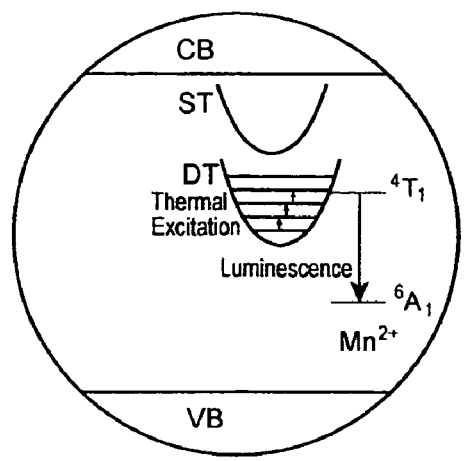
FIG. 10 is a schematic illustration of the effect of surface (trap) state quenching of the excited state of Mn$^{2+}$ Abbreviations: ST, shallow traps; DT, deep traps; CB, conduction band; VB, valance band. The upward arrows indicate excitation due to thermal energy or increasing temperature. With lowering temperature, the DT is expected to quench the Mn$^{2+}$ excited state and reduce the luminescence intensity.

The luminescence increase with increasing temperature can be rationalized by considering surface state quenching, because charge carriers at the surface states or trap states can be activated or excited at higher temperatures and participate in energy transfer to the excited state of $Mn^{2+}$, thereby resulting in an increase in $Mn^{2+}$ luminescence. This is illustrated schematically in FIG. 10. In other words, as the temperature decreases, the surface states, most likely deep trap states, become more effective in quenching the excited state of $Mn^{2+}$. By considering these two competing mechanisms— phonon quenching and surface quenching—we can understand that the 383.5 nm induced luminescence and the upconversion luminescence following 767 nm excitation first decrease and then increase in intensity with increasing temperature.

In summary, the temperature dependences of the photoluminescence and upconversion luminescence of $ZnS:Mn^{2+}$ nanoparticles and bulk have been described—i.e. a UCL material having the general formula (X):(Y) wherein (X) is a host such as a nanoparticle and (Y) is a dopant such as a rare earth or transition metal ion, has been described and enabled. The observed shift of the $Mn^{2+}$ $^4T_1 \rightarrow {}^6A_1$ emission to longer wavelengths at lower temperatures is explained by the increase in the crystal field strength, that moves the emitting state $^4T_1$ to lower energies. The temperature dependence of the luminescence intensity shows complicated behavior, indicating the underlying interplay of energy transfer and relaxation processes in these materials. This interesting temperature behavior may be reasonably explained by considering the processes of nonradiation relaxation via phonon coupling, exciton thermal dissociation (binding energy), energy transfer, carrier trapping, and temperature dependence of the absorption spectra. The fact that the temperature dependence of the 767 nm excited upconversion luminescence is the same as the 383.5 nm excited photoluminescence for all the three samples supports the conclusion that the upconversion luminescence is due to two-photon absorption.

Usage of the UCL Materials Discussed Hereinabove

Upconversion Luminescence Production Assembly

Figure 11:
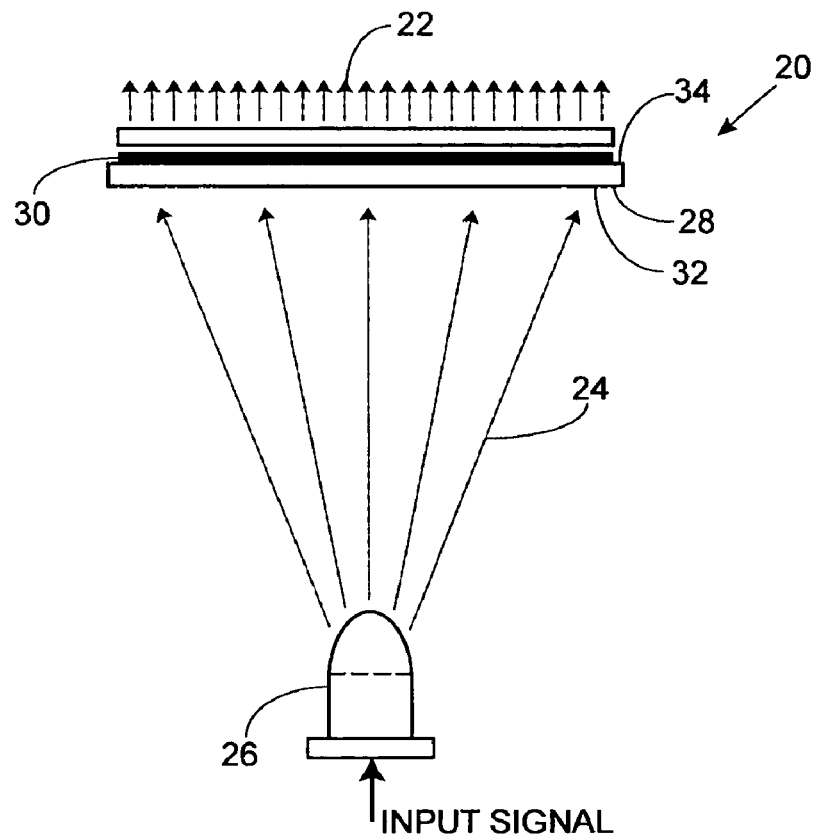
FIG. 11 is a schematic, diagrammatic view of an upconversion luminescence production assembly constructed in accordance with the present invention.

Referring now to FIG. 11, shown therein is an upconversion luminescence production assembly 20 constructed in accordance with the present invention. As will be discussed in more detail below, the upconversion luminescence production assembly 20 produces an emission 22 having a greater energy level, e.g. hv, eV, or a shorter wavelength, than an excitation 24. The upconversion luminescence production assembly 20 can be implemented in various forms, such as an upconversion Light Emitting Diode (L.E.D.), an upconversion laser, a light bulb, etc.

In general, the upconversion luminescence production assembly 20 includes an electromagnetic source 26, a substrate 28, and a UCL material 30. The electromagnetic source 26 receives an input signal and in response thereto emits the excitation 24 having an excitation wavelength. The input signal can be a voltage, current or other type of signal capable of causing the electromagnetic source 26 to produce the excitation 24.

The substrate 28 is positioned within the excitation 24 emitted by the electromagnetic source 26. The UCL material 30 covers at least a portion of the substrate 28 such that the excitation 24 emitted by the electromagnetic source 26 is received by at least a portion of the UCL material 30. The UCL material 30 is formed of one or more of the doped nanoparticles discussed above. The UCL material 30 produces the emission 22 through upconversion luminescence such that the emission 22 has the emission wavelength which is shorter than the excitation wavelength of the excitation 24 received by the UCL material 30. Thus, the energy level of the emission 22 is higher than the energy level of the excitation 24.

The electromagnetic source 26 can be any device capable of producing the excitation 24, e.g., a light emitting diode, a laser, a lamp, or a heating element such as a hot wire. The excitation wavelength can vary depending on the desired emission wavelength, as well as the particular material forming the UCL material 30. For example, the excitation wavelength of the excitation 24 can form radio frequency signals, infrared light, visible light, ultraviolet light, microwaves or x-ray radiation. In one preferred embodiment, the electromagnetic source 26 is an infrared source, and the UCL material 30 converts the infrared light (excitation 24) to visible light (emission 22). In this instance, the excitation wavelength would be longer than about 800 nm and the emission wavelength would be in a range between about 360 nm to about 750 nm or shorter than 800 nm.

The substrate 28 can be any material capable of supporting the UCL material 30 such that the excitation 24 produced the electromagnetic source 26 can be received by the UCL material 30. For example, as shown in FIG. 11, the substrate 28 can be provided with a first side 32 and an opposed second side 34. The electromagnetic source 26 is positioned adjacent to the first side 32 of the substrate 28, and the UCL material 30 is applied to and thereby covers at least a portion of the second side 34 of the substrate 28. In this instance, the substrate 28 is selected of a material allowing passage of the excitation 24 to the UCL material 30, preferably without substantial scattering or loss of the excitation 24. Of course, the substrate 28 is selected depending on the particular wavelengths of light produced by the electromagnetic source 26. When the electromagnetic source 26 is an infrared electromagnetic source, the substrate 28 can be constructed of a substantially transparent material such as quartz, glass, methyl-acrylate, or natural or synthetic polymers. The excitation 24 produced by the electromagnetic source 26 passes through the substrate 28 (alternatively, excitation 24 can be produced by an electromagnetic source located within the substrate 28) and is received by the UCL material 30. In response thereto, the UCL material 30 produces the emission 22. Emission 22, thereby has a higher energy than excitation 24.

Although the UCL material 30 has been shown in FIG. 11 as being positioned on the second side 34 of the substrate 28, it should be understood that other configurations are contemplated. For example, the UCL material 30 can be applied to the first side 32 of the substrate 28, within the substrate 28, on an edge(s) 36 of the substrate 28 or on the second side 34 of the substrate 28. In the instance when the UCL material 30 is applied to first side 32 of the substrate 28, the emission 22 will typically pass through the substrate 28 if the substrate 28 is constructed of a material which permits passage of the emission 22.

The UCL material 30 includes one or more nanoparticles formed from the UCL material(s) discussed above. With respect to the UCL materials incorporating a dopant such as Manganese but not limited thereto, the UCL material 30 can alternatively be formed of bulk materials, such as powders as well as nanoparticles. The UCL material 30 is desirably constructed of a film positioned on the first side 32 and/or the second side 34 of the substrate 28. The thickness of the film can vary depending on the properties desired in the emission 22. That is, as the thickness of the film increases, the brightness of the emission 22 will also increase until the thickness of the film serves to limit the brightness. The thickness of the film can be 1 nanoparticle thickness or greater.

The UCL material 30 preferably has a substantially uniform thickness. However, it should be understood that the thickness of the UCL material 30 can be varied if desired. Varying the thickness of the UCL material 30 will form areas having greater and lower intensities of the emission 22.

The UCL material 30 can be applied to the substrate 28 via any suitable method or system capable of connecting or supporting the UCL material 30 on or by the substrate 28. Any system or method can be used so long as such system or method does not change the properties of the nanoparticles utilized to form the nanoparticles device.

The following methods are suitable for making nanoparticle thin films: layer-by-layer ("LBL") assembly, spin-coating or spin-casting, spray, thermal spray, drop, supercritical fluids, thermal plasma deposition, and laser ablation. The preferred methods for forming the nanoparticle thin films are spin-coating, layer-by-layer, spray and ink-jet printing. One of ordinary skill in the art would appreciate, however, that these methods are not exhaustive and any method of making a nanoparticle thin film is contemplated for use.

Layer-by-layer assembly has been initially introduced by G. Decher (G. Decher, *Fuzzy nanoassemblies: toward layered polymeric multicomposites*, Science, 1997, 277: 1232-1237) for oppositely charged polyelectrolytes. Being quite universal, it was later expanded to the assembly of various inorganic colloids. One of the most promising directions of this technique is that the preparation of hybrid organic-inorganic materials affords the combination of optical and electric properties of inorganic components with excellent adhesion, processability and flexibility of polymers. N. A. Kotov, I. Dekany and J. H. Fendler, *Layer-by-layer self-assembly of polyelectrolyte-semiconductor nanoparticle composite films*, J. Phys. Chem. 1995, 99:13065-13069 were the first to report on LBL assembly of Group II-VI semiconductor nanoparticles, where light emitting properties of quantum dots were successfully integrated into a thin hybrid film. Additionally, it was demonstrated that not only the II-VI material itself but also the order in which the layers were assembled affect photophysical and photochemical processes in the multilayer assembly. Later, it was also confirmed for the photo-induced charge transfer in LBL assemblies of CdS and graphite oxide.

The advantages of layer-by-layer thin films are:
1. Pinhole-free coatings, which may vary in thickness from nanometers to millimeters;
2. Optimization of charge-transfer properties of the light-emitting layer via organized multilayer assemblies;
3. Ordered multicomponent structures, which can be deposited on traditional solid flat substrates, flexible plastic skins, and curved sophisticated surfaces such as helmet visors with equal efficiency; and
4. Universality of the deposition—that is, different kinds of nanoparticles and conductive polyelectrolytes can be used with minimal variations in the deposition technique.

The driving force for LBL is the electrostatic attraction of positive and negative charges located on the surface of inorganic colloids and polyelectrolytes. An important thermodynamic contribution to the film stability is also made by the van Der Waals interactions. Typically, the assembly process consists of a cyclic repetition of four steps:
1. Immersion of the substrate 28 into an aqueous 0.1-2% (w/v) solution of a polymer for 1-2 minutes,
2. Rinsing with ultra-pure deionized water for 30 seconds,
3. Immersion into an aqueous dispersion of oppositely charged particles, and
4. Final rinsing with deionized water for 30 seconds.

The substrate 28 can be constructed of any material capable of supporting or lending support to a UCL material 30. The substrate 28 can be opaque or transparent. The substrate 28 can be constructed of a rigid material, such as quartz, or a flexible material such as natural or synthetic polymers, cloth, or combinations thereof. The substrate 28 can be formed of a solid material, a liquid material, or a gaseous material. Although the substrate 28 has been shown in FIG. 11 as a substantially planar material having a uniform thickness, this need not be the case. The substrate 28 can be accurately shaped (concave, convex or combinations thereof), planar shaped, fancifully shaped or combinations thereof.

The electromagnetic source 26 is shown in FIG. 11 as being spaced a distance away from the substrate 28. The distance between the electromagnetic source 26 and the substrate 28 can be varied depending on the particular configuration of the upconversion luminescence production assembly 20. In fact, when the upconversion luminescence production assembly 20 is implemented as an LED, the electromagnetic source 26 is positioned in very close proximity to the substrate 28.

Although the electromagnetic source 26 is shown in FIG. 11 as being below the substrate 28, it should be understood that the electromagnetic source 26 can be positioned above the substrate 28, below the substrate 28, beside the substrate 28, encompassed by the substrate 28 or in any other configuration with respect to the substrate 28 so long as the excitation 24 produced by the electromagnetic source 26 is received or can be received by the UCL material 30. Although not shown, one or more mirror or waveguide can also be used for directing the excitation 24 onto the UCL material 30.

Furthermore, the position of the electromagnetic source 26 can be fixed with respect to the position of the substrate 28, or, the position of the electromagnetic source 26 can be varied with respect to the position of the substrate 28, or vice versa. In other words, the electromagnetic source 26 can be provided in a fixed location and the substrate 28 moveable into and/or out of the excitation 24, the substrate 28 can be provided in a fixed location and the electromagnetic source 26 moveable with respect to the substrate 28, or both the substrate 28 and the electromagnetic source 26 can be moveable with respect to each other.

For example, the upconversion luminescence production assembly 20 can be implemented in the form of a security system for use at clubs where it is desirable to determine whether an individual has paid the cover charge. That is, upon payment of a cover charge, the UCL material 30 can be applied to a hand or an arm of an individual (substrate 28) by any suitable process, such as by stamping. A guard or other security personnel can be provided with an electromagnetic source 26, such an infrared electromagnetic source, which such security personnel could shine on the individual's hands and/or arm to determine whether the individual has paid the cover charge. Upon receipt of the infrared light (excitation 24) the UCL material 30 would upconvert the excitation 24 to a visible light so that the security personnel could determine whether that individual's arm and/or hand had been stamped.

Figure 11A:
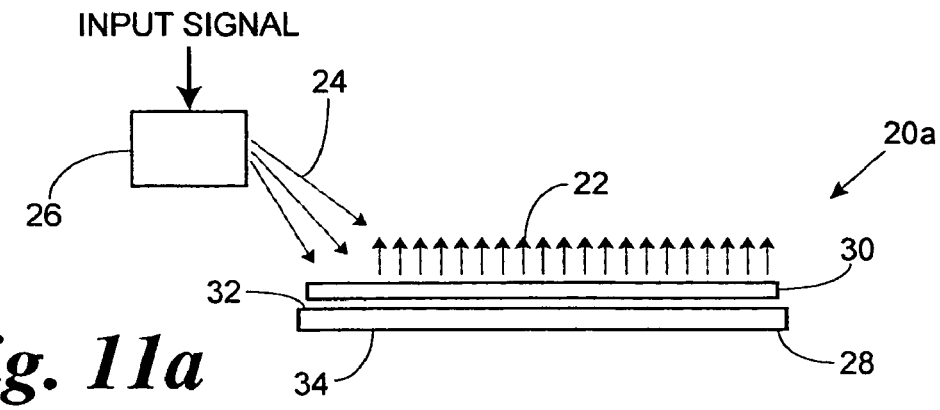
FIG. 11a is a schematic, diagrammatic view of another version of an upconversion luminescence production assembly constructed in accordance with the present invention.

Shown in FIG. 11a is another example of an upconversion luminescence production assembly 20a constructed in accordance with the present invention. The upconversion luminescence production assembly 20a is similar in construction and function as the upconversion luminescence production assembly 20 shown in FIG. 11, except that the UCL material 30 and the electromagnetic source 26 are positioned on a same side of the substrate 28. As shown in FIG. 11a, the excitation 24 contacts the UCL material 30 (without passage of the excitation 24 through the substrate 28). The UCL material 30 upconverts the excitation 24 to form the emission 22. The emission 22 is emitted from the UCL material 30 in a direction generally toward the electromagnetic source 26.

Figure 11B:
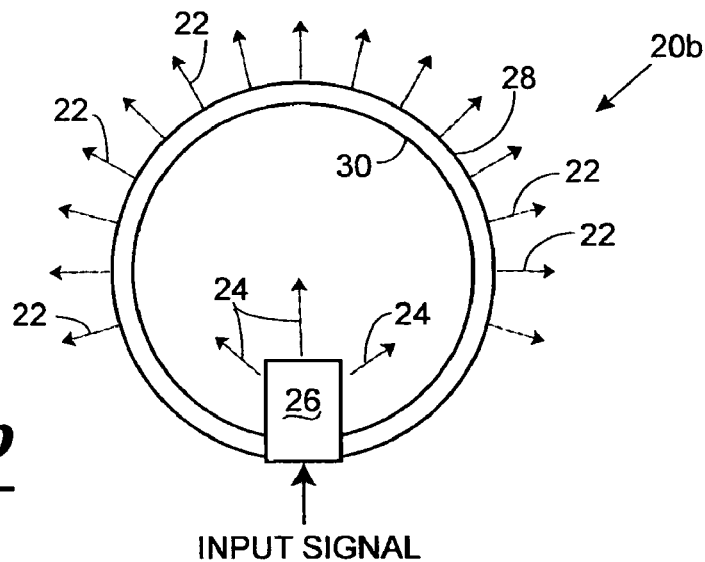
FIG. 11b is a schematic view of yet another version of an upconversion luminescence production assembly constructed in accordance with the present invention.

Shown in FIG. 11b is yet another example of an upconversion luminescence production assembly 20b constructed in accordance with the present invention. The upconversion luminescence production assembly 20b can be characterized as a light bulb. The upconversion luminescence production assembly 20b is similar in construction and function as the upconversion luminescence production assembly 20 shown in FIG. 11, except that the substrate 28 substantially encompasses the electromagnetic source 26. The intensity of the emission 22 can be controlled by varying the intensity of the excitation 24 produced by the electromagnetic source 26.

Recently, upconversion lasers have been reported in rare earth ion doped halide crystals by W. Lenth, and R. M. Macfarlane, *Upconversion lasers*, Optics and Photonics News, (March, 1992), pp 8-14 and P. Xie and S. C. Rand, *Astigmatically compensated, high gain cooperative upconversion laser*, Applied Physics Letters, 1992, 60: 3084-3086. In the present invention, it has been demonstrated that doped nanoparticles have strong upconversion luminescence. Thus, it is expected that it is possible to fabricate upconversion lasers made by these nanostructured materials.

Figure 11C:
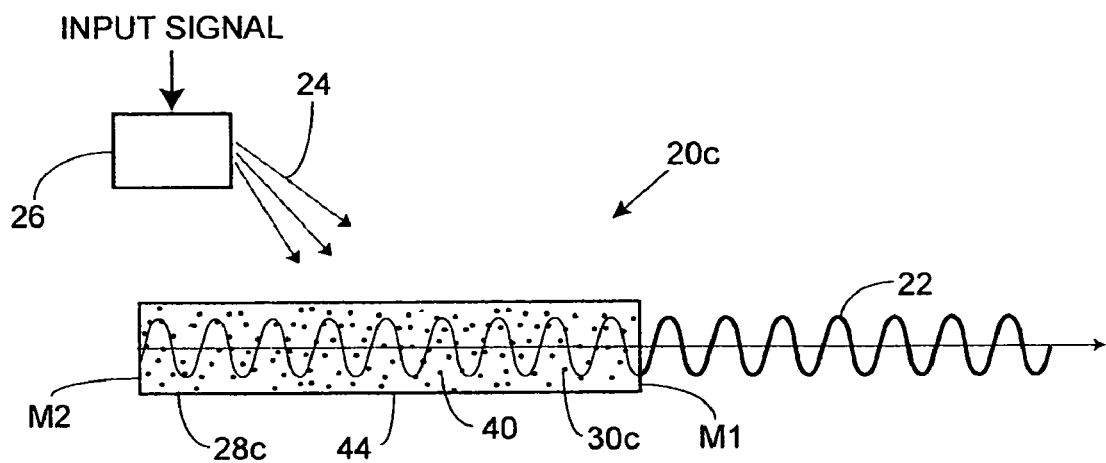
FIG. 11c is a schematic view of yet another version of an upconversion luminescence production assembly constructed in accordance with the present invention.

Referring now to FIG. 11c, shown therein and designated by a reference numeral 20c is an example of an upconversion luminescence production assembly 20c configured as a laser (or laser diode). The laser 20c includes two reflective surfaces M1 and M2 forming a laser cavity 40, and a substrate 28c positioned within the laser cavity 40. The substrate 28c can be in the form of a rod.

The reflective surfaces M1 and M2 can be made with any suitable materials capable of reflecting energy, such as light within the laser cavity. For example, the reflective surfaces M1 and M2 can be made with silver, gold or tool steels. One of the two reflective surfaces M1 and M2 must be semi-transparent. For example, a partially silvered mirror can be used as a semi-transparent reflective surface (M1) at one end of the substrate 26c while a totally silvered reflective surface (M2) can be used at the other end. The substrate 26c can be made with ruby, silica or glass. Reflective surfaces of the reflective surfaces M1 and M2 at both ends of the laser cavity 40 permit energy to reflect back and forth, building up in each passage.

A UCL material 30c formed of nanoparticles, or other size materials as discussed above can be disposed into the substrate 28c by solid state diffusion at high temperature such as 800° C. or by ion-exchange in solution (W. Chen, R. Sammynaiken, and Y. Huang, *Luminescence enhancement of ZnS: Mn nanoclusters in zeolite*, J. Appl. Phys. 88, 5188 (2000). And W. Chen, X. H. Zhang, and Y. Huang, *Luminescence enhancement of EuS nanoclusters in zeolite*, Appl. Phys. Lett., 2000, 24, 2328-2330). Alternatively or in addition, the UCL material 30c can be coated to an exterior surface 44 of the substrate 28c by any suitable technique, such as layer-by-layer assembly or spray.

The laser 20c includes the electromagnetic source 26, which in this instance can be a laser or other light source such as an infrared light-emitting diode. Upon optically pumping from the electromagnetic source 26, the emission from the UCL material 30c will bounce back and forth between the reflective surfaces M1 and M2 until coherent light escapes from the laser cavity 40. This process is called stimulated emission. The bombarding photon and the emitted photon may then each strike other excited particles, stimulating further emission of photons, all of the same frequency and phase. It is expected that this process will produce a sudden burst of coherent radiation, that is a lasing action.

Figure 11D:
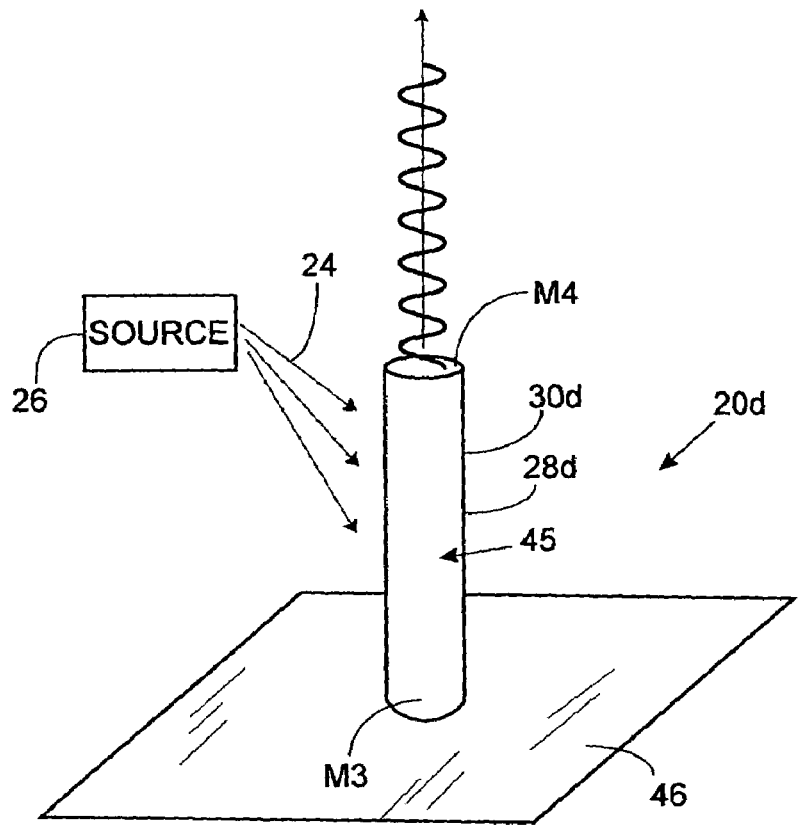
FIG. 11d is a schematic view of yet another version of an upconversion luminescence production assembly constructed in accordance with the present invention.

Referring to FIG. 11d, designated therein by the reference numeral 20d is another example of an upconversion luminescence production assembly wherein the upconversion luminescence production assembly is configured as a laser. The upconversion luminescence production assembly 20d is similar in construction and function as the upconversion luminescence production assembly 20c, except that the upconversion luminescence production assembly 20d includes a substrate 28d formed by one or more nanowires connected to a second substrate 46. The second substrate 46 can be formed of any suitable material, such as sapphire or quartz.

The nanowire forming the substrate 28d can be formed from any suitable material capable of being formed into a nanowire and receiving a dopant, such as CdS:Mn. In one preferred embodiment, the diameter of the nanowire is 5 nm with a length of 2 micrometer, for example.

An optically pumped nanowire laser has been reported by P. D. Yang et al., *Room-temperature ultraviolet nanowire nanolasers*, Science, 2001, 292: 1879 and P. D. Yang, *Miniaturised Ultraviolet Lasers, Global Photonics Applications & Technology*, 2002, pp 42-47 by self-assembling ZnO nanowires vertically on a sapphire or quartz substrate. When the nanowires were pumped optically by a fourth harmonics of neodymium-doped yttrium-aluminum-garnet (Nd:YAG) laser at 266 nm, in the absence of any fabricated mirrors, lasing at wavelengths between 370 and 395 nm was observed from the ZnO nanowires. It was found by P. D. Yang that the interface between the sapphire and ZnO and the other end of the ZnO nanowires can function as excellent laser cavity mirrors. For II-VI semiconductors, the cleaved edge of the specimen on one of the sides can be used as a mirror.

The nanowire forming the substrate 28d includes a UCL material 30d positioned on or within the substrate 28d. An interface between the second substrate 46 and the substrate 28d forms one reflecting surface M3, and the other end of the substrate 28d forms another reflecting surface M4. A laser cavity 45 is formed between the reflecting surfaces M3 and M4.

The difference between the upconversion luminescence production assembly 20d and the lasers reported by P. D. Yang is the following. The upconversion luminescence production assembly 20d is based on upconversion luminescence, that is the excitation wavelength is longer than the emission wavelength, while, Yang's laser is based on photoluminescence, that is the excitation wavelength is shorter than the emission wavelength.

Upconversion Temperature Sensors

As shown in FIGS. 5-8, as the temperature fluctuates the luminescence intensity and emission wavelength will change (i.e. individual temperatures have unique luminescence intensities and mission wavelengths), and the upconversion luminescence of $ZnS:Mn^{2+}$ is more sensitive to temperature than photoluminescence.

Figure 11E:
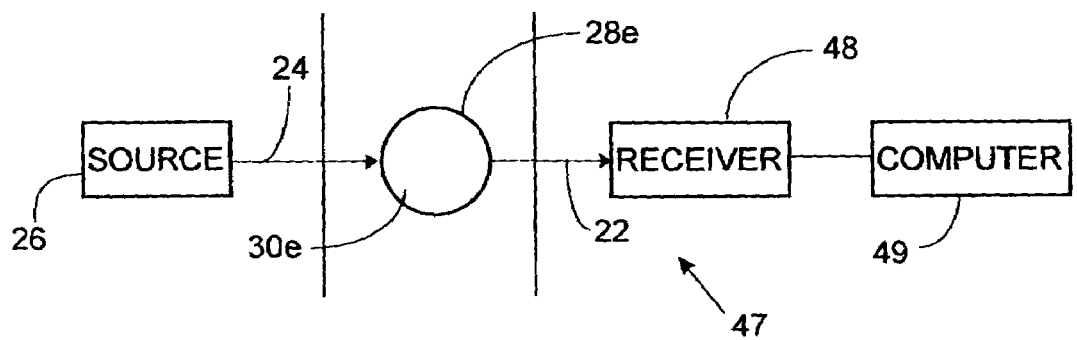
FIG. 11e is a schematic view of an upconversion temperature sensor constructed in accordance with the present invention.

Referring to FIG. 11e, shown therein is a temperature sensor 47 constructed in accordance with the present invention. The temperature sensor 47 includes the upconversion luminescence production assembly 20 discussed above, as well as a receiver 48 for receiving the emission 22 and outputting an output signal indicative of the emission 22. The output signal is received by a computer 49, which is programmed with a software program capable of determining the temperature of the UCL material based on the luminescence intensity and/or the emission wavelength.

The receiver 48 can be any device capable of receiving the emission 22 and producing the output signal. For example, the receiver can be a CCD, one or more phototransistors, one or more photodiodes or the like.

The temperature sensor 47 can be used for determining the temperature of materials, such as biological materials. When used for biological materials, the energy power or the power density of the excitation 24 should be maintained at a low level as discussed herein to avoid damaging the biological material. The temperature sensor 47 can be used for determining the temperature of the biological materials for use in treating patient conditions, such as hyperthermia or heat treatment of tumors or cancers. For example, the UCL material 30 can be formed of bulk and/or nanosized $ZnS:Mn^{2+}$.

The UCL material 30 can be bound or conjugated with biological material, such as a tumor within a human or non-human host, as discussed herein. In this instance, the electromagnetic source 26 and the receiver 48 are preferably positioned outside of the host's body. The excitation 24 will have a wavelength in the range of 700 to 1,000 nm and, more preferably, 800 nm, and which s capable of passing through at least a portion of the host's body so that the excitation 24 can be received by the UCL material 30 within the tumor. The UCL material 30 then creates the emission 22 having an emission wavelength, such as 600 nm and that is capable of passing through and exiting the host. In addition, the UCL of the nanoparticle inside the tumor or host can be excited and deflected through a tiny optical fiber.

As a temperature indicator in biological or biomedical applications, upconversion semiconductor nanoparticles have at least two advantages over organic dyes. One is semiconductor nanoparticles are more stable than organic dyes (W. C. W. Chan, S. Nie, *Quantum dot bioconjugates for ultrasensitive nonisotopic detection, Science*, (1998) 281, 2016 and M. J. Jr. Bruchez, M. M. Moronne, P. Gin, S. Weiss, P. A. Alivisatos, *Semiconductor nanocrystals as fluorescent biological labels*, Science, (1998), 281, 2013), the other is upconversion nanoparticles can provide more accurate measurement than organic fluorescent dyes because no autofluorescence is observed in upconversion measurement. As yet another example, the upconversion temperature sensor 47 can be made by coating nanoparticles to a tip or one end of an optical fiber. In this case, excitation and emission of the nanoparticles can be conducted or detected at the other end of the fiber. This kind of temperature sensor can be used for remote sensing of temperatures from a moving target like a turbine engine, a hot surface or in some hazardous conditions using a tiny fiber, this kind of temperature sensor also can be used to detect a body temperature of a human or non-human host.

Figure 12:
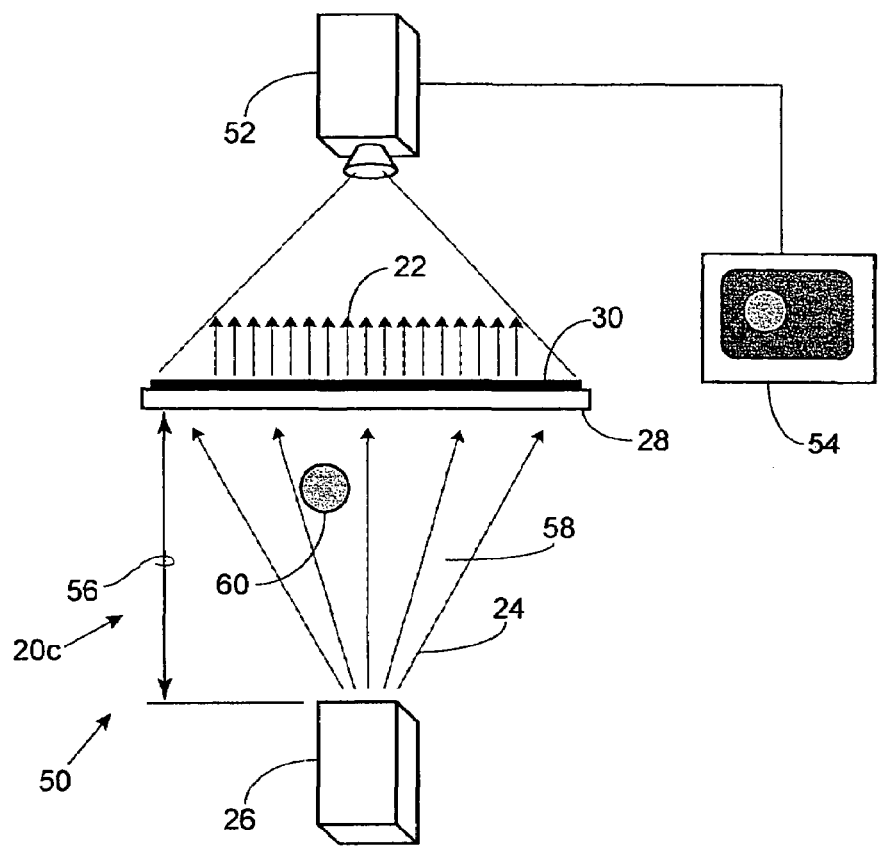
FIG. 12 is a schematic view of an upconversion imaging system constructed in accordance with the present invention.

Referring now to FIG. 12, shown therein is an upconversion imaging system 50 constructed in accordance with the present invention. The upconversion imaging system 50 is provided with an upconversion luminescence production assembly 20c, an imaging device 52, and an image processing system 54, such as a computer, PDA or any other electronic device capable of processing an electronic image data file. The upconversion luminescence production assembly 20c is similar to the upconversion luminescence production assembly 20 discussed above with reference to FIG. 11, except as discussed below.

The upconversion luminescence production assembly 20 includes the electromagnetic source 26, the substrate 28 and the UCL material 30 as discussed above. The substrate 28 is spaced a distance 56 from the substrate 28 so as to define a receiving space 58. The UCL material 30 is positioned within the excitation 24 produced by the electromagnetic source 26. An interfering object 60 is positioned within the receiving space 58 such that the interfering object 60 receives at least a portion of the excitation 24 and thereby interferes with the excitation 24. The interfering object 60 can be any article which blocks, magnifies, emits, reflects or otherwise alters the excitation 24. For example, the interfering object 60 can be a bone, a tumor or a hot spot.

At least a portion of the excitation 24 is received by the UCL material 30, which upconverts the excitation 24 to form the emission 22, as discussed above. The imaging device 52 captures one or more image of the emission 22, and provides the one or more image to the image processing system 54.

The image processing system 54 can be any device capable of executing image processing software such that the image is perceivable or otherwise usable by an individual. For example, the image processing system 54 can be a Windows-compatible or Macintosh compatible personal computer obtainable from Dell Computer Corporation of Austin Tex., Hewlett-Packard Company of Palo Alto Calif., International Business Machine of Armonk N.Y. or Apple Computer, Inc. of Cupertino Calif. The image processing software can be Photoshop Version 7.0 obtainable from Adobe Systems Incorporated of San Jose Calif.

Biological and Biomedical Applications

The upconversion luminescence material of the presently claimed and disclosed invention is also useful in biological systems as a sensor, probe, or label. The use of luminescent or fluorescent material as sensors, probes, or labels is well known in the art—the use of a bioconjugated UCL nanoparticle as a biological sensor, probe or label, however, is novel and has many advantages over the prior devices. Biomodified nanoparticles from a variety of inorganic materials are known in the art and such biomodified nanoparticles can be used in biological pursuits for luminescence tagging, drug delivery, and implantable microdevices as well as for assembling hybrid protein-nanoparticle units for molecular electronics. For example, Kotou, et al. have reported the conjugation of luminescent CdTe nanoparticles with bovine serum albumin. (N. A. Kotov, I. Dekany and J. H. Fendler, *Layer-by-layer self-assembly of polyelectrolyte-semiconductor nanoparticle composite films*, J. Phys. Chem. 1995, 99:13065-13069 have reported the conjugation of luminescent CdTe nanoparticles with bovine serum albumin. (Shaopeng Wang, Natalia Mamedova, Nicholas A. Kotov, Wei Chen, and Joel Studer, Antigen/Antibody Immunocomplex from CdTe Nanoparticle Bioconjugates, *Nanoletters*, 2002, 2(8): 817-822 the contents of which are hereby expressly incorporated by reference in their entirety).

In order to make UCL sensors, probes, or labels, the upconversion luminescence material must be conjugated to a biospecific ligand and/or have the ability to bind to a biological target (i.e. bioengineered or modified to have a surface state capable of binding to a biological target, such as a protein). One of ordinary skill in the art, given the present disclosure, would appreciate that the UCL material of the presently claimed and disclosed invention could be used as a biomodified probe or label, wherein the probe or label is specifically a biomodified nanoparticle.

Figure 13:
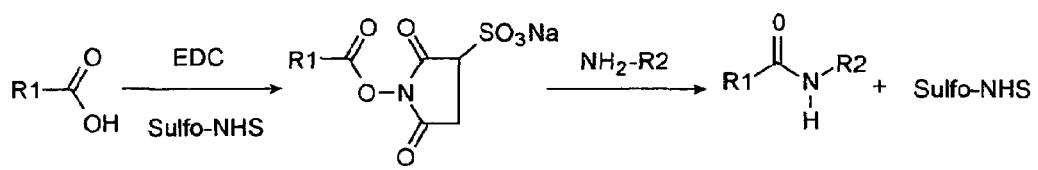
FIG. 13 is a schematic diagram of (1-ethyl-3(3-dimethylaminopropyl) carbodiimide hydrochloride)/sulfo-N-hydroxysulfo-succinimide conjugation reaction.

Bioconjugation of nanoparticles i.e. the attachment biospecific ligands to them, represents the intersection of biotechnology and nanotechnology which results in hybrid materials, processes, and devices that can utilize both the unique optical and magnetic properties of nanoparticles and highly selective binding of oligonucleotides and proteins. The combination of these features is highly desirable for current biomedical technologies. Particularly, the bioconjugation of nanoparticles with proteins can be used as (1) a method for their organization in more complex structures and (2) a pathway to new sensing and imaging technologies. Herein is disclosed the preparation of bioconjugates from an antigen and an antibody conjugated to nanoparticles of different size. The results show that the nanoparticle labeled antigen and antibody form an immunocomplex, which pairs together nanoparticles with red and green luminescence (see e.g. FIG. 13, for a diagrammatic outline of this immunocomplex).

These tests are related to the further development of immunoluminescence as a technique that affords highly sensitive and specific detection of various biological and non-biological analytes of military and civilian importance. The detection limits can be as low as 10 ppt with a linear dynamic range from 0.1 to 1000 ppb, while the utilization of antibodies enables selective detection substrates, which may differ only by a few atoms. Upconversion luminescent nanoparticles have opened new possibilities for biological labeling. It has been shown by others in the art, that nanoparticle bioconjugates selectively bind to cell components, DNA, or blood proteins and can be detected by strong luminescence which, in turn, is capable of being tuned by altering the particle size. The stability of nanoparticles makes possible not only high-contrast multiplexed imaging, but also a long-term monitoring of the environment—e.g. for biological warfare agents or natural pathogenic organisms such as cholera and *E. Coli*, which represent a critical problem for countries with limited water treatment capabilities. Notably, the use of UCL nanoparticle-bioconjugates does not require sample labeling/ staining. Additionally, when the nanoparticle is a UCL material (i.e. doped with a rare earth or transition metal ion), the upconversion luminescence provides for an even more reliable and easily manipulated biological probing sensing, or labeling system.

Materials and Methods

Thioglycolic-acid-stabilized CdTe nanoparticles were synthesized by the modified method reported in (W. Chen, D. Gronquist, and J. Roark, *Voltage tunable electroluminecsnce of CdTe nanoparticle light-emitting diodes*, J. Nanosci. Nanotechnol., 2002, 2: 47-53), the contents of which are expressly incorporated herein in their entirety. Generally, two different nanoparticle dispersions were utilized—one with a luminescence peak at 555 nm and the other with a luminescence peak at 611 nm. Nanoparticle-conjugated BSA and anti-BSA IgG were prepared by the sulfo-NHS(N-hydroxysulfo-succinimide) and EDC (1-ethyl-3(3-dimethylaminopropyl)carbodiimide hydrochloride) reaction (FIG. 13, as reported in Shaopeng Wang, Natalia Mamedova, Nicholas A. Kotov, Wei Chen, and Joel Studer, Antigen/Antibody Immunocomplex from CdTe Nanoparticle Bioconjugates, *Nanoletters*, 2002, 2(8): 817-822; Staros, J. V., *N-Hydroxysuffosuccinimide Active Esters: Bis (N-hydroxysulfosuccinimide) Esters of Two Dicarboxylic acids Are Hydrophilic, Membrane-impermeant, Protein Cross-linkers. Biochemistry* 1982, 21, 3950) the contents of which are expressly incorporated herein by reference in their entirety. NHS-conjugated proteins have the highest bioactivity among other conjugates as established by several comparative studies, which resulted in the departure from the previously used glutardialdehyde conjugation procedure. The carboxylic acid group of thioglycolic acid stabilized nanoparticle will form an amide bond with the primary amine groups of the protein.

We tested different reaction conditions and examined the results by native and SDS-PAGE gel electrophoresis. The following is the optimal protocol developed in the course of these experiments. A reaction mixture containing 0.05 mM CdTe nanoparticle, 1.5~2.5 mg/mL antigen or antibody, 0.05 M NHS, 0.05 M EDC in pH 7.0 PBS buffer were prepared and kept in room temperature for 2-4 hrs., then stored at 4° C. overnight, thereby allowing the unreacted EDC to hydrolyze and lose its activity. Thereafter, a small amount of precipitate is formed which is likely to consist from unconjugated nanoparticles, which are known to agglomerate and become non-emissive at low pH—e.g. pH≦7. The precipitate (if any) is removed by centrifugation. The stock, ready-to-use solution of the product was stored at 4° C. Optionally, one can dialyze it with Spectra/Por® 4 Membrane, MWCO: 12,000-14,000 (Spectrum Laboratories, Inc), in pH 7.4 PBS buffer.

Results and Discussion

The native electrophoresis results (FIG. 14, left panel) show that both nanoparticle-conjugated BSA (well 2) and anti-BSA IgG (well 4) bands become more mobile in the electric field than the unlabeled biospecific ligands (well 1 and 3). The BSA monomer band shifts from the relative marker of 65 kDa to 47 kDa, which makes evident that high negative charge of the nanoparticle and their compactness overcomes the increase of their mass due to labeling. Note that, the commercial BSA shows two other bands at 100 kDa and 150 kDa corresponding to BSA-BSA dimer and globulins respectively. This observation agrees with the specifications of Sigma; these compounds have minor influence on the biospecific reactions discussed herein below. Both of these bands shift synchronously with BSA monomer to smaller masses after the nanoparticle conjugation.

Figure 14:
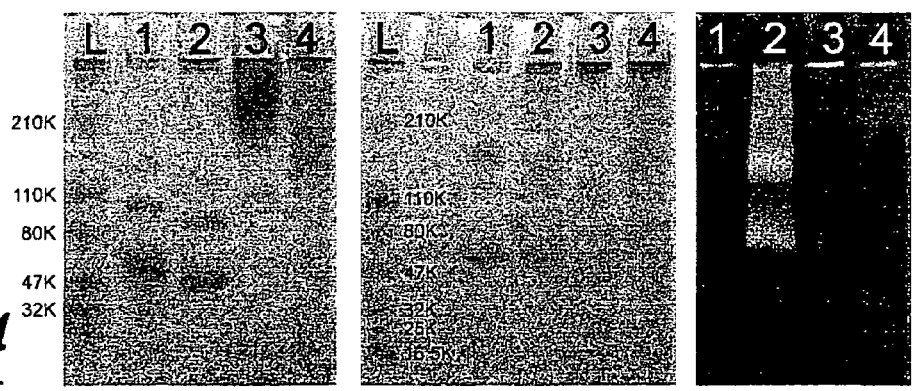
FIG. 14 is a graphical representation of Native and SDS-PAGE electrophoresis of CdTe bioconjugates on 4%-20% gradient Tris-HCl precast gels (Bio-Rad). Left panel—native, stained by Coomassie Blue. Center panel—SDS-PAGE, stained by Coomassie Blue. Right panel—SDS-PAGE, luminescence image (excitation 360 nm). Wells: 1) BSA; 2) green-emitting NP-BSA; 3) anti-BSA IgG; 4) red-emitting NP-IgG; L) standard protein ladder, molecular weight are marked on the side in kiloDaltons. (Note that in native electrophoresis, the position of the band is not linearly proportional to the molecular weight, due to the different charge status of each sample.)

The mobility of the proteins in SDS-PAGE electrophoresis (FIG. 14, center panel), is determined by the mass/charge ratio of denatured protein chains carrying sodium dodecyl sulfate (SDS), which imparts a negative charge to them. Interestingly, the band positions of nanoparticle-labeled and unlabeled proteins virtually coincide at 65 kDa marker (FIG. 14, center panel). Similarly to the native gel results, the increase of mass due to the addition of nanoparticles to the protein is compensated by the increase of the overall charge density of the conjugate. Unlike nanoparticle-BSA, the SDS-PAGE band of nanoparticle-IgG conjugate shifts to higher masses from a relative marker of 110 kDa to 150 kDa (FIG. 14, center panel, wells 3&4).

Considering SDS-PAGE data, two points are relevant to other nanoparticle bioconjugates: (1) estimates of molecular masses on the basis of gel electrophoresis results can give erroneous results for bioconjugates from highly charged nanoparticles; and (2) bioconjugation to nanoparticles may increase the stability of antibodies. A brief heat treatment for 150 seconds at 96° C. was used for the preparation of SDS-PAGE samples. The relative intensity of the SDS-PAGE bands indicates that the conjugated antibodies are more resilient to this temperature than the unlabeled ones. The unlabeled antibodies (well 3) are mostly broken apart by the heating into small fragments showing up as band at 40-50 kDa, while for nanoparticle-IgG conjugates, this band has significantly lower intensity—the antibody remains mostly intact. The latter effect was also reproduced in several control experiments. Thus, the conjunction of an antibody or other biological specimen/material results in a more stable construct capable of being used in what was previously considered adverse or unfavorable conditions.

The direct evidence of the successful conjugation of CdTe to BSA and IgG can be found from the luminescence analysis of the gel plates. The bands of nanoparticle conjugates display strong luminescence while the free proteins do not show any detectable signal in the luminescence image (FIG. 14, right panel). The gel pieces cut out of the gel plates in the area of the conjugate bands reveal the luminescence spectra with the peaks identical to the original nanoparticles that is 555 nm and 610 nm for nanoparticle-IgG and nanoparticle-BSA respectively, which proves the nanoparticle labeling of the proteins does not destroy or alter the luminescence properties of the nanoparticles that have been bioconjugated.

Figure 15:
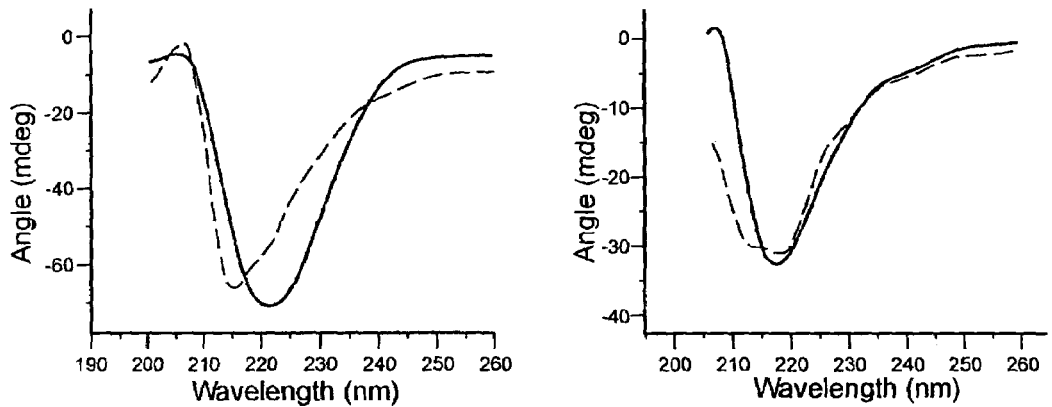
FIG. 15 is a graphical representation of Circular dichroism "CD" spectra of BSA (left panel) and Anti-BSA IgG (right panel) before (solid line) and after (dashed line) the conjugation to CdTe NPs. The spectra were recorded on a JASCO J-500A spectropolarimeter. Samples were dissolved in 0.01 M pH 7.4 PBS buffer. The initial solutions were diluted to approximately 1 mg/ml concentration immediately before the spectra were taken. A JASCO cell of path length 0.10 cm was used.

Circular dichroism (CD) spectra (FIG. 15) of BSA and nanoparticle-BSA conjugate are very similar to BSA-G-CdTe conjugate (Shaopeng Wang, Natalia Mamedova, Nicholas A. Kotov, Wei Chen, and Joel Studer, Antigen/Antibody Immunocomplex from CdTe Nanoparticle Bioconjugates, *Nanoletters*, 2002, 2(8): 817-822), which indicate a small disturbance of the BSA conformation observed around 210-220 nm. Besides that, the CD spectra coincided well with each other and with those of original BSA. This shows that the tertiary structure of BSA remains substantially intact, which is essential for the preparation of protein-based assemblies of nanoparticles. The actual biological activity of the conjugated anti-BSA IgG was examined by the standard ELISA (enzyme linked immunosorption assay) technique. Peroxidase-conjugated rabbit α-bovine IgG was used to label the anti-BSA IgG bond to BSA for colorized binding count. The binding affinity was determined to be 25~50% that of unlabeled IgG.

Figure 16:
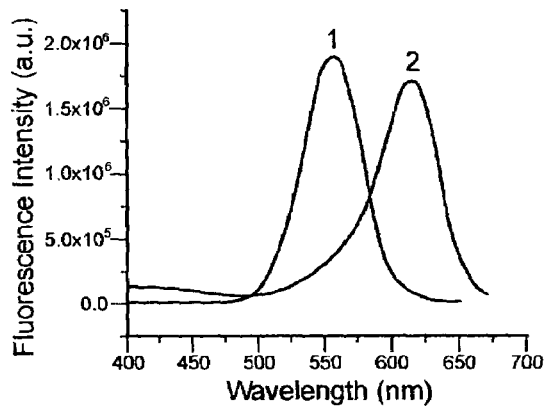
FIG. 16 is a graphical representation of fluorescence spectra of (1) NP-labeled anti-BSA IgG with green emission and (2) NP-labeled BSA with red emission. The excitation wavelength 340 nm.
Figure 17:
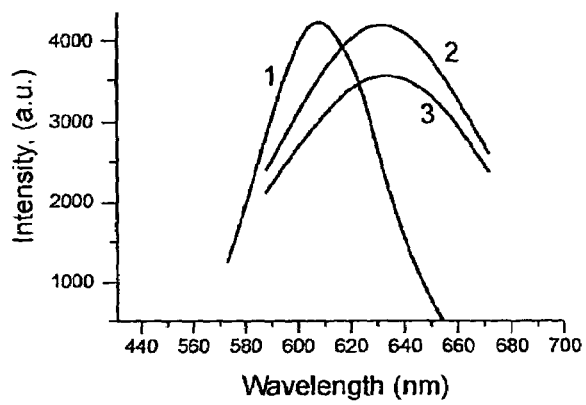
FIG. 17 is a graphical representation of photoluminescence (1) and upconversion emission of free CdTe nanoparticles (2) and Bru38-CdTe nanoparticle bioconjugates (3); Excitation wavelengths are 350 nm for (1) and 750 nm for (2) and (3); all the data were taken at pH 6.7.
Figure 18A:
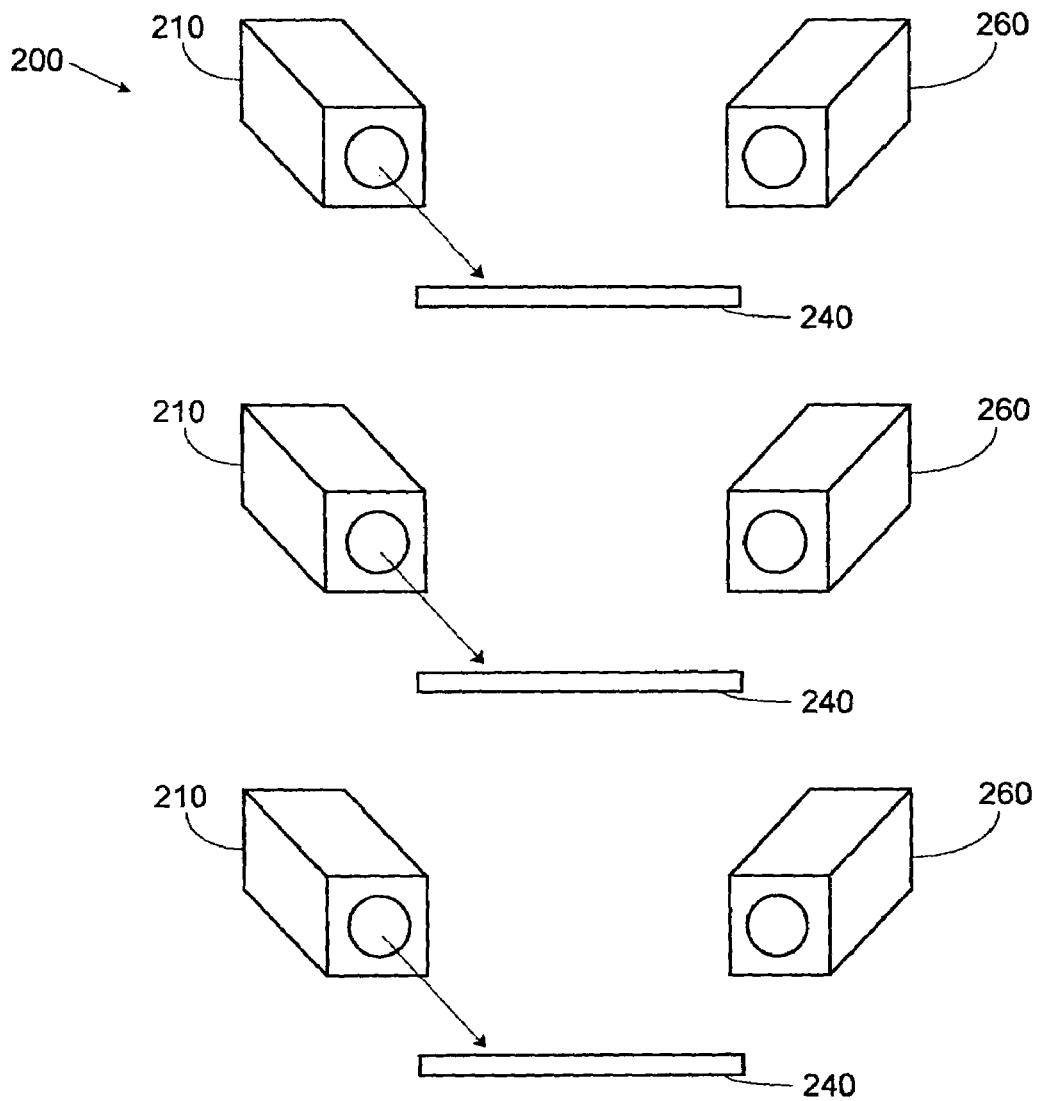
FIG. 18 is a schematic diagram of a UCL material sensor assembly.
Figure 18B:
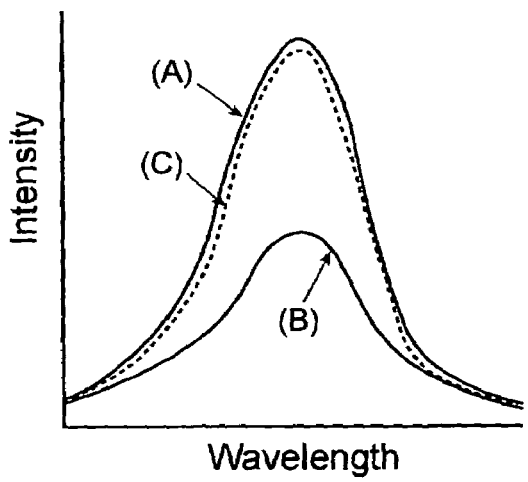

FIG. 16 shows the fluorescence spectra of the nanoparticle-BSA and nanoparticle-anti-BSA IgG conjugates in solution.

The emission peaks are at the same position as free nanoparticles. Additionally, the luminescence intensity does not decrease after storing the samples at 4° C. for over a month.

In summary, bioconjugates with complementary antigen and antibody have been prepared from thiolacid-stabilized nanoparticles. They retain substantial bioactivity and can form the corresponding immunocomplex, which pairs nanoparticles with different emission properties in one supramolecular assembly.

Nanoparticles demonstrating UCL properties have also been conjugated to biomaterials. In particular, CdTe nanoparticles exhibiting upconversion luminescence (W. Chen, D. Gronquist, and J. Roark, *Voltage tunable electroluminecsnce of CdTe nanoparticle light-emitting diodes*, J. Nanosci. Nanotechnol., 2002, 2: 47-53) were conjugated to dead *Brucella suis* and the corresponding antibody anti *Brucella Suis* and the conjugated bio-nanoparticle demonstrated UCL properties. According to the method described hereinabove with respect to BSA. Such a bioconjugated nanoparticle is even more useful in detection, sensor, and probe applications because of the enhanced detection and ease of detection owing to the UCL properties. The conjunction of the UCL nanoparticle with a biomaterial is detailed hereinafter.

UCL Nanoparticle Conjugated *B. suis* and Anti-*B. suis.*

For these experiments, a sample of dead *Brucella suis* (*B. suis*) [Strain 145] whole cells and the corresponding antibody Bru 38 for one of its membrane polysaccharides (Anti-GBa-O side chain) was obtained. Although the surface of the bacteria is complex, it contains numerous primary amine sites for nanoparticle binding. The *B. suis* whole cells were decorated with the green-emitting CdTe nanoparticles (561 nm) following the same conjugation protocol developed in the BSA experimental series described hereinabove, while Bru 38 was cross-linked to red-emitting nanoparticles (601 nm). The conjugated *B. suis* was purified by centrifuge and washed with 0.1 M PBS buffer three times. Native and SDS page gel electrophoresis results of the conjugated Bru 38 were similar to that of the nanoparticle-anti-BSA conjugate. The results demonstrate that the UCL nanoparticles can be bound to biomolecules.

Upconversion Luminescence of Bioconjugated CdTe Nanoparticles

In order to test the use of upconversion nanoparticles in biological labeling and biological sensors, CdTe nanoparticles were attached to the anti-*B. suis* as described above. Presently, it was determined that after the nanoparticles were bound to the biomaterial, upconversion luminescence was maintained. In the present experiments, bioconjugated nanoparticles (CdTe linked to anti *B. suis* IgG) still maintain strong upconversion luminescence and that their spectral positions were substantial the same as that of free nanoparticles (FIG. 17). This indicates that upconversion nanoparticles are ideal candidates for biological labeling and biological sensors applications.

For measuring the upconversion luminescence from the free or bioconjugated nanoparticles, the excitation wavelength from a Xenon lamp in a Spex Fluorolog fluorometer was set to 750 nm and a 600 nm optical filter was inserted to the excitation slit, and the emission was scanned from 550 nm to 700 nm. For the photoluminescence, the excitation wavelength was set to 350 nm and the emission was scanned from 550 nm to 700 nm. The shift of the upconversion emission peak from the photoluminescence peak demonstrated further that the 750 nm excited emission is due to upconversion or anti-Stokes luminescence. The shift of upconversion peak to longer wavelength is due to the involvement of surface states in the upconversion process (W. Chen, D. Gronquist, and J. Roark, *Voltage tunable electroluminecsnce of CdTe nanoparticle light-emitting diodes*, J. Nanosci. Nanotechnol., 2002, 2: 47-53).

One such sensing apparatus using a UCL bioconjugate material is shown in FIG. 18. The UCL bioconjugate sensor assembly 200 includes a excitation wave emitter 210 that emits an excitation wave 220 having an excitation wavelength 230, a substrate 240 having a UCL material 250 coated on at least a portion thereof, and an emission wave detector 260. In a preferred embodiment of the UCL bioconjugate sensor assembly 200, the UCL material 250 is a nanoparticle UCL material. In operation, the substrate 240 having the UCL material 250 thereon is placed so that at least one biomaterial 270 (e.g. a protein, DNA sequence, or antibody) can come into contact with the UCL material 250. Prior to the biomaterial 270 coming into contact with the UCL material 250, the excitation wave emitter 210 emits the excitation wave 220 so that the UCL material 250 receives the excitation wave 220 and upconverts the excitation wavelength 220 to an emission intensity 280 that can be detected by the emission wave detector 260. As shown in the graph depicted in FIG. 18A, as indicated by reference (A), the upconversion of excitation wavelength 220 to the emission intensity 280 prior to the biomaterial 270 contacting the UCL material 250 is shown. Once the biomaterial 270 contacts the UCL material 250, the emission intensity 280 is decreased as represented by reference (B) in FIG. 18A. When the biomaterial 270 is released from the UCL material 250, the emission intensity 280 returns to its normal state as represented by reference (C) in FIG. 18A. The decrease in emission intensity by a biomaterial could be due to energy transfer from the nanoparticles to the biomaterial or due to local states formed in the energy gap of the nanoparticles (N. S. Nalwa, Editor, *Handbook of Nanostructured Materials and Nanotechnology*, Academic Press, San Diego (2000), Vol. 4). In this manner, the UCL material of the present invention can be used as a sensor for biomaterials—indeed any material—that is capable of binding to the UCL material.

The strength of the present UCL material for use in sensing and detecting systems is shown graphically in FIG. 19. As we described, nanoparticles can be bioconjugated and used for biological labeling. In the conventional method, fluorescence from the nanoparticle-bioconjugated system was detected upon UV excitation. In this case, both the luminescence from the nanoparticles (designated as 1 in FIG. 19) and the luminescence from the biomolecules such as DNA, proteins, antigen or antibody (designated as 2 in FIG. 19) were observed. The luminescence from the biomolecules is called autofluorescence. Due to strong autofluorescence background upon UV excitation, the detection resolution in the fluorescence system is low as shown in FIG. 19A. Alternatively, using upconversion nanoparticles as shown in FIG. 19B, infrared light is used for excitation, no autofluorescence from the biomolecules but only the luminescence from the upconversion nanoparticles is observed. Thus, the resolution is improved greatly.

Light Converting Materials

From the above disclosure, we know what is called upconversion luminescence and the advantages of upconversion nanoparticles. On the contrary, photoluminescence or fluorescence in which the excitation energy is higher (shorter) than the emission energy (wavelength), is called down-conversion luminescence. Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$ have two functions, as down-conversion and upconversion luminescence. However, it should be understood that combinations of nanoparticles or bulk materials exhibiting only one or a combination of up-conversion luminescence and photoluminescence can be employed depending on the results desired. For example, one UCL material can be combined with a photoluminescing material to convert both IR light and UV light to visible light. That is, with a combination of the two types of luminescence, we can convert high energy light such as UV and low energy light such as IR to a medium energy light such as green.

Based on this idea and using the examples of the two-functional nanoparticles as mentioned (or two different nanoparticles or other sized materials each exhibiting single function), nanoparticles or other sized materials can be used to build light conveying substrates capable of being utilized as a window, light bulb, lens or for forming at least a portion of a greenhouse. It is well known that the sunshine spectrum is from UV to visible to IR, whereas most plants just take in the visible light such as green light for harvesting or growing or photosynthesis. The UV or IR light is actually not good for plant growth because the UV or IR light can damage or dry the plant tissues. If the UV and IR light are converted to visible light, this will be beneficial for growing plants like tomatoes, watermelon, grapes, etc.

As an example, referring to FIG. 20 shown therein and designated by a reference numeral 300 is a greenhouse constructed in accordance with the present invention. The greenhouse 300 is provided with one or more light conveying panel(s) 304 forming at least a portion of a shell 306. The shell defines an interior space 308 for receiving one or more botanical items 310. The botanical items 310 are disposed in one or more container(s) 312 containing a growing medium 314. The containers 312 can be supported by tables or benches 316 in a well known manner or positioned on a foundation or floor of the greenhouse 300.

The term "botanical item" when used herein means a natural or artificial herbaceous or woody plant, taken singly or in combination. The term "botanical item" also means any portion or portions of natural or artificial herbaceous or woody plants including stems, leaves, flowers, blossoms, buds, blooms, cones, propagules, other foliage or roots taken singly or in combination, or in groupings of such portions such as a bouquet or a floral grouping.

The term "propagule" when used herein means any structure capable of being propagated or acting as an agent of reproduction including seeds, shoots, stems, runners, tubers, plants, leaves, roots or spores.

The term "growing medium" when used herein means any liquid, solid or gaseous material used for plant growth or for the cultivation of botanical items 310, including organic and inorganic materials such as soil, humus, perlite, vermiculite, sand, particulate matter, water, and including the nutrients, fertilizers or hormones or combinations thereof required by the botanical items 310 for growth or survival.

The term "container" as used herein refers to any type of device used for holding a botanical item and/or growing medium. Examples of containers, used in accordance with the present invention, include but are not limited to: clay pots, wooden pots, plastic pots, foam pots, growing trays including metal trays and plastic trays, pots made from natural and/or synthetic fibers, or any combination thereof.

Shown in FIG. 21 is a partial cross-sectional view of one of the light conveying panels 304, taken along the lines 21-21 in FIG. 20. The light conveying panel 304 includes a substrate 320 having a light converting material 322 provided either on, within or adjacent to the substrate 320. The light conveying panel 304 can be used for making a window, lens, skylight or other type of translucent or transparent device.

The light converting material 322 can be provided on an exterior surface 326 or an interior surface 328 of the substrate 320. The substrate 320 can be made of any type of rigid, semi-rigid, crystalline, or flexible translucent or transparent material, such as silica glass, carbonate treated polymer, carbonate heated polymer, or plastic.

The light converting material 322 can be formed of one material having both downconversion and upconversion abilities, as discussed above or combinations of a UCL material and a down-converting material. For example, one UCL material as discussed above can be combined with a photoluminescing material to convert both IR light and UV light to visible light. With a combination of the two types of luminescence, high energy light such as UV and low energy light such as IR are converted to a medium energy light such as green.

Alternatively, or in addition, as shown in FIG. 22, the light converting material 322 can be coated onto at least a portion of one or more of the botanical items 310 for converting the high energy light and low energy light to medium energy light as discussed above. For example, the light converting material 322 can be sprayed onto the botanical items.

Either way, the converting of the IR and UV light to visible light as discussed herein may help the botanical items 310 grow faster, higher, and/or shorten the period of time for maturation or harvesting.

Thus, it should be apparent that there has been provided in accordance with the present invention upconversion luminescence material and methods of making and using same that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

REFERENCES

The following references, to the extent that they provide exemplary procedural or other details supplementary to those set forth herein, are specifically incorporated herein by reference in their entirety as though set forth herein in particular.

W. Lenth, and R. M. Macfarlane, *Upconversion lasers*, Optics and Photonics News, (March, 1992), pp 8-14

J. C. Wright, *Upconversion and excited state energy transfer in rare-earth doped materials*, in Topics in Applied Physics: Radiation Processes in Molecules and Condensed Phase; F. K. Fong., Ed.; Springer: Berlin, (1976), pp 239-295

R. Scheps, *Upconversion laser processes*, Prog. Quant. Electr. (1996), 20, 271

H. X. Zhang, C. H. Kam, Y. Zhou, X. Q. Han, S. Buddhudu, and Y. L. Lam, *Visible upconversion luminescence in $Er^{3+}$: $BaTiO_3$ nanocrystals*, Optical Materials, (2000), 15, 47

C. E. Mungan, T. R. Gosnell, *Laser cooling of solids*, Advances in Atomic, Molecular, and Optical Physics, (1999), 40,161

H. U. Gudel et al., *Design of luminescent inorganic materials: New photophysical processes studied by optical spectroscopy*, Acc. Chem. Res. (2000) 33, 235

H. U. Gudel et al., *New photon upconversion processes in $Yb^{3+}$ doped $CsMnCl_3$ and $RbMnCl_3$*, Chemical Physics Letters, (2000), 320, 639

R. N. Bhargava, D. Gallagher, X. Hong and A. Nurmikko, *Optical properties of Manganese-doped nanocrystals of ZnS*, Phys. Rev. Lett. (1994), 72, 416

M. Kaszuba, *The measurement of nanoparticles using photon correlation spectroscopy and avalanche photo diodes*, Journal of Nanoparticle Research, (1999), 1, 405

M. J. Jr. Bruchez, M. M. Moronne, P. Gin, S. Weiss, P. A. Alivisatos, *Semiconductor nanocrystals as fluorescent biological labels*, Science, (1998), 281, 2013

W. C. W. Chan, S. Nie, *Quantum dot bioconjugates for ultrasensitive nonisotopic detection, Science*, (1998) 281, 2016

D. A. Zarling, M. J. Rossi, N. A. Peppers, J. Kane, G. W. Faris, M. J. Dyer, S. Y. Ng, and L. V. Schneider, Up-converting reporters for biological and other assays using laser excitation techniques, U.S. Pat. No. 5,891,656, Apr. 6, 1999

H. Zijlmans, J. Bonnet, J. Burton, K. Kardos, T. Vail, R. S. Niedbala, and H. J. Tanke, *Detection of cell and tissue surface antigens using up-converting phosphors: A new reporter Technology*, Analytical Biochemistry, (1999) 267, 30

P. P. Paskov et al., *Photoluminescence upconversion in InAs/GaAs self-assembled quantum dots*, Appl. Phys. Lett. 77, 812 (2000).

I. V. Ignatiev et al., *Anti-Stokes photoluminescence of InP self-assembled quantum dots in presence of electric current*, Phys. Rev. B 60, R14 001 (1999).

W. Heimbrodt, H. Falk, and P. J. Klar, *Luminescence, energy transfer and anti-Stokes PL in wide band-gap semimagnetic nanostructures*, J. Lumin. 87-89, 344(2000).

L. A. Golovan et al., Observation of two-step excitation of photoluminescence in silicon nanostructures, Pisma Zh. Eksp. Teor. Fiz. 68, 732 (1998) @JETPLett. 68, 770 (1998)#.

S. A. Blanton, M. A. Hines, M. E. Schmidt, and P. Guyot-Sionnest, *Two-photon spectroscopy and microscopy of II-VI semiconductor nanocrystals*, J. Lumin. 70, 253 (1996).

E. Poles, D.C. Selmarten, O. I. Micc, and A. J. Nozik, *Anti-Stokes photoluminescence in colloidal semiconductor quantum dots*, Appl. Phys. Lett. 75, 971 (1999).

B. A. Smith, J. Z. Zhang, A. Joly, and J. Liu, *Luminescence decay kinetics of Mn2+-doped Zns nanoclusters grown in reverse micelles*, Phys. Rev. B 62, $20^{2+}$ (2000).

Y.-H. Cho, D. S. Kim, and B.-D. Choe, *Dynamics of anti-Stokes photoluminescence in type-II $Al_xGa_{1-x}As$-$GaInP_2$ heterostructures: The important role of long-lived carriers near the interface*, Phys. Rev. B 56, R4375 (1997).

M. Pollnau et al., *Power dependence of upconversion luminescence in lanthanide and transition-metal-ion system*, Phys. Rev. B 61, 3337 (2000).

V. I. Klimov et al., *Quantization of multiparticle auger rates in semiconductor quantum dots*, Science 287, 1011 (2000).

F. Wu, J. Z. Zhang, R. Kho, and R. K. Mehra, *Radiative and nonradiative lifetimes of band edge states and deep trap states of CdS nanoparticles determined by time-correlated single photon counting*, Chem. Phys. Lett. 330, 237 (2000).

F. A. J. M. Driessen et al., *Interface-induced conversion of infrared to visible light at semiconductor interfaces*, Phys. Rev. B 54, R5263 (1996).

W. Hoheisel, V. L. Colvin, C. S. Johnson, and A. P. Alivisatos, THRESHOLD FOR QUASICONTINUUM ABSORPTION AND REDUCED LUMINESCENCE EFFICIENCY IN CDSE NANOCRYSTALS, J. Chem. Phys. 101, 8455 (1994).

P. A. M. Rodrigues, G. Tamulaitis, P. Y. Yu, and S. H. Risbud, SIZE-SELECTIVE PHOTOLUMINESCENCE EXCITATION SPECTROSCOPY IN CDSE NANOCRYSTALS, Solid State Commun. 94, 583 (1995).

N. S. Nalwa, Editor, *Handbook of Nanostructured Materials and Nanotechnology*, Academic Press, San Diego (2000), Vol. 4.

K. Sooklal, B. S. Cullum, S. M. Angel, and C. J. Murphy, *Photophysical properties of ZnS nanoclusters with spatially localized $Mn^{2+}$*, J. Phys. Chem. 100, 4551 (1996).

G. Counio, T. Gacoin, and J. P. Boilot, *Synthesis and photoluminescence of $Cd_{1-x}Mn_xS$ (x<=5%) nanocrystals*, J. Phys. Chem. B 102, 5257 (1998).

J. Q. Yu, H. M. Liu, Y. Y. Wang, F. E. Fernandez, and W. Y. Jia, *Optical properties of ZnS:Mn2+ nanoparticles in polymer films*, J. Lumin. 76&77, 252 (1998).

A. A. Bol and A. Meijerink, *Long-lived $Mn^{2+}$ emission in nanocrystalline $ZnS:Mn^{2+}$*, Phys. Rev. B 56, R15997 (1998).

N. Murase et al., *Fluorescence and EPR characteristics of $Mn^{2+}$-doped ZnS nanocrystals prepared by aqueous colloidal method*, J. Phys. Chem. B 103, 754 (1999).

A. Dinsmore et al., *Mn-doped ZnS nanoparticles as efficient low-voltage cathodoluminescent phosphors*, Appl. Phys. Lett. 75, 802 (1999).

W. Chen, R. Sammynaiken, and Y. Huang, *Luminescence enhancement of ZnS:Mn nanoclusters in zeolite*, J. Appl. Phys. 88, 5188 (2000).

W. Chen et al., *Crystal field, Phonon coupling and emission shift of $Mn^{2+}$ in ZnS:Mn nanoparticles*, J. Appl. Phys. 89,1120 (2001).

W. Chen, A. G. Joly, and Z. Z. Zhang, *Upconversion luminescence of $Mn^{2+}$ in $ZnS:Mn^{2+}$ nanoparticles*, Phys. Rev. B 64, 41, 202 (2001).

J. Z. Zhang, *Ultrafast studies of electron dynamics in semiconductor and metal colloidal nanoparticles: Effects of size and surface*, Acc. Chem. Res. 30, 423 (1997).

M. Nirmal, C. B. Murray, D. J. Norris, and M. G. Bawendi, SURFACE ELECTRONIC-PROPERTIES OF CDSE NANOCRYSTALLITES, Z. Phys. D 26, 361 (1993).

D. J. Norris, M. Nirmal, C. B. Murray, A. Sacra, and M. G. Bawendi, SIZE-DEPENDENT OPTICAL SPECTROSCOPY OF II-VI SEMICONDUCTOR NANOCRYSTALLITES (QUANTUM DOTS), Z. Phys. D 26, 355 (1993).

N. P. Ernsting, M. Kaschke, H. Weller, and L. Katsikas, COLLOIDAL $Zn_{1-x}Cd_xS$—OPTICAL SATURATION OF THE EXCITON BAND AND PRIMARY PHOTOCHEMISTRY STUDIED BY SUBPICOSECOND LASER FLASH—PHOTOLYSIS, J. Opt. Soc. Am. B 7, 1630 (1990).

G. A. Ozin, NANOCHEMISTRY—SYNTHESIS IN DIMINISHING DIMENSIONS, Adv. Mater. 4, 612 (1992).

D. D. Thong and O. Goede, OPTICAL STUDY OF HIGHLY Mn-DOPED ZNS CRYSTALS, Phys. Status Solidi B 120, K145 (1983).

M. Tanaka, and Y. Masumoto, *Very weak temperature quenching in orange luminescence of ZnS:Mn2+ nanocrystals in polymer*, Chem. Phys. Lett. 324, 249 (2000).

G. G. ZEGRYA; V. A. KHARCHENKO VA, A NEW MECHANISM FOR AUGER RECOMBINATION OF NONEQUILIBRIUM CURRENT CARRIERS IN SEMI-CONDUCTING HETEROSTRUCTURES, Zh. Eksp. Teor. Fiz, 1992, 101:327; Sov. Phys. JETP., 1992, 74:173

N. Hamelin, P. G. Kik, J. F. Suyver, K. Kikoin, A. Polman, A. Schn̈onecker, and F. W. Saris, *Energy backtransfer and infrared photoresponse in erbium-doped silicon p-n diodes, J. Appl. Phys.* 88, 5381 (2000).

M. Kaszuba, *The measurement of nanoparticles using photon correlation spectroscopy and avalanche photo diodes*, J. Nanoparticle Research, 1999, 1, 405-409

W. Chen, X. H. Zhang, and Y. Huang, *Luminescence enhancement of EuS nanoclusters in zeolite*, Appl. Phys. Lett., 2000, 24, 2328-2330

M. Kapitonov et al., *Luminescence properties of tiol-stabilized CdTe nanocrystals*, J. Phys. Chem. B, 1999, 103: 10109-10113

W. Chen, D. Gronquist, and J. Roark, *Voltage tunable electroluminecsnce of CdTe nanoparticle light-emitting diodes*, J. Nanosci. Nanotechnol., 2002, 2: 47-53

G. Decher, *Fuzzy nanoassemblies: toward layered polymeric multicomposites*, Science, 1997, 277: 1232-1237

N. A. Kotov, I. Dekany and J. H. Fendler, *Layer-by-layer self-assembly of polyelectrolyte-semiconductor nanoparticle composite films*, J. Phys. Chem. 1995, 99:13065-13069

L. A. Riseberg and H. W. Moos, *Multiphonon orbit-lattice relaxation of excited states of rare-earth ions in crystals*, Phys. Rev. 1968, 174: 429

J. M. F. van Dijk and M. F. H. Schuurmans, *On the nonradiative and radiative decay rates and a modified exponential energy gap law for 4f-4f transitions in rare-earth ions*, J. Chem. Phys. 1983, 78: 5317-5323

P. Egger and J. Hulliger, *Optical materials for short wavelength generation*, Coordination Chemistry Review, 1999, 183:101-115

A. Anastassiadou et al., *The luminescence spectrum of Zn1-xMnxS under hydrostatic pressure*, Solid State Communications, 1988, 67:633-636

P. Xie and S.C. Rand, *Astigmatically compensated, high gain cooperative upconversion laser*, Applied Physics Letters, 1992, 60: 3084-3086

P. D. Yang et al., *Room-temperature ultraviolet nanowire nanolasers*, Science, 2001, 292: 1879

P. D. Yang, *Miniaturised Ultraviolet Lasers, Global Photonics Applications & Technology*, 2002, pp 42-47

Alivisatos, A. P. Et al., *Semiconductor Nanocrystals as Fluorescent Biological Labels*, Science 1998, 281,2013.

Chan, W. C. W.; Nie, S., *Quantum Dot Bioconjugates for Ultrasensitive Nonisotopic Detection*, Science 1998, 281, 2016.

Staros, J. V., *N-Hydroxysuffosuccinimide Active Esters:Bis (N-hydroxysulfosuccinimide) Esters of Two Dicarboxylic acids Are Hydrophilic, Membrane-impermeant, Protein Cross-linkers*. Biochemistry 1982, 21, 3950.

Shaopeng Wang, Natalia Mamedova, Nicholas A. Kotov, Wei Chen, and Joel Studer, *Antigen/Antibody Immunocomplex from CdTe Nanoparticle Bioconjugates*, Nanoletters, 2002, 2(8): 817-822

What I claim is:

1. A method of using a bioconjugated upconversion luminescent nanoparticle system for biological labeling, comprising the steps of:
    delivering a bioconjugated upconversion luminescent nanoparticle system to a target,
    binding the bioconjugated upconversion luminescent nanoparticle system to the target, and
    measuring upconversion luminescence from the bioconjugated upconversion luminescent nanoparticle system bound to the target, wherein an emission wavelength of the bioconjugated upconversion luminescent nanoparticle is shorter than an excitation wavelength of the bioconjugated upconversion luminescent nanoparticle, wherein the upconversion luminescent nanoparticle of the bioconjugated upconversion luminescent nanoparticle system has the general formula (X):(Mn, R), wherein
    (X) is a host having a size less than 100 nm and is represented by the formula $(M_{1-z}N_z)_{1-x}A_{1-y}B_y$, where M=Zn, Cd, Pb, Ca, Ba, Sr, and Mg; N=Zn, Cd, Pb, Ca, Ba, Sr, and Mg; A=S, Se, Te, and O; B=S, Se, Te, and O, wherein $0 \leq x < 1$, $0 < y \leq 1$, $0 < z \leq 1$, and
    (R) is a rare earth ion.

2. The method of claim 1, wherein the emission wavelength is 750 nm and the excitation wavelength is 980 nm.

3. The method of claim 1, wherein the host is selected from the group consisting of $Zn_{1-x}S_y$, $Zn_{1-x}Se_y$, $Zn_{1-x}Te_y$, $Cd_{1-x}S_y$, $Cd_{1-x}Se_y$, $Cd_{1-x}Te_y$, $Pb_{1-x}S_y$, $Pb_{1-x}Se_y$, $Pb_{1-x}Te_y$, $Mg_{1-x}S_y$, $Ca_{1-x}S_y$, $Ba_{1-x}S_y$, and $Sr_{1-x}S_y$, wherein $0 \leq x < 1$, and $0 < y \leq 1$.

4. The method of claim 1, wherein the nanoparticle host is $Zn_{0.4}Cd_{0.4}S$.

5. The method of claim 1, wherein the nanoparticle host is $Zn_{0.9}S_{0.8}Se_{0.2}$.

6. The method of claim 1, wherein the rare earth ion is selected from the group consisting of $Eu^{3+}$, $Tb^{3+}$, $Ce^{3+}$ or $Er^{3+}$.

7. The method of claim 1, wherein the upconversion luminescent nanoparticle is selected from the group consisting of ZnS:Mn,Er; ZnSe:Mn,Er; MgS:Mn,Er; CaS:Mn,Er; ZnS:Mn,Yb; ZnSe:Mn,Yb; MgS:Mn,Yb; CaS:Mn,Yb and ZnS:Mn, Eu.

8. The method of claim 7, wherein the upconversion luminescent nanoparticle of the bioconjugated upconversion luminescent nanoparticle system is ZnS:Mn,Yb.

9. The method of claim 1, wherein the bioconjugate component of the bioconjugated upconversion luminescent nanoparticle system is selected from the group consisting of antibodies, antigens, proteins, lipids, sugars, liposomes, bacteria, DNA, RNA and combinations thereof.

10. The method of claim 9, wherein the bioconjugate component of the bioconjugated upconversion luminescent nanoparticle system is bovine serum albumin.

11. The method of claim 1, wherein the bioconjugated upconversion luminescent nanoparticle system comprises upconversion luminescent nanoparticles and biomolecules that are linked by bioconjugation.

12. The method of claim 1, wherein the bioconjugated upconversion luminescent nanoparticle system comprises upconversion luminescent nanoparticles and biomolecules that are linked by chemical bonds.

13. The method of claim 1, wherein the bioconjugated upconversion luminescent nanoparticle system comprises upconversion luminescent nanoparticles and biomolecules that are linked by a ligand bound to a receptor.

14. The method of claim 1, wherein the method is performed in vivo.

15. The method of claim 1, wherein the method is performed in vitro.

16. The method of claim 1, wherein the target is selected from the group consisting of a tumor or a bacterial agent.

17. The method of claim 16, wherein the target is *Escherichia coli*.

18. The method of claim 16, wherein the target is cholera.

19. The method of claim 1, wherein the target is chosen from the group consisting of cell components, DNA, DNA sequences, proteins, and antibodies.

* * * * *

UNITED STATES PATENT AND TRADEMARK OFFICE
CERTIFICATE OF CORRECTION

Page 1 of 2

PATENT NO. : 7,501,092 B2
APPLICATION NO. : 11/202005
DATED : March 10, 2009
INVENTOR(S) : Wei Chen It is certified that error appears in the above-identified patent and that said Letters Patent is hereby corrected as shown below:

Title page, Item [56]
On Page 2, under "Other Publications", the following references should be added before the reference:

"FELIX, C., C. SIEBER, W. HARBICH, J. BUTLET, I. RABIN, W. SCHULZE, AND G. ERTL, "Fluorescence and Exitation Sprectra of Ag4 in an Argon Matrix," Chem. Phys. Lett., vol. 313, iss. 1-2, pp. 105-109 (November 5, 1999)."

-- CRAWFORD, M.K. AND L. H. BRIXNER, "Photostimulable Phosphors for X-Ray Imaging: Applications and Mechanism," J. Lumin., vol. 48-49 part 1 iss., pp. 37-42 (Jan-Feb. 1991).

CURTHBERT, J.D. AND D. G. THOMAS, "Fluorescent Decay Times of Excitons Bound to Isoelectronic Traps in GaP and ZnTe," Phys. Rev. Series II, vol. 154, iss. 3, pp. 763-771 (Feb. 1967).

DECHER, G.; HONG, J. D. "Buildup of Ultrathin Multilayer films By A Self-Assembly Process: I. Consecutive Adsorption of Anionic and Cationic Bipolar Amphiphiles," Macromol. Chem., Macromol.Symp. Vol. 46, pp. 321 (1991).

DECHER, G.; LEHR, B.; LOWACK, K.; LVOV, Y.; SCHMITT, J., "New Nanocomposite Films for Biosensors: Layer-by-layer Adsorbed Films of Polyelectrolytes, Proteins or DNA," BIOSENSORS & BIOELECTRONICS, vol. 9, iss. 9-10, pp. 677-684 (1994).

DECHER, G., "Fuzzy nanoassemblies: Toward Layered Polymeric Multicomposites," Scienc.

DINSMORE, A. ET AL., "Mn-doped ZnS Nanoparticles As Efficient Low-Voltage Cathodoluminescent Phosphors," Appl. Phys. Lett., vol. 75, iss. 6, pp. 802-804 (Aug. 9, 1999).

Signed and Sealed this
Twenty-third Day of August, 2011

David J. Kappos
*Director of the United States Patent and Trademark Office*

DONG, Y. AND M. Z. SU, "Luminescence and Electro-Conductance of BaFBr:Eu2+ Crystals During X-irradiation and Photostimulation," J. Lumin., vol. 65, iss. 5, pp. 263-268 (Oct. 1995).

EGGER, P. AND J. HULLIGER, "Optical Materials For Short Wavelength Generation," Coordination Chemistry Review, 1999, 183:101-115.

ERNSTING, N.P., M. KASCHKE, H. WELLER, AND L. KATSIKAS, "Colloidal Zn1-xCdxS - Optical Saturation of the Exciton Band and Primary Photochemistry Studied By Subpicosecond Laser Flash-Photolysis," J. Opt. Soc. Am. B, vol. 7, iss. 8, pp. 1630-1637 (July 1990).

FAN, W., Y. WANG, X. HOU, L. DU, W. ZHAO, B. YANG, AND L. NIU, "Picosecond Infrared Laser Stimulation of Luminescence in CaS:Eu,Sm," J. Appl. Phys., vol. 85, iss. 1, pp. 451-454 (Jan. 1, 1999).

FEDRIGO, S., W. HARBICH, AND J. BUTTET, "Optical Response of Ag2, Ag3, Au2, and Au3 in Argon Matrices," J. Chem, Phys., vol. 99, iss. 8, pp. 5712-5717 (Oct. 15, 1993). --

In the Specification:
Column 25, line 49: Delete "accurately" and replace with -- arcuately --.